US009974753B2

(12) United States Patent
Salman et al.

(10) Patent No.: US 9,974,753 B2
(45) Date of Patent: May 22, 2018

(54) NANOPARTICLES COMPRISING A VEGETABLE HYDROPHOBIC PROTEIN AND A WATER MISCIBLE NON-VOLATILE ORGANIC SOLVENT AND USES THEREOF

(71) Applicant: BIONANOPLUS, S.L., Noáin-Navarra (ES)

(72) Inventors: Hesham H. A. Salman, Noáin-Navarra (ES); Izaskun Goñi Azcárate, Noáin-Navarra (ES); Irene Esparza Catalán, Noáin-Navarra (ES)

(73) Assignee: BIONANOPLUS, S.L., Noáin-Navarra (ES)

( * ) Notice: Subject to any disclaimer, the term of this patent is extended or adjusted under 35 U.S.C. 154(b) by 102 days.

(21) Appl. No.: 14/378,266

(22) PCT Filed: Feb. 12, 2013

(86) PCT No.: PCT/EP2013/052795
§ 371 (c)(1),
(2) Date: Aug. 12, 2014

(87) PCT Pub. No.: WO2013/120856
PCT Pub. Date: Aug. 22, 2013

(65) Prior Publication Data
US 2015/0004102 A1  Jan. 1, 2015

(30) Foreign Application Priority Data

Feb. 13, 2012  (EP) .................... 12382049

(51) Int. Cl.
| *A61K 9/51* | (2006.01) |
| *A01N 25/28* | (2006.01) |
| *A61K 9/00* | (2006.01) |
| *A23J 3/14* | (2006.01) |
| *A61K 8/64* | (2006.01) |
| *A61Q 19/00* | (2006.01) |
| *A61K 8/02* | (2006.01) |
| *A61K 8/14* | (2006.01) |
| *B01J 13/02* | (2006.01) |
| *C09B 67/02* | (2006.01) |
| *C09B 67/08* | (2006.01) |
| *B82Y 30/00* | (2011.01) |
| *A61K 9/16* | (2006.01) |
| *A61K 31/155* | (2006.01) |
| *A61K 31/202* | (2006.01) |
| *A61K 35/60* | (2006.01) |
| *A61K 38/38* | (2006.01) |
| *A61K 49/00* | (2006.01) |
| *A61Q 13/00* | (2006.01) |
| *A23K 40/30* | (2016.01) |
| *A23P 10/30* | (2016.01) |
| *A23L 33/10* | (2016.01) |
| *A23L 33/115* | (2016.01) |

(52) U.S. Cl.
CPC .......... *A61K 9/5169* (2013.01); *A01N 25/28* (2013.01); *A23J 3/14* (2013.01); *A23K 40/30* (2016.05); *A23L 33/10* (2016.08); *A23L 33/115* (2016.08); *A23P 10/30* (2016.08); *A61K 8/0241* (2013.01); *A61K 8/0283* (2013.01); *A61K 8/14* (2013.01); *A61K 8/645* (2013.01); *A61K 9/006* (2013.01); *A61K 9/1641* (2013.01); *A61K 9/1658* (2013.01); *A61K 9/1682* (2013.01); *A61K 9/5146* (2013.01); *A61K 9/5192* (2013.01); *A61K 31/155* (2013.01); *A61K 31/202* (2013.01); *A61K 35/60* (2013.01); *A61K 38/385* (2013.01); *A61K 49/0093* (2013.01); *A61Q 13/00* (2013.01); *A61Q 19/00* (2013.01); *B01J 13/02* (2013.01); *B82Y 30/00* (2013.01); *C09B 67/0005* (2013.01); *C09B 67/0013* (2013.01); *C09B 67/0097* (2013.01); *A23V 2002/00* (2013.01); *A61K 2800/10* (2013.01)

(58) Field of Classification Search
CPC combination set(s) only.
See application file for complete search history.

(56) References Cited

U.S. PATENT DOCUMENTS

| 5,324,351 A | 6/1994 | Oshlack et al. |
| 5,330,778 A | 7/1994 | Stark et al. |
| 6,020,008 A | 2/2000 | Li |
| 6,746,635 B2 | 6/2004 | Mathiowitz et al. |
| 6,858,238 B2 | 2/2005 | Lee et al. |
| 8,167,990 B2 * | 5/2012 | De Saint-Romain ............ A23G 3/0097 106/31.27 |
| 2003/0108669 A1 | 6/2003 | Mathiowitz et al. |
| 2004/0001903 A1 | 1/2004 | Lee et al. |

(Continued)

FOREIGN PATENT DOCUMENTS

| EP | 0434760 B1 | 1/1994 |
| EP | 0499619 B1 | 2/1996 |

(Continued)

OTHER PUBLICATIONS

Duclairoir, C., et al.; "Formation of fliadin nanoparticles: Influence of the solubility parameter of protein solvent," Colloid and Polymer Science, 1998, pp. 321-327, vol. 276.

(Continued)

*Primary Examiner* — Robert S Cabral
(74) *Attorney, Agent, or Firm* — Tristan Fueirer; Moore & Van Allen, PLLC

(57) ABSTRACT

The present invention relates to nanoparticles for encapsulating compounds, the preparation and uses thereof, said nanoparticles being based on a vegetable hydrophobic protein, particularly zein, and a water miscible non-volatile organic solvent, particularly propylene glycol. Said nanoparticles can encapsulate or incorporate a product of interest for use in the agricultural, cosmetic, food or pharmaceutical fields.

18 Claims, 9 Drawing Sheets

(56) References Cited

U.S. PATENT DOCUMENTS

Figure 1:
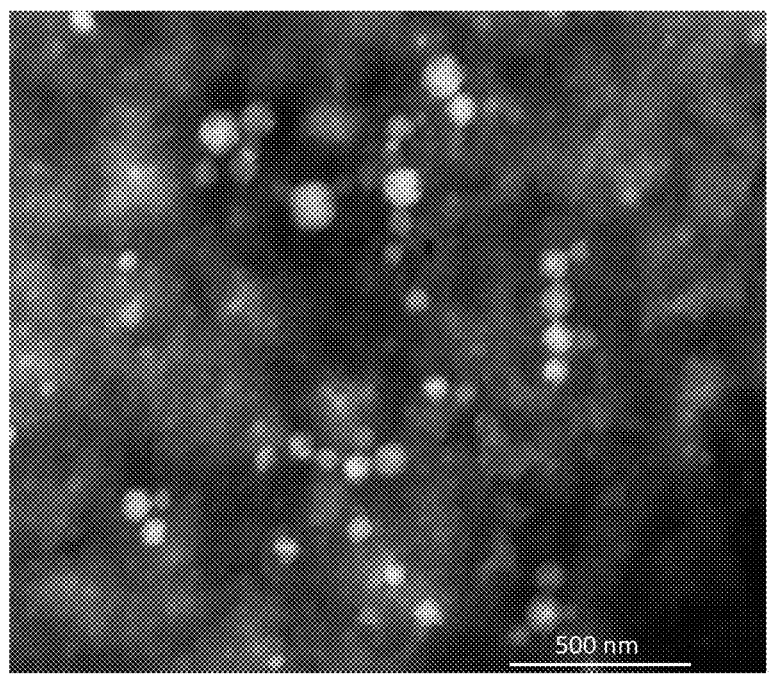

| | | | |
|---|---|---|---|
| 2007/0212419 A1* | 9/2007 | Bako | A61K 31/205 424/487 |
| 2009/0042284 A1 | 2/2009 | Tachibana et al. | |
| 2009/0074824 A1 | 3/2009 | Vila Pena et al. | |
| 2010/0166865 A1 | 7/2010 | Kumar et al. | |
| 2011/0091565 A1 | 4/2011 | Perumal et al. | |
| 2011/0305765 A1* | 12/2011 | Mathur | A61K 9/5161 424/491 |
| 2012/0195947 A1* | 8/2012 | Perumal | A61K 31/07 424/401 |
| 2013/0116261 A1 | 5/2013 | Agueros Bazo et al. | |

FOREIGN PATENT DOCUMENTS

| | | |
|---|---|---|
| EP | 2129684 B1 | 1/2011 |
| WO | 9106286 A1 | 5/1991 |
| WO | 9610992 A1 | 4/1996 |
| WO | 2007104732 A2 | 3/2006 |
| WO | 2008060734 A2 | 5/2008 |
| WO | 2009137112 A1 | 11/2009 |
| WO | 2010041203 A1 | 4/2010 |
| WO | 2012007628 A1 | 1/2012 |

OTHER PUBLICATIONS

Lawton, John W., et al.; "Zein: A History of Processing and Use," Cereal Chemistry, American Association of Cereal Chemists, 2002, pp. 1-18, vol. 79.

Zhong, Qixin, et al.; "Zein nanoparticles produced by liquid—liquid dispersion," Food Hydrocolloids, 2009, pp. 2380-2387, vol. 23.

Ramteke, Suman, et al.; "Clarithromycin Based Oral Sustained Release Nanoparticulate Drug Delivery System," Indian Journal of Pharmaceutical Sciences, 2006, pp. 479-484, vol. 68.

International Search Report, dated Jun. 28, 2013.

Zou, Tao, et al.; "Fabrication, characterization, and cytotoxicity evaluation of cranberry procyanidins-zein nanoparticles," Food Hydrocolloids, 2012, pp. 293-300, vol. 27.

Chen, Lingyun, et al.; "Elaboration and Characterization of Soy/Zein Protein Microspheres for Controlled Nutraceutical Delivery," Biomacromolecules, 2009, pp. 3327-3334, vol. 10.

Guo, H.X., et al.; "Stable aqueous film coatin dispersion of zein," Journal of Colloid and Interface Science, 2008, pp. 478-484, vol. 322.

Shewry, Peter R., et al.; "The prolamin storage proteins of cereal seeds: structure and evolution," Biochemical Journal, 1990, pp. 1-12, vol. 267.

Zhong, Qixin, et al.; "Application of Supercritical Anti-Solvent Technologies for the Synthesis of Delivery Systems of Bioactive Food Components," Food Biophysics, 2008, pp. 186-190, vol. 3.

Lai, L.F., et al.; "Preparation of new 5-fluorouracil-loaded zein nanoparticles for liver targeting," International Journal of Pharmaceutics, 2011, pp. 317-323, vol. 404.

Lin, Teng, et al.; "The Biodegradation of Zein In Vitro and In Vivo and its Application in Implants," American Association of Pharmaceutical Scientists PharmSciTech, 2011, pp. 172-176, vol. 12.

Muthuselvi, L., et al.; "Simple coacervates of zein to encapsulate Gitoxin," Colloids and Surfaces B: Biointerfaces, 2006, pp. 39-43, vol. 51.

Liu, Linshu, et al.; "Pectin/Zein Beads for Potential Colon-Specific Drug Delivery: Synthesis and in Vitro Evaluation," Drug Delivery, 2006, pp. 417-423, vol. 13.

Wang, Yi, et al.; "Formation of Zein Microphases in Ethanol-Water," Langmuir, 2010, pp. 12897-12901, vol. 26.

Chen, Lingyun, et al.; "In Vitro Study of the Release Properties of Soy-Zein Protein Microspheres with a Dynamic Artificial Digestive System," Journal of Agricultural and Food Chemistry, 2010, pp. 9861-9867, vol. 58.

De Sousa, Fabio Oliveira, et al.; "Effect of zein on biodegradable inserts for the delivery of tetracycline within periodontal pockets," Journal of Biomaterials Applications, 2011, pp. 187-200, vol. 27.

Parris, Nicholas, et al.; "Encapsulation of Essential Oils in Zein Nanospherical Particles," Journal of Agricultural and Food Chemistry, 2005, pp. 4788-4792, vol. 53.

Luo, Yangchao, et al.; "Preparation and characterization of zein/chitosan complex for encapsulation of α-tocopherol, and its in vitro controlled release study," Colloids and Surfaces B: Biointerfaces, 2011, pp. 145-152, vol. 85.

Podaralla, Satheesh, et al.; "Preparation of Zein Nanoparticles by pH Controlled Nanoprecipitation," Journal of Biomedical Nanotechnology, 2010, pp. 312-317, vol. 6.

Kumari, Avnesh, et al.; "Biodegradable polymeric nanopatricles based drug delivery systems," Colloids and Surfaces B: Biointerfaces, 2010, pp. 1-18, vol. 75.

Lai, T., et al.; "Clinical application of a novel sliver nanoparticles biosensor based on localized surface plasmon resonance for detecting the microalbuminuria," Acta biochimica et biophysica Sinica, 2010, pp. 787-792, vol. 42.

Santipanichwong, R., et al.; "Core-Shell Biopolymer Nanoparticles Produced by Electrostatic Deposition of Beet Pectin onto Heat-Denatured β-Lactoglobulin Aggregates," Journal of Food Science, 2008, pp. N23-N30, vol. 73.

Rejinold, N. Sanoj, et al.; "Curcumin-loaded biocompatible thermoresponsive polymeric nanoparticles for cancer drug delivery," Journal of Colloid and Interface Science, 2011, pp. 39-51, vol. 360.

Bourquin, Carole, et al.; "Delivery of Immunostimulatory RNA Oligonucleotides by Gelatin Nanoparticles Triggers an Efficient Antitumoral Response," Journal of Immunotherapy, 2010, pp. 935-944, vol. 33.

Tseng, Ching-Li, et al.; "Development of gelatin nanoparticles with biotinylated EGF conjugation for lung cancer targeting," Biomaterials, 2007, pp. 3996-4005, vol. 28.

Tan, Song Ting, et al.; "Biocompatible and Biodegradable Polymer Nanofibers Displaying Superparamagnetic Properties," Chemphyschem, 2005, pp. 1461-1465, vol. 6.

Rejinold, N. Sanoj, et al.; "Biocompatible, biodegradable and thermo-sensitive chitosan-g-poly (N-isopropylacrylamide) nanocarrier for curcumin drug delivery," International Journal of Biological Macromolecules, 2011, pp. 161-172, vol. 49.

Cho, H.S., et al.; "Biodegradability and biodegradation rate of poly(caprolactone)-starch blend and poly(butylene succinate) biodegradable polymer under aerobic and anaerobic environment," Waste Management, 2011, pp. 475-480, vol. 31.

Hu, Xiuli, et al.; "Biodegradable amphiphilic polymer-drug conjugate micelles," Expert Opinion on Drug Delivery, 2009, pp. 1079-1090, vol. 6.

Tang, Yu, et al.; "Biodegradable and biocompatible thermosensitive polymer based injectable implant for controlled release of protein," International Journal of Pharmaceutics, 2009, pp. 34-43, vol. 365.

Yu, N.Y., et al.; "Biodegradable poly(alpha-hydroxy acid) polymer scaffolds for bone tissue engineering," Journal of Biomedical Materials Research. Part B: Applied Biomaterials, 2010, pp. 285-295, vol. 93.

Kim, Hyung IL, et al.; "Biodegradable polymer films for releasing nanovehicles containing sirolimus," Drug Delivery, 2009, pp. 183-188, vol. 16.

Markvicheva, E.A., et al.; "Biodegradable polymer microparticles with entraped herbal extracts: preparation with supercritical carbon dioxide and use for tissue repair," Biomeditsinskaia khimiia, 2009, pp. 479-488, vol. 55; Including English Abstract.

Lawton, John W., et al.; "Zein: A History of Processing and Use," Cereal Chemistry, 2002, pp. 1-18, vol. 79.

Li, X.N., et al.; "Aqueous coating dispersion (pseudolatex) of zein improves formulation of sustained-release tablets containing very water-soluble drug," Journal of Colloids and Interface Science, 2010, pp. 46-53, vol. 345.

Salerno, Aurelio, et al.; "Design of novel three-phase PCL/TZ-HA biomaterials for use in bone regeneration applications," Journal of Materials Science. Materials in Medicine, 2010, pp. 2569-2581, vol. 21.

Zhong, Qixin, et al.; "Zein nanoparticles produced by liquid-liquid dispersion," Food Hydrocolloids, 2009, pp. 2380-2387, vol. 23.

(56) References Cited

OTHER PUBLICATIONS

Schaffazick, S.R., et al.; "Nanocapsules, nanoemulsion and nanodispersion containing melatonin: preparation, characterization and stability evaluation," Die Pharmazie, 2007, pp. 354-360, vol. 62; Abstract Only.

Rodriguez-Emmenegger, C., et al.; "Polymeric nanocapsules ultra stable in complex biological media," Colloids and Surfaces B: Biointerfaces, 2011, pp. 376-381, vol. 83.

Fukui, Yuuka, et al.; "The Preparation of Sugar Polymer-Coated Nanocapsules by the Layer-by-Layer Deposition on the Liposome," Langmuir, 2009, pp. 10020-10025, vol. 25.

Song, Rentao, et al.; "Sequence, Regulation, and Evolution of the Maize 22-kD α Zein Gene Family," Genome Research, 2001, pp. 1817-1825, vol. 11.

Esen, Asim, "Separation of Alcohol-Soluble Proteins (Zeins) from Maize into Three Fractions by Different Solubility," Plant Physiology, 1986, pp. 623-627, vol. 80.

Padua, Graciela W., et al.; "Controlled Self-Organization of Zein Nanostructures for Encapsulation of Food Ingredients," Micro/Nanoencapsulation of Active Food Ingredients, 2009, pp. 143-156, Chapter 9.

Arbos, P., et al.; "Quantification of the bioadhesive properties of protein-coated PVM/MA nanoparticles," International Journal of Pharmaceutics, 2002, pp. 129-136, vol. 242.

Salman, Hesham H., et al.; "Bioadhesive Mannosylated Nanoparticles for Oral Drug Delivery," Journal of Nanoscience and Nanotechnology, 2006, pp. 3203-3209, vol. 6.

Kakkar, Vandita, et al.; "Exploring solid lipid nanoparticles to enhance the oral bioavailability of curcumin," Molecular Nutrition and Food Research, 2011, pp. 495-503, vol. 55.

Meng, NA, et al.; "Controlled release and antibacterial activity chlorhexidine acetate (CA) intercalated in montmorillonite," International Journal of Pharmaceutics, 2009, pp. 45-49, vol. 382.

Peh, Kok Khiang, et al.; "Polymeric Films as Vehicle for Buccal Delivery; Swelling, Mechanical, and Bioadhesive Properties," Journal of Pharmacy & Pharmaceutical Sciences, 1999, pp. 53-61, vol. 2.

Evans, Cyril D., et al.; "Solvents for Zein: Primary Solvents," Industrial and Engineering Chemistry, 1941, pp. 1416-1417.

Taylor, Janet, "Preparation, characterisation and functionality of kafirin microparticles," Doctoral Thesis submitted to Department of Food Science, Faculty of Natural and Agricultural Sciences at University of Pretoria, South Africa, 2008, Parts I-IV.

O'Donnell, Patrick B., et al.; "Aqueous pseudolatex of zein for film coating of solid dosage forms," European Journal of Pharmaceutics and Biopharmaceutics, 1997, pp. 83-89, vol. 43.

Duclairoir, C., et al.; "Formulation of gliadin nanoparticles: Influence of the solubility of parameter of the protein solvent," Colloid and Polymer Science, 1998, pp. 321-327, vol. 276.

Chilean Office Action, dated Mar. 15, 2017, Chilean Application No. 201402145.

* cited by examiner

NANOPARTICLES COMPRISING A VEGETABLE HYDROPHOBIC PROTEIN AND A WATER MISCIBLE NON-VOLATILE ORGANIC SOLVENT AND USES THEREOF

CROSS-REFERENCE TO RELATED APPLICATIONS

This application is filed under the provisions of 35 U.S.C. § 371 and claims the priority of International Patent Application No. PCT/EP2013/052795 filed on 12 Feb. 2013 entitled "NANOPARTICLES COMPRISING A VEGETABLE HYDROPHOBIC PROTEIN AND A WATER MISCIBLE NON-VOLATILE ORGANIC SOLVENT AND USES THEREOF" in the name of Hesham H. A. SALMAN, et al., which claims priority to European Patent Application No. 12382049.0 filed on 13 Feb. 2012, both of which are hereby incorporated by reference herein in their entirety.

FIELD OF THE INVENTION

The invention relates to a biocompatible nanoparticulate delivery system comprising nanoparticles based on vegetable hydrophobic proteins, particularly zein, and water miscible non-volatile organic solvents having high mucosal bioadhesion capacity. The invention also relates to an in situ self-assembly method that allows the spontaneous formation of said nanoparticles and to the uses and applications thereof.

BACKGROUND OF THE INVENTION

Biodegradable nanoparticulate or microparticulate systems (polymeric particulate systems: PPS) constructed with biocompatible, biodegradable and non-toxic polymers have been used frequently as controlled release delivery vehicles in many industries [1-6]. There is a wide range of polymers that have been applied to obtain nanosystems, microsystems, films or implants, for example polyesters, polyanhydrides, proteins and polysaccharides, etc. [7-14].

One of the most relevant aspects related to polymeric particulate systems (PPS) production is the complexity of industrial scale up processes, which has been considered an important and critical factor for the commercialization of these systems. Many techniques have been developed to prepare PPS for the delivery of drugs such as emulsification or solvent evaporation techniques which involve the use of organic toxic volatile solvents (e.g., dichloromethane, ethyl acetate, chloroform, acetone, ethanol etc.), and applying special complex devices such as high shear homogenizers, supercritical fluid technology or spray dryers. The implementation of said techniques at large-scale production is still a challenge, as it requires defined steps which include process feasibility, formulation optimization, process optimization, scale-up and validation in order to develop quality products and provide a rational approach for production steps including drug concentration and polymer concentration, processing operations, particle size, drug stability or entrapment efficiency. In addition, to develop edible delivery systems suitable for food applications, regulations require that solvents and ingredients are either generally recognized as safe or listed by the Food and Drug Administration as processing aids.

Zein is a plant protein isolated from corn or maize belonging to a family of prolamines which are composed of high amounts of hydrophobic amino acids, such as proline, glutamine and asparagine. Zein is clear, odorless, non-toxic, biodegradable and water-insoluble vegetable protein. Zein has been investigated and used as a polymer in the pharmaceutical, medical, food, cosmetic, adhesive and packaging industries [15].

In the food and pharmaceutical industries, zein has been used, for example, to film-coat materials [16-17] and to form PPS for drug delivery strategies such as nanoparticles [18-20], microparticles [21-26] or polymer-based sustained-release implant drug delivery [27]. Various methods have been proposed to obtain zein particles. The majority of the methods applied to prepare particulate systems are based on the use of volatile organic solvents-aqueous solutions mixture such as ethanol or acetone-water systems to dissolve zein. Then, zein solution is added to other miscible solvent to precipitate zein (solvent displacement-evaporation method) forming colloidal particles. In this context, nanoparticles were prepared by the addition of a stock solution of zein dissolved in 85% ethanol to deionized water [28]. In a similar way, 5-fluorouracil-loaded zein nanoparticles for liver targeting were prepared by dissolving both 5-fluorouracil and zein in 70% ethanol (w/w) with the help of ultrasonic force. The resulting solution was immediately added to distilled water [29]. In a similar way, volatile oil containing nanocapsules were prepared from zein solution in 85% ethanol dispersed with high-speed mixing into 40 mL of water containing 0.01% of silicone fluid [20]. A supercritical anti-solvent process was applied to synthesize micro- and nanoparticles of zein for edible delivery systems of bioactive compounds [30].

U.S. Pat. No. 5,324,351 discloses a solvent mixture to dissolve zein comprising water and from about 60 to about 90 percent of a volatile organic solvent selected from the group consisting of ethanol, acetone and mixtures thereof. Then zein is precipitated by pouring said solution of zein as a stream into an aqueous phase under continuous mixing such that the zein precipitates as fine particles in a colloidal dispersion and finally the organic solvent is removed to obtain an aqueous dispersion comprising from about 0.1 to about 10 percent w/v of zein [31].

U.S. Patent Application 2011/0091565 discloses a method of producing non-immunogenic nanoparticles comprising a hydrophobic water-insoluble protein such as zein by dissolving said protein in a hydroalcoholic solvent (a mixture of ethanol and water) to provide a first aqueous phase solution. Then, a buffering agent is added to the first aqueous phase solution in the presence of a surfactant and a phospholipid to produce a second aqueous phase solution having a pH of between approximately pH 6.8 and approximately pH 7.4. After that, said second aqueous phase solution is processed to effect a reduction in diameter size of particles within the solution by ultrasonic shear, high pressure homogenization or a combination thereof, and finally the residual solvent is evaporated to produce nanoparticles having a diameter size of less than approximately 400 nm. Said method also requires the application of constant ultrasonic energy and a evaporation technique to eliminate the volatile solvent ethanol.

In all cases, the main drawback of the aforementioned methods to obtain zein nanoparticles is the need to apply some techniques to eliminate the volatile organic solvent, such as evaporation under reduced pressure, lyophilization or spray drying.

It is therefore necessary to develop a simple in situ self-assembly method that allows the spontaneous formation of nanoparticles constructed with biocompatible and biodegradable vegetable hydrophobic proteins, particularly zein, said method avoiding the use of volatile organic solvents or complex techniques such as high shear homogenization, supercritical fluid technology or spray dryers and allowing the effective encapsulation of molecules in cationic or anionic nanoparticles at large scale.

SUMMARY OF THE INVENTION

It has been now surprisingly found that mixing a pharmaceutically, cosmetically or food grade accepted water miscible non-volatile organic solvent such as a polyol (e.g., propylene glycol) or a solvent mixture of said water miscible non-volatile organic solvent and other water miscible non-volatile organic solvent such as glycerol or polyester as (Labrasol®: polyoxylglycerides or macrogolglycerides) containing a vegetable hydrophobic protein, particularly zein, with a vegetable hydrophobic protein non-solvent such as an aqueous solution that acts as zein non-solvent, optionally in the presence of excipients, allows the spontaneous formation of nanoparticles with a very homogeneous small size (about 120-500 nm) and high nanoparticles yield (about 98%). Examples show empty matrix nanospheres (Examples 1 and 2), loaded matrix nanospheres (Examples 3-8) and loaded core-shell vesicular nanocapsules (Examples 9-10) according to the invention showing said physico-chemical characteristics.

This method allows obtaining nanoparticles with high encapsulation efficiency of both large and small hydrophilic molecules (BSA, Rhodamine B, chlorhexidine, etc.) as well as hydrophobic molecules (curcumin, lipophilic fluorescent probe, etc) without the need of further volatile organic solvents (e.g., acetone, isopropanol, ethanol) or co-solvents (e.g., CDs) which are usually applied to obtain zein nanosystems. Specifically, Example 3 shows that the nanoparticles obtained by the in situ self-assembly method of the invention have an encapsulation efficiency of large hydrophilic molecules such as proteins that is 1.5 times higher than the nanoparticles obtained by a traditional method using volatile solvents. Example 4 also shows that the encapsulation efficiency for small hydrophilic molecules such as Rhodamine B is higher in the nanoparticles according to the invention compared to nanoparticles obtained by a traditional method.

Similar nanoparticles can be obtained from binary solvent systems for zein (see Example 2). The use of water miscible non-volatile binary organic solvents mixtures that are non-toxic or food grade listed materials make them attractive for incorporation of different types of molecules for further encapsulation in zein for different industries and applications.

In addition, the manufacturing method of this invention also allows forming in situ self-assembled cationic nanoparticles (ZSNP) and nanocapsules (ZSNC) in a body fluid once the solution, suspension or emulsion containing zein in a water miscible non-volatile organic solvent and a product of interest (POI) is mixed with said fluid; consequently, POI-loaded nanoparticles can be in situ spontaneously formed in contact with the body fluid (an aqueous medium).

On the other hand, this invention allows obtaining anionic zein based PPS by successfully coating the nanoparticles with polyanions. Example 1 shows empty matrix nanospheres coated or complexed with arabic gum to produce anionic nanoparticles having a high yield. Examples 9 and 10 show core-shell nanocapsules loaded with an essential oil that are coated or contain arabic gum and having an encapsulation efficiency of 75-84%.

Other important advantage of this method is related to the simplicity of the process for the manufacture of nanoparticles since the method of this invention facilitates the industrial scale production without the use of any special apparatus, high shear homogenizers, sonication techniques or evaporation of volatile organic solvents such as ethanol or acetone. The nanoparticles obtained can be easily incorporated in many dosage forms such as solutions, suspensions, gels and semi-solids or solid ones which are widely used in cosmetic, pharmaceutical, agriculture or food industry. In this context, it has been observed that the scale up process of the manufacturing method of this invention, patches from 1 L to 50 L did not affect the physicochemical properties of the obtained zein nanosystems as is shown in Example 1.

Furthermore, due to the different matrix characteristics of the nanoparticles of the invention, said nanoparticles show an enhancement in the release of the encapsulated hydrophilic molecules compared to the nanoparticles obtained by a traditional method, both when simulated intestinal fluid or simulated saliva fluid is used as is shown in Examples 4 and 8, respectively. Specifically, the nanoparticles of the invention increase the release of encapsulated hydrophilic molecules about 1.4 and 2 times compared to nanoparticles obtained by traditional methods.

Furthermore, the nanoparticles of the invention display a high bioadhesive affinity to porcine buccal mucosa model surfaces higher than that observed for other nanoparticles obtained by a traditional method using volatile organic solvents. Said bioadhesion guarantees an effective enhancement of the controlled release of a product of interest. Specifically, Example 8 shows that the bioadhesive capacity of the different nanoparticle formulations of the invention is about 2-4 times higher than the bioadhesive capacity of the nanoparticles prepared by traditional methods using ethanol.

Summing up, the zein nanoparticles obtained by the in situ spontaneous self-assembly technique of the invention show, among others, the following properties: (i) homogenous size distribution at small and large scale; (ii) the use of non-volatile organic solvents such as propylene glycol, allows the formation of matrix nanospheres and core-shell vesicular nanocapsules containing oil without the need of evaporation of volatile organic solvents; (iii) high efficacy to encapsulate hydrophilic, hydrophobic molecules and oils without the need of co-solvents or complexing agents; (iv) this nanoparticle manufacturing method also allows forming in situ self-assembled nanoparticles (ZSNP) in a body fluid once the solution containing zein in a water miscible non-volatile organic solvent and a product of interest (POI) is mixed with said fluid (i.e., by subcutaneous injection or oral administration); (v) higher bioadhesive affinity to mucosal surfaces compared to zein nanoparticles prepared by a traditional method, (vi) high facility to be incorporated in many dosage forms, for example, liquid, solids or semi-solids, such as suspensions, gels, etc., and (vii) higher release of the encapsulated product in biological fluids compared to zein nanoparticles prepared by a traditional method. All of the above mentioned properties favour the use of said nanoparticles in different fields, such as in the agricultural, food, etc., fields, specially, in the cosmetic and pharmaceutical fields, as controlled release delivery systems to different surfaces including, among others, hair, skin, etc., or their administration by buccal, nasal, oral, rectal, vaginal, transdermal or parenteral routes, among others.

Therefore, it is an object of the present invention the production and uses of nanoparticles based on a vegetable hydrophobic protein and a water miscible non-volatile organic solvent.

Thus, in an aspect, the invention relates to a nanoparticle selected from the group consisting of:

a) a matrix nanosphere, wherein said matrix nanosphere comprises a matrix, said matrix comprising a vegetable hydrophobic protein and at least a water miscible non-volatile organic solvent; and b) a core-shell vesicular nanocapsule, wherein said core-shell vesicular nanocapsule comprises a core and a shell, said shell comprising a vegetable hydrophobic protein and at least a water miscible non-volatile organic solvent.

In another aspect, the invention relates to a process for producing a nanoparticle wherein said nanoparticle is a matrix nanosphere comprising a matrix, said matrix comprising a vegetable hydrophobic protein and at least a water miscible non-volatile organic solvent, said process comprising contacting a solution of the vegetable hydrophobic protein in at least a water miscible non-volatile organic solvent with a vegetable hydrophobic protein non solvent such as an aqueous medium in order to form said nanoparticle and wherein the solution of the vegetable hydrophobic protein does not comprise a volatile organic solvent.

In another aspect, the invention relates to a process for producing a nanoparticle selected from the group consisting of:
(a) a matrix nanosphere comprising a product of interest, wherein said matrix nanosphere comprises a matrix, said matrix comprising a vegetable hydrophobic protein and at least a water miscible non-volatile organic solvent; and
(b) a core-shell vesicular nanocapsule comprising a product of interest, wherein said core-shell vesicular nanocapsule comprises a core and a shell, said shell comprising a vegetable hydrophobic protein and at least a water miscible non-volatile organic solvent, said process comprising contacting a solution, suspension or emulsion comprising the vegetable hydrophobic protein and the product of interest in at least a water miscible non-volatile organic solvent with a vegetable hydrophobic protein non-solvent such as an aqueous medium in order to form said nanoparticle and wherein the solution, suspension or emulsion comprising the vegetable hydrophobic protein and the product of interest does not comprise a volatile organic solvent.

In another aspect, the invention relates to a nanoparticle obtainable by the process of the invention.

In another aspect, the invention relates to a solution containing a vegetable hydrophobic protein in a medium, said medium comprising at least a water miscible non-volatile organic solvent and, optionally, an aqueous medium, wherein the amount of aqueous medium is lower than the necessary amount of aqueous medium to form nanoparticles, wherein the medium comprising at least a water miscible non-volatile organic solvent does not comprise a volatile organic solvent and wherein the amount of vegetable hydrophobic protein is comprised between 0.01% and 50% (w/v) with the proviso that when the vegetable hydrophobic protein is gliadin, then the amount of vegetable hydrophobic protein is higher than 0.1%.

In another aspect, the invention relates to a solution, suspension or emulsion containing a vegetable hydrophobic protein and a product of interest dissolved, suspended or emulsified in a medium, said medium comprising at least a water miscible non-volatile organic solvent and, optionally, a surfactant, and, optionally, an aqueous medium, wherein the amount of aqueous medium is lower than the necessary amount of aqueous medium to form nanoparticles, wherein the medium comprising at least a water miscible non-volatile organic solvent does not comprise a volatile organic solvent and wherein the amount of vegetable hydrophobic protein is comprised between 0.01% and 50% (w/v).

In a particular embodiment, said nanoparticle provided by the present invention, or said solution provided by the present invention, further comprises a product of interest, e.g., a product of interest in the agriculture, cosmetics, food, or pharmacy industries.

In another aspect, the invention relates to a suspension of nanoparticles according to the invention in a medium, said medium comprising at least a water miscible non-volatile organic solvent and a vegetable hydrophobic protein non-solvent such as an aqueous medium, and not comprising a volatile organic solvent.

In another aspect, the invention relates to a composition comprising at least one nanoparticle or a solution, suspension or emulsion provided by the present invention, and a carrier.

In another aspect, the invention relates to a foodstuff comprising a nanoparticle provided by this invention.

In another aspect, the invention relates to a nanoparticle according to the invention wherein the product of interest is the antioxidant curcumin for use as a food additive, or wherein the product of interest is the antimicrobial drug chlorhexidine for use in the treatment and/or prevention of a buccal or external body infection, or wherein the product of interest is an oil selected from cod liver oil and linolenic acid for use as dietary supplement.

BRIEF DESCRIPTION OF THE DRAWINGS

FIG. 1. Photography of self-assembled zein nanoparticles (ZSNP-10) obtained by Transmission Electron Microscopy (TEM).

FIG. 2. Solubility of zein in binary mixtures of different solvents with propylene glycol (PG) as primary solvent. End point range (represented by the starting point of % turbidity increase to 100% increase) indicates the percentage of solvent (v/v) in PG at witch zein starts to precipitate until achieving total zein precipitation which is represented by 100% of turbidity change (point at which no precipitation can occur). The arrows indicate, as example, the percentage (v/v) of Tween® 80 in PG solution containing zein at which the precipitation of zein started until achieving complete precipitation.

FIG. 3. Accumulative percentage of Rhodamine B (RB) released from the nanoparticle formulations, after the incubation of RB-self assembled zein nanoparticles prepared from different zein solvents including propylene glycol (RB-ZSNP-PG), propylene glycol:glycerol mixture (RB-ZSNP-PG:G) and propylene glycol:Lutrol® L 44 mixture (RB-ZSNP-PG:Lut); and RB-zein nanoparticles prepared by traditional method (RB-Traditional NP) in simulated gastric fluid (SGF) and simulated intestinal fluid (SIF) for different time intervals.

FIG. 4. Accumulative percentage of Rhodamine B (RB) released from the nanoparticles formulations after the incubation of RB-self assembled zein nanoparticles prepared from different zein solvents including propylene glycol (RB-ZSNP-PG), propylene glycol:glycerol mixture (RB-ZSNP-PG:G) and propylene glycol:Lutrol® L 44 mixture (RB-ZSNP-PG:Lut); and RB-zein nanoparticles prepared by traditional method (RB-Traditional NP) in simulated saliva fluid.

FIG. 5. Assay of the adhered amount (mg/$cm^2$) of nanoparticles formulations in porcine buccal mucosal tissue at different times. The fluorescently labeled RB-self assembled zein nanoparticle formulations weren prepared from different zein solvents including propylene glycol alone (RB-ZSNP-PG), Propylene glycol:glycerol mixture (RB-ZSNP-PG:G) and propylene glycol:Lutrol® L 44 mixture (RB-ZSNP-PG:Lut), and the conventional fluorescently labeled zein nanoparticles (RB-ZNP-T) prepared by traditional solvent evaporation method. Each value was represented by the mean (n=3; in all cases, SD was less than 20% of the mean).

Figure 6:
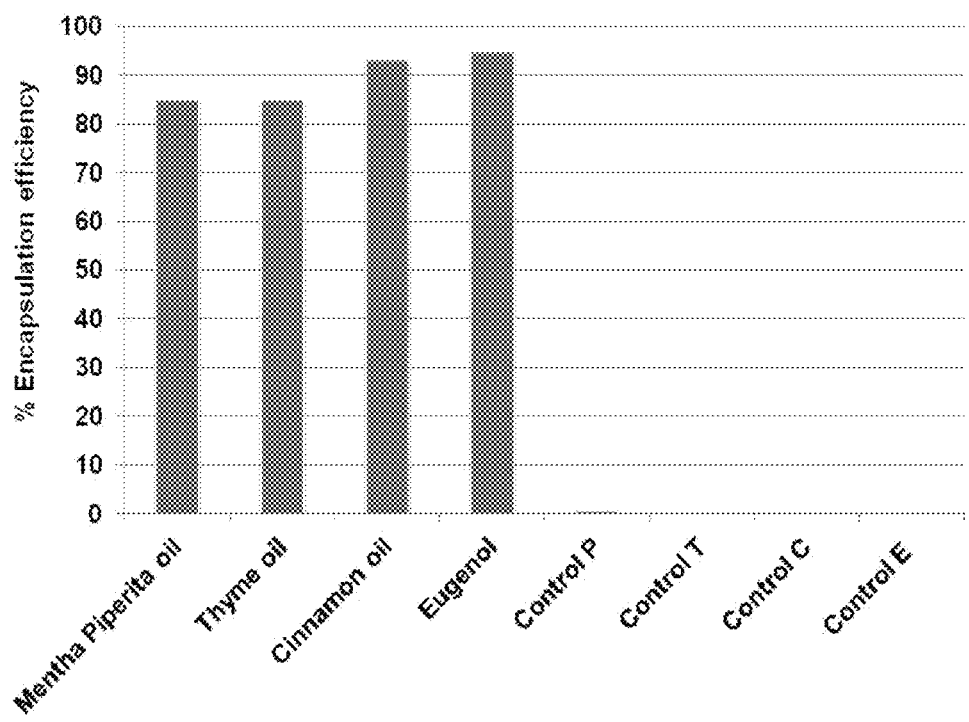

FIG. 6. Encapsulation efficiencies of different essential oils in self-assembled zein nanoparticles (ZSNC) and in control formulations prepared from the same oils and propylene glycol (PG) solutions without zein. Controls P, T, C and E are *Mentha piperita*, Thyme, Cinnamon and Eugenol oil controls, respectively.

Figure 7:
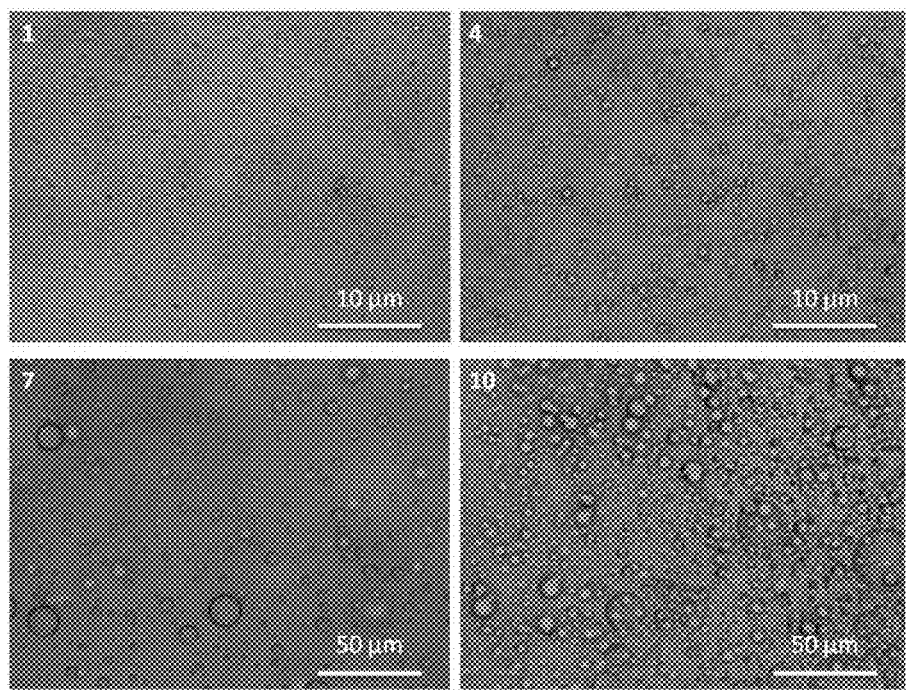

FIG. 7. Photographies of samples 1, 4, 7 and 10 selected from Table 11 as illustrative examples and obtained by light microscopy.

Figure 8:
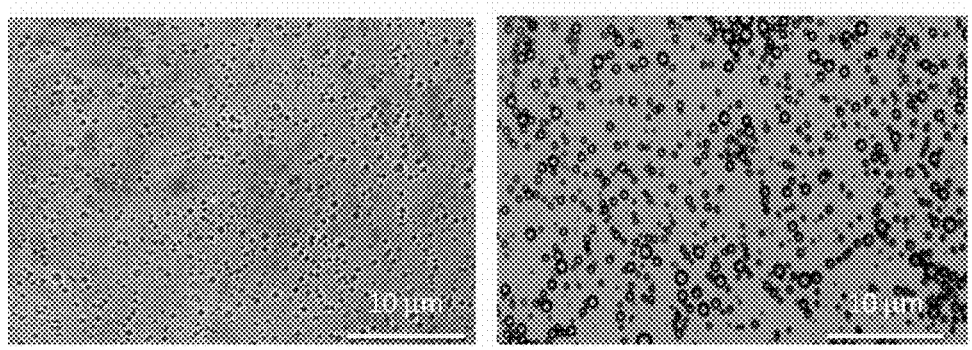

FIG. 8. Photographies of cationic self-assembled zein nanoparticles (ZSNC-L1) and cationic self-assembled zein microparticles (ZSMC-L1) loaded with lemon oil obtained by light microscopy.

Figure 9:
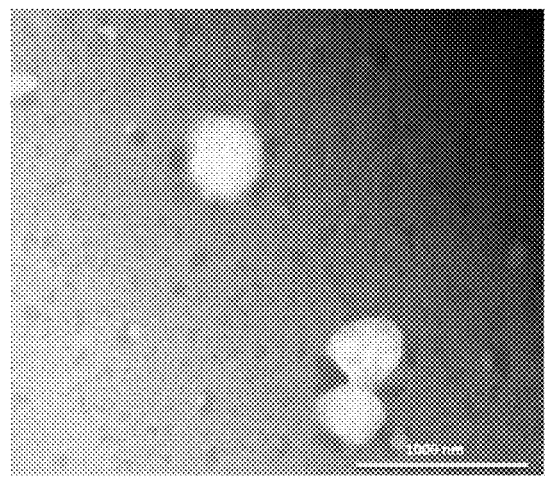

FIG. 9. Transmission electron microscopy (TEM) for cationic self-assembled zein nanoparticles loaded with lemon oil (ZSNC-L1).

DETAILED DESCRIPTION OF THE INVENTION

The present invention provides cationic and anionic nanoparticles, specifically matrix nanospheres and core-shell vesicular nanocapsules, obtained by a self-assembly technology based on a vegetable hydrophobic protein, particularly zein, and a water miscible non-volatile organic solvent. The present invention also provides methods for producing said nanoparticles, and applications of said nanoparticles.

Definitions

In order to facilitate the comprehension of the present invention, the meaning of some terms and expressions as used in the context of the invention are set forth below.

As used herein, the term "vegetable hydrophobic protein" relates to a protein usually found in vegetables which is composed of high amounts of hydrophobic amino acids such as, for example, proline, glutamine and asparagine. These hydrophobic amino acids make the protein water-insoluble in its non-denatured state. The vegetable hydrophobic protein of the invention is a protein considered as practically insoluble by the British Pharmacopoeia (BP) (i.e. requiring more than 10.000 parts of solvent (mL) for one part of solute (g) at a temperature ranging between 15° C. and 25° C.). Said vegetable hydrophobic protein may be a protein directly obtained from the vegetable source or obtained by genetic engineering techniques. A particular type of vegetable hydrophobic protein is the family of prolamines. The prolamines may be found in various grains such as corn, wheat, barley, millet, rice and sorghum. Some examples of suitable prolamines to be used in this invention are zein, gliadin, hordein and kafirin, although the application of the method of this invention is not necessarily limited to these examples. Particularly, zein was used in this invention as a model of vegetable hydrophobic protein derived from corn gluten meal, a co-product of corn, and is a mixture of at least four types of proteins: α-, β-, γ-, and δ-zein, each with a different amino acid sequence, molecular weight, and solubility.

"Average size" or "mean size", as used herein, relates to the average diameter of a population of nanoparticles moving together in an aqueous medium. The average size of these systems can be measured by standard processes known by persons skilled in the art and which are described, by way of illustration, in the experimental part attached to the examples described below. The average size of the particles can be mainly affected by the amount of the vegetable hydrophobic protein, and by the nature and amount of the product of interest (if any), present in the nanoparticles of the invention (generally, the larger the amount of said components, the larger the average size of the nanoparticles), and by some parameters such as the viscosity, concentration of the vegetable hydrophobic protein and the presence of other solvents or surfactants, etc.

"Average Zeta Potential" or "mean Zeta Potential", as used herein, relates to the average surface charge of a population of nanoparticles moving together in an aqueous medium. The average Zeta potential of these systems can be measured by standard processes known by persons skilled in the art and which are described, by way of illustration, in the experimental part attached to the examples described below. The average Zeta potential of the particles can be mainly affected by the nature and amount of the product of interest (if any), present in the nanoparticles of the invention. Generally, the average Zeta potential of the nanoparticles will be more negative by the addition of anionic molecules or polymers or pH changes to said components, and by some parameters or by the presence of other solvents or surfactants, etc.

As used herein, the term "nanoparticle" refers to a colloidal system of a solid particle with an average size less than 1 micrometer (μm), typically between 1 and 999 nanometers (nm), preferably between 50 and 500 nm, more preferably between 100 and 400 nm, still more preferably between 120 and 200 nm, still more preferably between 120 and 160 nm approximately, formed by a vegetable hydrophobic protein and including a water miscible non-volatile organic solvent in its composition. Depending, among other facts, on their manufacture method, nanoparticles can be subdivided into matrix nanospheres and "core-shell vesicular nanocapsules" [32-34]. "Matrix nanospheres" are matrix forms formed by a three dimensional network; when a nanosphere is loaded with a product of interest, e.g., a drug, said product of interest can be physically and uniformly dispersed in said three dimensional network. The matrix or three dimensional network of the matrix nanospheres of the invention contains a vegetable hydrophobic protein and one or more water miscible non-volatile organic solvents. "Core-shell vesicular nanocapsules" are vesicular systems formed by an inner cavity (known as the "core") which contains the product of interest surrounded by a wall or membrane (known as the "shell"), i.e., the core-shell vesicular nanocapsules of the invention are nano-vesicular systems that exhibit a typical core-shell structure in which the product of interest is confined to a reservoir or within a cavity ("core") surrounded by a vegetable hydrophobic protein wall or membrane ("shell") that also contains one or more water miscible non-volatile organic solvents. The skilled in the art knows that the core of the core-shell vesicular nanocapsule may contain only excipients, may contain any product of interest as defined hereinafter (for example a compound having agricultural, cosmetic, food or pharmaceutical activity or mixtures thereof with or without excipients), or may contain both excipients and said product of interest as defined hereinafter.

In both cases, due to the large specific surface of these systems, the molecules of the product of interest may be trapped or adsorbed in the surface of the nanoparticles.

As it is used herein, a "product of interest" or "POI" refers to any compound susceptible of being used in any type of industry, for example, in the agricultural, cosmetic, food, or pharmaceutical industries. Practically any compound susceptible of being used in any type of industry can be considered a POI in accordance with the present invention. Illustrative, non-limiting examples of POI according to the present invention include small or large, water-soluble or lipid-soluble, hydrophilic, hydrophobic or amphiphilic, organic or inorganic, compounds, such as lipids, nucleosides, nucleotides, oils, fatty acids, oligonucleotides, peptides, polynucleotides, proteins, small organic chemical compounds, etc. The POI may be in any form or state, for example, in liquid, semisolid or solid state, i.e., the POI may be dissolved, dispersed or immiscible (in case of emulsions) in aqueous or organic mediums, thus forming an aqueous or organic solution or suspension, including oily solutions or emulsions, or, alternatively, the POI may be undissolved or undispersed, as a solid product. The POI may contain other POI or more that may be dissolved, dispersed or emulsified in the first POI.

In a particular embodiment, the POI is a complete or fractionated microorganism such as a virus, bacteria or yeast or a mixture thereof dispersed in a solution, suspension or emulsion. In a more particular embodiment the microorganism is a probiotic, particularly probiotic bacteria. Examples of probiotic bacteria are, without limitation, *lactobacillus* and bifidobacteria.

In a particular embodiment, the POI is a compound having agricultural activity, i.e., susceptible of being used in the agricultural industry, for example, a phytosanitary product for controlling pests and pathogens, a plant growth promoting agent, for example, an herbicide (e.g., glyphosate, etc.), an insecticide (e.g., lambda-cyhalothrin, etc.), a fungicide (e.g., Mancozeb or essential oils), or a anti-transpirant, etc.

In another particular embodiment, the POI is a compound having cosmetic activity, i.e., a substance used to enhance the appearance or odor of the human or animal body. Cosmetics include skin-care creams, lotions, powders, perfumes, lipsticks, fingernail and toe nail polish, eye and facial makeup, towelettes, permanent waves, colored contact lenses, hair colors, hair sprays and gels, deodorants, hand sanitizer, baby products, bath oils, bubble baths, bath salts, butters and many other types of products. Illustrative, non-limitative, examples of POI used in the cosmetic industry include antiaging products (e.g., retinoids), anti-acne products (e.g., erythromycin, benzoyl peroxide, etc.), facial care products (e.g., GHK copper in facial cleansers, etc.), pigmented cosmetics (e.g., color pigments used in rouges, foundations, cover-up, powder, etc.), cosmeticals (e.g., Co-Q10, etc.), personal care products (e.g., moisture-controlled release of fragrance in deodorants, etc.), products for sunscreen/suncare (e.g., UV-blockers), products for toothcleaners, toothpastes, or rinses (e.g., sustained release of triclosan/bactericides, flavors, scents, anti-dry mouth actives in mouth, etc.), products for shampoo (e.g., anti-dandruff/moisturizing actives, etc.), perfumes (e.g., scent particles, etc.), hair products (e.g., fixatives, volumetric hair styling products, etc.), etc.

In another particular embodiment, the POI is a compound having nutritional activity, i.e., susceptible of being used in the food industry, for example, folic acid, 4-aminobenzoic acid, niacin or vitamin B3, pantothenic acid or vitamin B5, thiamine monophosphate, thiamine pyrophosphate, thiamine triphosphate, ascorbic acid, pteroylpolyglutamic acids, folinic acid, nicotinic acid, hyaluronic acid, thioctic acid, coumaric acid, caffeic acid, vitamins of the A, D, E, K families and derivatives thereof, phospholipids, carotenoids (e.g., carotenes, lycopene, lutein, capsanthin, zeaxanthin, etc.), fatty acids, omega-3 fatty acids (e.g., DHA, EPA, etc.), amino acids (e.g., isoleucine, leucine, methionine, phenylalanine, tryptophan, and valine), phytostanols or phytosterols (e.g., sitosterol, campesterol, stigmasterol, etc.), polyphenols (phenolic acids, stilbenes, flavonoids, —anthocyanins, flavonols, flavanols, flavanones, chalcones, isoflavones, etc.—, lignans, etc; e.g., quercetin, rutin, resveratrol, kaempferol, myricetin, isorhamnetin, luteolin, catechin, condensed tannins, malvidin, cyanidin, delphinidin, peonidin, gallic acid, cumaric acid, cafeic acid, etc.), derivatives of food products such as yeast and yeast components, wine components, cheese components, microorganisms and microorganisms components, food aromas, etc. A product is said to be "food-grade" when its use in human or animal food is safe according to the Codex Alimentarius of a country or of an organization, for example, the Food and Agriculture Organization (FAO) of the United Nations or the World Health Organization (WHO); consequently, a "food-grade" product is a non-toxic product "suitable for use thereof in food" and therefore both expressions are synonyms and are indistinctly used in this description.

In another particular embodiment, the POI is a compound having therapeutical activity (i.e., a substance which, when administered to a subject, interacts with its receptor in the action site and exerts a certain effect); this kind of products are susceptible of being used in the pharmaceutical industry. Illustrative, non-limitative, examples of POI having therapeutical activity include antibodies or fragments thereof, bacterial, fungal or viral proteins or antigens, cell receptors, coagulation factors, cytokines, enzymes, erythropoietins, growth factors, hormones, insulins, interleukins, interferons, ligands, nucleic acids (e.g., nucleotides, oligonucleotides, polyneucleotides, DNA, RNA, etc.), signal transducing agents, small organic chemical compounds, toxins, etc. In a particular embodiment, the POI includes analgesic (narcotic) agents (e.g., codeine, morphine, etc.), analgesic (non-narcotic) agents (e.g., acetylsalicylic acid, flufenamic acid, etc.), antialopecia agents (e.g., finasteride, minoxidil, etc.), antianginal agents (e.g., atenolol, nicardipine, etc.), antibacterial agents (e.g., amoxicillin, ampicillin, azythromycin, cefaclor, ciprofloxacin, neomycin, tetracycline, etc.), antidepressant agents (e.g., fluoxetine, paroxetine, etc.), antifungal agents (e.g., isoconazole, ketoconazole, etc.), antihypertensive agents (e.g., benazepril, captopril, carvedilol, enalapril, losartan, minoxidil, etc.), antiinflammatoy agents (e.g., niflumic acid, celecoxib, ibuprofen, etc.), antineoplastic agents (e.g., alemtuzumab, cisplatin, docetaxel, trastuzumab, etc.), antipyretic agents (e.g., acetaminophen, indomethacin, etc.), antipsycothic agents (e.g., risperidone, etc.), anxiolytic agents (e.g., alprazolam, lorazepam, etc.), bronchodilator agents (e.g., carbuterol, epinephrine, etc.), glucocorticoids (e.g., budesonide, prednisolone, etc.), immunosuppressant agents (e.g., alemtuzumab, tacrolimus, etc.), etc. In a further particular embodiment, said POI is selected from the group consisting of acetylsalicylic acid, alpha-atrial natriuretic peptide, arginine vasopressin, atropine, augmerosen, atorvastatin, avastin, calcitonins, chorionic gonadotropins, corticotropin, desmopressin, epibatidine, erbitux, exenatide, herceptin, humira, humulin, ketoconazole, lanreotide, lutropin alpha, metoprolol, minoxidil, nesiritide, octreotide, paclitaxel, paracetamol, pegaptanib, recombinant follicle stimulating hormone, recombinant growth factors, remicade, rituxan, sermorelin, somatotropin, taxane derivatives, taxol, teriparatide acetate, thyrotropin, triclosan, urofollitropin, xolair, etc. In another embodiment, the POI is selected from the group consisting of actinomycin D, albendazole, aldosterone, alprazolam, amiodarone, amitriptyline, amprenavir, asimadoline, atorvastatin, bunitrolol, buspirone, camptothecin, carbamazepine, carvedilol, celiprolol, cyclosporine A, cimetidine, clotrimazole, colchicine, cortisone, daunorubicin, debrisoquine, dexamethasone, diazepam, digitoxin, digoxin, diltiazem, docetaxel, domperidone, doxorubicin, efavirenz, epirubicin, erythromycin, ergotamine, estradiol, estradiol glucuronide, erlotinib, etoposide, phenyloin, fentanyl, felodipine, phenothiazines, fexofenadine, fluoroquinolones, fluorouracil, FK-506, gentamicin, griseofulvin, hydrocortisone, imatinib, indinavir, itraconazole, ivermectin, ketoconazole, kaempferol, levofloxacin, lidocaine, loperamide, losartan, lovastatin, mebendazole, methylprednisolone, methotrexate, mibefradil, midazolam, nisoldipine, morphine, nelfinavir, nicardipine, nitrendipine, nifedipine, ondansetron, paclitaxel, pentazocine, praziquantel, prednisolone, prednisone, quercetin, quinidine, ranitidine, rapamycin, rifabutin, rifampicin, ritonavir, saquinavir, sirolimus, sulfamethizole, tacrolimus, tamoxifen, talinolol, teniposide, terfenadine, tetracycline, topotecan, triamcinolone, valspodar, verapamil, vinblastine, vincristine, vindesine, zopiclone, and mixtures thereof.

In another particular embodiment, the POI is an excipient, i.e. a water immiscible or insoluble inactive substance that can be liquid, solid or semisolid, used as a medium or carrier for the active ingredients of a composition. Illustrative, non-limitative examples of POI acting as an excipient are liquid paraffin or melted lipids such as wax, cotton oil, corn oil, hydrogenated vegetable oil, canola oil, coconut oil, etc. Said POIs are particularly useful in the production of core-shell vesicular nanocapsules and they may be found in the core of said nanocapsules.

In a preferred embodiment, the POI is selected from the group consisting of an herbicide, an insecticide, a fungicide, an anti-aging product, an anti-acne product, a facial care product, a pigmented cosmetic, a cosmetical, a personal care product, a product for sunscreen/suncare, a product for tooth-cleaners, toothpastes, or rinses, a product for shampooes, a perfume, a hair product, a food additive, an essential oil, *Mentha piperita* oil, Thyme oil, cinnamon oil, eugenol, lemon oil, curcumin, folic acid, 4-aminobenzoic acid, niacin or vitamin B3, pantothenic acid or vitamin B5, thiamine monophosphate, thiamine pyrophosphate, thiamine triphosphate, ascorbic acid, pteroylpolyglutamic acids, folinic acid, nicotinic acid, hyaluronic acid, thioctic acid, p-coumaric acid, caffeic acid, a vitamin of the A, D, E, K families and derivatives thereof, a phospholipid, a carotenoid, a fatty acid, an omega-3 fatty acid, cod liver oil, linolenic acid, an amino acid, a phytostanol, a phytosterol, a polyphenol, chlorhexidine, bovine serum albumin, an analgesic agent, an antialopecia agent, an antianginal agent, an antibacterial agent, an antidepressant agent, an antifungal agent, an antihypertensive agent, an antiinflammatoy agent, an antineoplastic agent, an antipyretic agent, an antipsycothic agent, an anxiolytic agent, a bronchodilator agent, a glucocorticoid, an immunosuppressant agent, or any combination thereof.

A "volatile organic solvent", as used herein, is a liquid organic compound that vaporizes/evaporates easily at room temperature; a volatile organic solvent usually has high vapour pressure and a lower boiling point compared to water (i.e., a volatile organic solvent has a vapour pressure higher than 23.3 hPa at 20° C. and a boiling point lower than 100° C.). Illustrative, non limitative examples of volatile organic solvents are USP grade ethanol (initial boiling point and boiling range 78.0-80.0° C. and vapour pressure 59.5 hPa at 20° C.), methanol (boiling point 64.7° C. and vapour pressure 130.3 hPa at 20° C.) and acetone (boiling point 56° C. and vapour pressure 245.3 hPa at 20° C.).

Similarly, a "non-volatile organic solvent", as used herein, refers to a liquid organic compound that does not evaporate easily or evaporates very slowly at room temperature with lower vapour pressure and higher boiling point compared to water. Illustrative, non limitative, examples of non-volatile organic solvents are USP grade glycols such as propylene glycol (boiling point 187° C. and vapour pressure 0.11 hPa at 20° C.), polyglycols such as liquid poly(ethylene glycol) with average molecular weight 400 g/mole (boiling point 250° C. and vapour pressure <0.01 hPa at 20° C.) or polyols such as glycerol (boiling point 290° C. and vapour pressure <0.01 hPa at 20° C.). When only one non-volatile organic solvent is used in the context of the present invention, said solvent must be a primary solvent in which the vegetable hydrophobic protein is dissolved. Thus, said non-volatile organic solvent may be different depending on the vegetable hydrophobic protein used. When a mixture of different non-volatile organic solvents is used, at least one of said solvents must be a primary solvent. The other solvents forming part of a mixture may be different primary solvents or secondary solvents. Depending on the number of solvents used the mixture may be binary when using two solvents, or ternary when using a three solvent mixture.

A "water miscible" solvent or liquid, is a solvent or liquid that dissolves completely in water and is difficult to separate from water, e.g., glycerol, propylene glycol, etc.

As used herein, the term "vegetable hydrophobic protein non-solvent" is a solvent in liquid, semisolid or solid state, that dissolves or that is miscible with the non-volatile organic solvent used but cause the partial or total precipitation of the vegetable hydrophobic protein. In a preferred embodiment the vegetable hydrophobic protein non-solvent is an aqueous medium. In another embodiment the vegetable hydrophobic protein non-solvent is glycerol. In another embodiment the vegetable hydrophobic protein non-solvent is Labrasol®. In another embodiment the vegetable hydrophobic protein non-solvent is Lutrol®

As used herein, the term "aqueous medium" is a medium comprising water or a medium consisting of water. Said aqueous medium may comprise water and a water miscible solvent. In a particular embodiment the aqueous medium is a biological fluid.

As used herein, the term "biocompatible" means that the nanoparticle produced by the method of the invention does not cause or elicit significant adverse effects when administered in vivo to a subject. Examples of possible adverse effects include, but are not limited to, excessive inflammation and/or an excessive or adverse immune response, as well as toxicity.

As used herein, the term "polyol" or "polyols", refers to compounds with multiple hydroxyl functional groups available for organic reactions. A molecule with two hydroxyl groups is a diol, one with three is a triol, one with four is a tetrol and so on. Examples of polyols useful in the present invention are, among others, glycerol (also named glycerin or glycerine) which is a simple polyol compound, and glycols such as propylene glycol (PG) (also called 1,2-propanediol or propane-1,2-diol).

As used herein, the term "traditional method", refers to a method for the manufacture of nanoparticles pertaining to a group of methods that have in common the use of a volatile organic solvent, specially ethanol-water mixtures.

Nanoparticles of the Invention In an aspect, the invention relates to a nanoparticle, hereinafter referred to as the "nanoparticle of the invention", selected from the group consisting of:
- a) a matrix nanosphere, wherein said matrix nanosphere comprises a matrix, said matrix comprising a vegetable hydrophobic protein and at least a water miscible non-volatile organic solvent; and
- b) a core-shell vesicular nanocapsule, wherein said core-shell vesicular nanocapsule comprises a core and a shell, said shell comprising a vegetable hydrophobic protein and at least a water miscible non-volatile organic solvent.

The term "nanoparticle" has been previously defined and refers to a colloidal system of a solid particle with an average size less than 1 μm, typically between 1 and 999 nm, preferably between 100 and 400 nm, more preferably between 120 and 160 nm, still more preferably around 130-140 nm, formed, in this particular case by a vegetable hydrophobic protein and at least a water miscible non-volatile organic solvent of said protein. The term "nanoparticle", except otherwise indicated, includes matrix nanospheres and core-shell vesicular nanocapsules. In both cases, due to the large specific surface of these systems, the molecules of the POI, if present, may be trapped or adsorbed in the surface of the nanoparticles.

In a particular embodiment, the nanoparticle of the invention is a matrix nanosphere which comprises a matrix, said matrix comprising a vegetable hydrophobic protein and at least a water miscible non-volatile organic solvent of said protein. In this embodiment, the matrix of the nanosphere is a three dimensional network formed by a vegetable hydrophobic protein and one or more water miscible non-volatile organic solvents of said protein. In this embodiment, the product of interest can be trapped or encapsulated within the nanosphere or, alternatively, the product of interest can be adsorbed on or conjugated to the surface of the nanosphere.

In another particular embodiment, the nanoparticle of the invention is a core-shell nano-vesicular structure (a core-shell vesicular nanocapsule) which comprises a core and a shell, said shell comprising a vegetable hydrophobic protein and at least a water miscible non-volatile organic solvent of said protein. The cavity (core or reservoir) contains the POI in liquid, semi-solid or solid form or as a molecular dispersion; this reservoir can be lipophilic or hydrophobic according to the preparation method and raw materials used. This is particularly useful for carrying POIs in the form of a liquid, semisolid or solid state, for example, oils, water-immiscible liquids, organic solutions or suspensions, including oily solutions or suspensions, comprising a POI, aqueous solutions or suspensions comprising the POI, etc. According to this embodiment, the POI can be within the core of the nanocapsule or, alternatively, it can be adsorbed on the surface of the nanocapsule.

In another particular embodiment, the invention provides a combination of at least a matrix nanosphere according to the invention and at least a core-shell vesicular nanocapsule according to the invention.

The term "vegetable hydrophobic protein" has been defined previously. In a particular embodiment, the vegetable hydrophobic protein is a protein from a cereal plant; preferably a protein from a plant selected from corn, wheat, barley, rice, millet and sorghum; more preferably from corn. In another preferred embodiment the vegetable hydrophobic protein is a protein found in a grain.

Prolamines are a family of vegetable hydrophobic proteins found in cereal grains and associated with starch that have specific names and include, without limitation: wheat (gliadin), barley (hordein), rye (secalin), corn (zein), sorghum (kafirin), millet (panicin), rice (orzenin) and oats (avenin). Said proteins form part of the gluten. Thus, in a preferred embodiment the vegetable hydrophobic protein is a prolamine, preferably a prolamine selected from gliadin, hordein, secalin, zein, kafirin, panicin, orzenin and avenin; more preferably the prolamine is selected from gliadin, hordein, secalin, zein, kafirin and avenin; even more preferably is selected from zein, gliadin, hordein and kafirin; the most preferred being zein.

Zein protein can be obtained by solvent extraction of corn gluten meal. Methods for extraction of zein are known by the skilled in the art (see [15]). Zein is also commercially available. Biologically, zein is a mixture of proteins varying in molecular size and solubility. These proteins can be separated by differential solubilities and their related structures into four distinct types: α, β, γ, and δ [15]. α-Zein is by far the most abundant, accounting for approximately 70% of the total with molecular weight about 22 kDa [35]. These classes of zein: α, β, γ, and δ are expressed sequentially in maize and are found to interact with each other for stability. Zein from corn was reported to be approximately 35% α-zein, which includes 2 prominent bands of 22 and 24 kDa. β-zein fails to enter an SDS-PAGE gel without reduction. Reducing SDS-PAGE analysis shows that β-zein has 3 major bands of 24, 22, and 14 kDa [36]. The zein useful in the present invention may be any of the four classes of zein (α, β, γ, and δ) or a mixture thereof. In a preferred embodiment zein is a mixture of the four classes of zein, more preferably a mixture of the four classes of zein mainly composed of α-zein. In a more preferred embodiment the zein is a commercially available zein.

Zein solubility was reported in a review [15]. Zein is soluble in aqueous alcohols, glycols, ethyl ether, furfuryl alcohol, tetrahydrofurfuryl alcohol, and aqueous alkaline solutions of pH 11.5 or greater. Zein is insoluble in water, acetone, and anhydrous alcohols (except methanol). It is of interest that all of the primary solvents are glycols, glycolethers, amino-alcohols, nitro-alcohol acids, amides, and amines. Glycols have considerably greater solvent power than do their corresponding monohydric alcohols. Propylene glycol is a good solvent for zein but absolute propanol is not. Adding additional hydroxyl groups seems to lower the solvent power. Propylene glycol can dissolve zein at room temperature, whereas glycerol needs to be heated to 150° C., and polypropylene glycols with a molecular weight higher than (>) 3,000 do not dissolve zein at all [15].

Zein, the prolamine in corn endosperm contains more than 50% nonpolar amino acids arranged in an unique spatial disposition consisting of tandem repeats of alpha-helix segments aligned parallel to each other forming a ribbon or prism. This structure gives rise to well defined hydrophobic and hydrophilic domains at the protein surface. The goal is to produce nanostructures of controlled geometry, useful as microencapsulation materials for fatty acids, flavours, oleoresins, vitamins, and peptides [37].

The nanoparticles of the invention also contain at least a water miscible non-volatile organic solvent of the hydrophobic protein used. At least a water miscible non-volatile organic solvent has to be a primary solvent of said protein. Thus, the water miscible non-volatile organic solvent may be a primary solvent or a mixture of primary solvents or a mixture of at least a primary solvent and one or more secondary solvents. The terms "water miscible" and "non-volatile organic solvent" have been previously defined. The water miscible non-volatile organic solvent of the present invention may be different depending on the vegetable hydrophobic protein used, since it is a requirement of the primary solvent that it must be capable of dissolving said protein. The "solubility" of a protein is defined as grams of protein totally dissolved in a given amount of solvent at a certain temperature. A protein is considered soluble in a solvent according to the British Pharmacopoeia if it is necessary to use about 10-30 parts of solvent (mL) for one part of solute (g) at a temperature ranging between 15° C. and 25° C. to dissolve the protein.

In this context, the term "primary solvent" is used for those solvents in which the protein is totally soluble without the use of cosolvents. Zein primary solvents are glycols, glycol-ethers, amino-alcohols, nitro-alcohols acids, amides and amines [15]. In a particular embodiment, the primary solvent is selected from, butyl tartrate, 1,3-butylene glycol, diethanolamine, diethylene glycol, diethylene glycol monomethyl ether, ethyl lactate, ethylene glycol, ethylene glycol monoethyl ether, ethylene glycol monomethyl ether, propylene glycol, dipropylene glycol, triethanolamine, triethylenetetramine, triethylene glycol, hydroxyethyl ethylenediamine, glycerol, glycerol-α-methyl ether, 2-amino-2-ethyl-1,3-propanodiol, methyl lactate, monoethanolamine, phenol and resorcinol monoacetate; preferably from propylene glycol, dipropylene glycol, triethanolamine, ethylene glycol, 1,3-butylene glycol, triethylenetetramine, triethylene glycol, methyl lactate, monoethanolamine, ethylene glycol monoethyl ether and ethyl lactate; more preferably from propylene glycol, dipropylene glycol, triethanolamine, ethylene glycol, 1,3-butylene glycol and methyl lactate; even more preferably from propylene glycol, 1,3-butylene glycol and ethyl lactate.

Accordingly, the term "secondary solvent" is used in the present invention to those solvents that are miscible with primary solvents and that are not able to dissolve the protein at temperature less than 40° C., but they are able to keep in solution the protein when mixed in appropriate proportions with a primary solvent. Illustrative, non-limitative examples of suitable secondary solvents are: water, glycerol, ethylene glycol, polyethylene glycol, diethylene glycol monoethyl ether, caprylocaproyl macrogol-glyceride, polyoxyethylene-polyoxypropylene copolymer, etc. Thus, depending on the proportion of the secondary solvent used, it can act as vegetable hydrophobic protein non-solvent (when is used in proportion required to precipitate vegetable hydrophobic proteins), or as vegetable hydrophobic protein solvent (when mixed with a primary solvent in proportion less than required to form nanoparticles). The skilled person in the art may determine the volume of the secondary solvent appropriate to precipitate or dissolve the vegetable hydrophobic protein by performing a study for determining the solubility of the protein in a solvent as showed in Example 2.1.

Therefore, the term binary, ternary or multiple mixtures is used to designate those mixtures of one, two or multiple secondary solvents with at least a primary solvent.

In a preferred embodiment at least a water miscible non-volatile organic solvent is a polyol. In a more preferred embodiment the polyol is a glycol, preferably is propylene glycol. In a preferred embodiment the water miscible non-volatile organic solvent is a solvent suitable for cosmetic or pharmaceutical use.

In another preferred embodiment the water miscible non volatile organic solvent is propylene glycol or a mixture of propylene glycol and other primary and/or secondary solvents. In an embodiment the water miscible non-volatile organic solvent is a binary mixture of propylene glycol and Lutrol®. In another embodiment the water miscible non-volatile organic solvent is a binary mixture of propylene glycol and glycerol. In another embodiment the water miscible non-volatile organic solvent is a binary mixture of propylene glycol and water.

Prolamines are characterized by their insolubility in water and solubility in aqueous alcohol. Prolamines are soluble in extremely acidic or alkaline solutions and in aqueous mixtures of organic solvents, which belong to the following classes: hydroxyl compounds (e.g., ethanol, 2-propanol or glycerol), ketones (e.g., acetone, methyl ethyl ketone) and amides (e.g., acetamide). Prolamines are soluble in aqueous mixtures of these solvents which contain no more than 60% by weight of water. For the purposes of this invention the "water-miscible non-volatile organic solvent" cannot be a volatile solvent such as ethanol or acetone. In a preferred embodiment, the water-miscible non-volatile organic solvent for prolamines is a polyol, preferably a glycol, more preferably propylene glycol.

When the protein is zein, the water-miscible non-volatile organic solvent may be one of the primary solvents reported in [15]. Illustrative, non-limitative examples of suitable solvents are butyl tartrate, 1,3-butylene glycol, diethanolamine, diethylene glycol, diethylene glycol monoethyl ether, diethylene glycol monomethyl ether, ethyl lactate, propylene glycol, ethyl ether tripropylene glycol, ethylene glycol, ethylene glycol monoethyl ether, ethylene glycol monomethyl ether, glycerol, glycerol-α-methyl ether, propylene glycol, dipropylene glycol, triethylene glycol, lactic acid, triethanolamine, triethylenetetramine, diethylenetriamine 2-amino-2-ethyl-1,3-propandiol, 2-amino-2-methyl-1-propanol, hydroxyethylethylenediamine, methyl lactate, monoethanolamine, phenol, resorcinol monoacetate.

In a preferred embodiment, the water-miscible non-volatile organic solvent for zein is a polyol, preferably a glycol, more preferably propylene glycol (PG).

The nanoparticles of the invention can comprise one, two or three water miscible non-volatile organic solvents. In a preferred embodiment the nanoparticles of the invention comprise a binary mixture of solvents, preferably a mixture of propylene glycol and other primary or secondary water miscible non-volatile organic solvent.

Due to the large specific surface of the nanoparticles of the invention, the molecules of a product of interest may be trapped or adsorbed in or conjugated to the surface of the nanoparticles. Thus, the nanoparticles of the invention can efficiently incorporate products of interest, such as large or small, hydrophobic or hydrophilic compounds, having different physical state, uses and applications, and, thus, they can be potentially applied in different industries (e.g., in pharmaceutical, cosmetic or agricultural compositions, in food products, etc.).

Thus, in a particular embodiment, the nanoparticle of the invention further comprises a product of interest (POI); in this case, the nanoparticle of the invention is occasionally identified in this description as "loaded nanoparticle of the invention". Information related to said POI may be found in the above section ("Definitions"). The skilled person in the art will understand that a loaded nanoparticle of the invention can incorporate one or more products of interest (POIs) in the same nanoparticle provided that said POIs are not incompatible each other.

In a particular embodiment, said POI is the antioxidant curcumin, or the antimicrobial drug chlorhexidine and the nanoparticle of the invention is a matrix nanosphere wherein the POI is trapped or encapsulated within the nanosphere or, alternatively, it is adsorbed on or conjugated to the surface of the nanosphere.

In another particular embodiment, said POI is an essential oil, independent of its physical state, such as a volatile oil including, among others, aromatic oils that are miscible with PG:zein solution including *Mentha piperita* (peppermint) oil, eugenol, cinnamon oil, thyme (*Thymus vulgaris*) oil, or aromatic oils that are immiscible with PG:zein solution such as lemon essential oil; non-volatile oils, such as cod liver oil; or fatty acids such as oleic acid or linolenic acid, etc., associated or encapsulated within the nanoparticle of the invention which is a core-shell vesicular nanocapsule wherein the POI is trapped or encapsulated within the nanocapsule or, alternatively, it is adsorbed on or conjugated to the surface of these nanocapsules. In a preferred embodiment, the essential oil is a volatile oil miscible with the PG:zein solution, preferably selected from *Mentha piperita* oil, eugenol, cinnamon oil and *Thymus vulgaris* oil. In another preferred embodiment the essential oil is a volatile oil immiscible with PG:zein solution, preferably lemon essential oil. In another preferred embodiment the essential oil is a non-volatile oil, preferably selected from cod liver oil, oleic acid and linolenic acid.

In another particular embodiment, said POI is an oil in the form of solution, suspension or emulsion, associated or encapsulated within the nanoparticle of the invention which is a core-shell vesicular nanocapsule wherein the POI is trapped or encapsulated within the nanocapsule or, alternatively, it is adsorbed on or attached to the surface of the nanocapsule.

The vegetable hydrophobic protein:POI weight ratio, preferably the "zein":POI weight ratio, in the loaded nanoparticle of the invention may vary within a broad range; nevertheless, in a particular embodiment, the vegetable hydrophobic protein (preferably zein):POI weight/weight ratio in the loaded nanoparticle of the invention may be comprised between $1:10^{-6}$ and $1:10^6$, preferably between $1:10^{-4}$ and $1:10^3$, and more preferably between $1:0.001$ and $1:100$.

Matrix nanoparticles and core-shell vesicular nanocapsules of the invention are mainly cationic or anionic with positive or negative average surface charge, respectively.

Anionic nanoparticles can be obtained by coating nanoparticles with anionic polymers such as arabic gum or by complexation of the anionic polymer in the matrix or shell of the nanoparticles. In a preferred embodiment the anionic or polyanionic polymer used is arabic gum.

Process for Producing Polymeric Particulate Systems

In another aspect, the invention relates to a process for producing a matrix nanosphere which comprises a matrix, said matrix comprising a vegetable hydrophobic protein and at least a water miscible non-volatile organic solvent, hereinafter referred to as "process [1] of the invention", which comprises contacting a solution of the vegetable hydrophobic protein in at least a water miscible non-volatile organic solvent with a vegetable hydrophobic protein non-solvent, preferably an aqueous medium, in order to form said matrix nanosphere and wherein the solution of the vegetable hydrophobic protein does not comprise a volatile organic solvent. This process [1] of the invention renders "empty" nanoparticles of the invention, i.e., nanoparticles without product of interest (POI), particularly matrix nanospheres wherein the matrix comprises a vegetable hydrophobic protein and at least a water miscible non-volatile organic solvent of the vegetable hydrophobic protein.

The particulars of the water miscible non-volatile organic solvent have been defined in the "Definitions" section. The embodiments related to the water miscible non-volatile organic solvent disclosed in the context of the nanoparticles of the invention are also applicable to the process [1] of the invention.

The organic solvent can be any suitable water miscible non-volatile organic solvent in which the vegetable hydrophobic protein can be solubilized, preferably a pharmaceutically, food or cosmetically acceptable non-volatile organic solvent and include a primary solvent or an appropriate mixture of at least a primary solvent and one or more secondary solvents. Additionally, the organic solvent may be a mixture of more than one primary solvent. Illustrative, non-limitative, examples of organic solvents which can be used within the context of the process [1] of the invention, include glycols and glycol-ethers among others.

The term "glycol", as used herein, refers to any non-volatile organic compound containing two hydroxyl functional groups (—OH). Glycols are also named diols and include alcohols such as propylene glycol (PG), poly ethylene glycol (PEG), ethylene glycol, diethylene glycol, etc. PG and PEG are non-volatile alcohols which may be present as a liquid (PG) or as a solid depending on the molecular weight (Mw) of the PEG (e.g., PEG6000, PEG10000). Solid solvents (e.g., PEG6000, PEG10000, etc.) can be used, for example, to produce solid pharmaceutical forms for the administration of drugs, such as suppositories, for example, rectal suppositories comprising, e.g., antipyretic drugs, or vaginal suppositories (ovules) comprising, e.g., antifungal agents, among others, and nanoparticles will be formed when the solution comprising the vegetable hydrophobic protein and the water miscible non-volatile organic solvent contacts with a body fluid, e.g., the vaginal fluid or gastrointestinal tract fluids. Glycols useful in the present invention as primary solvents are those in which the vegetable hydrophobic protein can be dissolved. Thus, glycols in which the vegetable hydrophobic protein cannot be dissolved are useful as secondary solvents (when mixed with a primary solvent in proportion less than required to form nanoparticles) or as vegetable hydrophobic protein non-solvent. Therefore, the glycol used will depend on the specific vegetable hydrophobic protein to be dissolved. Zein solvents are disclosed in [15]. Suitable zein solvents are, without limitation, 1,3-butylene glycol, diethylene glycol, dipropylene glycol, ethylene glycol, propylene glycol, triethylene glycol, etc. In a particular embodiment, the organic solvent is a glycol, preferably propylene glycol.

The term "glycerol", also named glycerin or glycerine, refers to a polyol having three hydroxyl groups that are responsible for its solubility in water and its hygroscopic nature. In a preferred embodiment the water miscible non-volatile organic solvent is a polyol, preferably glycerol as primary solvent at temperatures above 139° C., and as secondary solvent at temperatures below 139° C.

The term "glycol ether", as used herein, refers to a group of solvents based on alkyl ethers of ethylene glycol. Suitable glycol ethers for the present invention are, without limitation, diethylene glycol monoethyl ether, diethylene glycol monomethyl ether, ethylene glycol monoethyl ether, ethylene glycol monomethyl ether, etc.

In a particular embodiment, the water miscible non-volatile organic solvent is a polyglycol. Examples of polyglycols are, without limitation, polyethyleneglycols (PEGs), methoxypolyethylene glycols (MPEGs), polypropylene glycols (PPGs) and polybutylene glycols (PBGs).

In another particular embodiment, the organic solvent comprises a mixture of two or more water miscible non-volatile polyglycols as primary or secondary solvents.

In another preferred embodiment the water miscible non-volatile organic solvent is a polyol. The term "polyol" has been defined in the "Definitions" section.

The water miscible non-volatile organic solvents useful in the invention may be listed in more than one category, for example propylene glycol (PG) which is a polyol and also a glycol.

In another embodiment, the non-volatile, water miscible, organic solvent comprises at least one polyol (PG) or an appropriate solvent mixture of at least a primary solvent and one or more secondary solvents, including binary and ternary solvent mixtures for the vegetable hydrophobic protein, particularly zein. Illustrative non limited examples are PG:Glycerol mixture, PG:water mixture at a percentage of water that keep zein soluble or PG:PEG:Glycerol mixture. Alternatively, the organic solvent comprises PG and a non-volatile PG miscible solvent other than an alcohol. Illustrative, non-limitative, examples of non-volatile water miscible solvents other than alcohols that can form part of a binary mixture with PG include polyoxyglycerides, e.g., caprylocaproyl polyoxyglycerides, fatty acid derivatives, e.g., their PG or PEG derivatives, etc. The term "caprylocaproyl polyoxyglycerides" refers to a lipid-based surface-active agent. One exemplary caprylocaproyl polyoxyglyceride is PEG-8 caprylic/capric glycerides, marketed as Labrasol® by Gattefosse. Caprylocaproyl polyoxyglycerides are also known as "caprylocaproyl macrogolglycerides". In a preferred embodiment the water miscible non-volatile organic solvent is a binary mixture of PG:glycerol. In another preferred embodiment the water miscible non-volatile organic solvent is a binary mixture of PG:Labrasol®. In another preferred embodiment the water miscible non-volatile organic solvent is a binary mixture of PG:Tween® 80. In another preferred embodiment the water miscible non-volatile organic solvent is a binary mixture of PG:Lutrol®. In another preferred embodiment the water miscible non-volatile organic solvent is a binary mixture of PG:water.

In a preferred embodiment the primary water miscible non-volatile organic solvent of the solution of the vegetable hydrophobic protein is the majority solvent in said solution.

Particulars of the vegetable hydrophobic protein have been defined in the "Definitions" section and in the context of the nanoparticles of the invention. The embodiments related to the vegetable hydrophobic protein disclosed in the context of the nanoparticles of the invention are also applicable to the process [1] of the invention.

In a particular embodiment the vegetable hydrophobic protein is a protein from a cereal plant; preferably a protein from a plant selected from corn, wheat, barley, rice, millet and sorghum; more preferably from corn. In another preferred embodiment the vegetable hydrophobic protein is a protein found in a grain.

In a particular embodiment the vegetable hydrophobic protein is a prolamine, preferably a prolamine selected from gliadin, hordein, secalin, zein, kafirin, panicin, orzenin and avenin; more preferably the prolamine is selected from gliadin, hordein, secalin, zein, kafirin and avenin; even more preferably is selected from zein, gliadin, hordein and kafirin; the most preferred being zein.

The concentration of said vegetable hydrophobic protein, in the water miscible non-volatile organic solvent to form a solution can vary within a broad range; nevertheless, in a particular embodiment, the concentration of the vegetable hydrophobic protein, preferably zein, in said organic solution is comprised between 0.01% and 50% (w/v), preferably between 0.1% and 30% (w/v), more preferably between 1% and 15% (w/v), still more preferably between 1% and 10% (w/v); in a specific embodiment, the concentration of the vegetable hydrophobic protein, preferably zein, in the organic solution is between 2.5-5% (w/v).

The organic solution containing a vegetable hydrophobic protein, preferably zein, can be prepared by dissolving said product in the organic solvent. In a particular embodiment, the organic solvent is a water miscible non-volatile polyol, e.g., PG. In another particular embodiment, the organic solvent is a non-volatile water miscible binary or ternary solvent mixture containing at least one or two polyol and optionally a solvent other than an alcohol such as a polyoxyglyceride, for example, a caprylocaproyl macrogol-glyceride, polyoxyethylene-polyoxypropylene copolymer (Lutrol® L 44, Poloxamer USP-NF) or a fatty acid derivative.

According to process [1] of the invention, an organic solution containing a vegetable hydrophobic protein in at least a water miscible non-volatile organic solvent, is contacted with a vegetable hydrophobic protein non-solvent, preferably an aqueous medium, which acts as a hydrophobic protein non-solvent capable of mixing with the solvent used in the organic solution. This mixture causes hydrophobic protein precipitation in order to form the nanoparticles. In a preferred embodiment, an organic solution containing zein in PG is contacted with an aqueous medium, which acts as a PG miscible hydrophobic protein non-solvent, thus causing precipitation of zein and formation of nanoparticles.

In a particular embodiment, the aqueous medium comprises water, preferably, distilled or bidistilled water. This step is performed at a suitable temperature, typically comprised between 1° C. and 150° C., preferably between 10° C. and 40° C., more preferably between 15° C. and 25° C. Subsequently, if desired, the suspension of nanoparticles obtained is subjected to a suitable treatment to eliminate the organic solvent. Elimination of the organic solvent can be performed by any conventional method, depending on the nature of the solvent to be removed, known by the skilled person in the art including, for example, centrifugation, dialysis, etc. In a particular embodiment, when the organic solvent is PG, the nanoparticles suspension is centrifuged, in order to eliminate said polyol. Alternatively, the nanoparticles suspension can be dried by different techniques, e.g., lyophilization with some excipients such as sugars, salts, polysaccharides or surfactants.

In a preferred embodiment the medium further comprises a surfactant and/or a polyanionic polymer.

Alternatively, said nanoparticles can be produced in situ by the mixing of the vegetable hydrophobic protein dissolved in a water miscible non-volatile organic solution with any body fluid. For that purpose, the organic solution wherein the protein solvent is a non-volatile water miscible solvent (such as a non-volatile water miscible alcohol, e.g., PG, or a non-volatile water miscible solvent other than an alcohol, e.g., lactic acid, triethanolamine) containing the vegetable hydrophobic protein is prepared by mixing said vegetable hydrophobic protein with said organic solvent, and then mixing said organic solution containing the vegetable hydrophobic protein with an aqueous medium, such as a body fluid, for example, gastrointestinal fluid, blood, intravitreal, subcutaneous, vaginal fluid, etc., and, consequently, in situ self-assembled nanoparticles of the vegetable hydrophobic protein, preferably zein (ZSNP), are directly formed.

According to this embodiment, if the organic solution containing the vegetable hydrophobic protein is a solution wherein the solvent is a non-volatile water miscible polyol, e.g., PG, and said non-volatile polyol solution containing the vegetable hydrophobic protein is administered as such by a suitable route which allows the contact of said solution or suspension with a body fluid, e.g., via oral, parenteral, rectal, vaginal, or the like, to a subject (e.g., an animal including a human being), then nanoparticles are formed in situ by self-assembly of the vegetable hydrophobic protein chains, preferably zein chains, in contact with said suitable body fluid comprising an aqueous medium.

Thus, the solution containing a vegetable hydrophobic protein in a medium, said medium comprising at least a water miscible non-volatile organic solvent and, optionally, an aqueous medium, wherein the amount of aqueous medium is lower than the necessary amount of aqueous medium to form nanoparticles, wherein the medium comprising at least a water miscible non-volatile organic solvent does not comprise a volatile organic solvent, and wherein the amount of vegetable hydrophobic protein is comprised between 0.01% and 50% (w/v), preferably between 0.01% and 40% (w/v), more preferably between 0.01% and 30% (w/v), still more preferably between 0.01% and 20% (w/v), still more preferably between 0.01% and 15% (w/v), even more preferably between 0.01% and 10% (w/v), even more preferably between 0.01% and 5% (w/v), the most preferred between 0.01% and 2.5% (w/v) constitutes an additional aspect of the present invention. In a preferred embodiment the vegetable hydrophobic protein of said solution is selected from hordein, secalin, zein, kafirin, panicin, orzenin and avenin; more preferably is selected from hordein, secalin, zein, kafirin and avenin; even more preferably is selected from zein, hordein and kafirin; the most preferred being zein. In another embodiment, the amount of vegetable hydrophobic protein in said solution is higher than 0.1% (w/v), at least 0.2% (w/v), at least 0.5% (w/v), at least 1% (w/v), at least 5% (w/v), at least 10% (w/v), at least 15% (w/v), at least 20% (w/v), at least 25% (w/v), at least 30% (w/v), at least 35% (w/v), at least 40% (w/v) and not more than 50% (w/v). In another embodiment the amount of vegetable hydrophobic protein is comprised between 0.01% and 50% with the proviso that when the vegetable hydrophobic protein is gliadin, then the amount of vegetable hydrophobic protein is higher than 0.1%.

Said solution must be able to form vegetable hydrophobic protein nanoparticles when mixed with appropriate amount of vegetable hydrophobic protein non-solvent, preferably an aqueous medium. Said organic solution can be used to produce nanoparticles, mainly matrix nanospheres, wherein said matrix comprises a vegetable hydrophobic protein and at least a water miscible non-volatile organic solvent, after entering into contact with a vegetable hydrophobic protein non-solvent, preferably with an aqueous medium, preferably with a biological fluid. In a particular embodiment, the water miscible non-volatile organic solvent is propylene glycol, and the aqueous medium comprises water, preferably is a biological fluid. In a preferred embodiment, the medium comprises a binary or ternary mixture of a water miscible non-volatile organic solvent. In a preferred embodiment, the vegetable hydrophobic protein is a prolamine, preferably zein. In a preferred embodiment the water miscible non-volatile organic solvent is selected from a polyol, preferably is a glycol, more preferably propylene glycol. In a preferred embodiment, the solution or suspension further comprises a surfactant and/or a polyanionic polymer.

The amount of vegetable hydrophobic protein non-solvent, preferably an aqueous medium, which is necessary to form the nanoparticles depend, among other factors, on the concentration of said vegetable hydrophobic protein in the hydro-organic solution or suspension containing said hydrophobic protein, and on the selected vegetable hydrophobic protein non-solvent; nevertheless, in a particular embodiment the ratio vegetable hydrophobic protein non-solvent: water miscible non-volatile organic solvent is comprised between 0.01:1 (v/v) and 1000:1 (v/v), preferably between 0.5:1 (v/v) and 10:1 (v/v), more preferably about 4:1 (v/v).

The concentration of the vegetable hydrophobic protein, preferably zein, in the organic non-volatile water miscible solvent solution containing said protein can vary within a broad range; nevertheless, in a particular embodiment, the concentration of the vegetable hydrophobic protein, preferably zein, in said organic solution is comprised between 0.01% and 50% (w/v), preferably between 0.1% and 30% (w/v), more preferably between 1% and 15% (w/v), still more preferably between 2% and 10% (w/v); in a specific embodiment, the concentration of the hydrophobic protein, preferably zein, in the organic solution is about 2-5% (w/v).

In another aspect, the invention relates to a process for producing a matrix nanosphere which comprises a product of interest (POI), wherein said matrix nanosphere comprises a matrix, said matrix comprising a vegetable hydrophobic protein and at least a water miscible non-volatile organic solvent, hereinafter referred to as "process [2] of the invention", which comprises: contacting a solution, or suspension comprising said POI and said vegetable hydrophobic protein, dissolved in at least a water miscible non-volatile organic solvent, with a vegetable hydrophobic protein non-solvent, preferably an aqueous medium, in order to form said matrix nanosphere and wherein the solution or suspension comprising the vegetable hydrophobic protein and the product of interest does not comprise a volatile organic solvent. Process [2] of the invention renders "loaded" nanoparticles of the invention, namely, matrix nanospheres loaded with at least a product of interest (POI). According to the process [2] of the invention, the water miscible non-volatile organic solution or suspension comprising a POI and a vegetable hydrophobic protein, is contacted with a vegetable hydrophobic protein non-solvent, preferably an aqueous medium. The POI can be a hydrophobic, hydrophilic or an amphiphilic compound. In the case of hydrophilic compounds, optionally a small percentage of water can be added to the non-volatile water miscible organic solvent containing zein at a percentage that must not cause zein precipitation.

Briefly, a solution, or suspension comprising a POI and a vegetable hydrophobic protein in a non-volatile water miscible organic solvent may be obtained by conventional means known by the skilled person in the art, for example, by mixing a non-volatile water miscible organic solvent solution or suspension comprising a POI and a hydrophobic protein (obtainable by dissolving, or suspending the POI in a suitable water miscible non-volatile organic solvent containing a hydrophobic protein), or alternatively, an aqueous solution, or suspension of said POI (obtainable by dissolving or suspending the POI in an aqueous medium, wherein the amount of aqueous medium is lower than the necessary amount of aqueous medium to form nanoparticles, for example, a medium comprising water, preferably, water which acts as a water miscible protein non solvent), with an organic solution of the vegetable hydrophobic protein, under suitable conditions to obtain said solution, or suspension comprising a POI and a vegetable hydrophobic protein. Illustrative, non-limitative, examples of said operation conditions include stirring, at room temperature, for a suitable period of time, for example, from 1 to 30 minutes, typically, less than 15 minutes, preferably around 5 minutes.

The particulars of the POI have been previously mentioned in the "Definitions" section.

The particulars of the vegetable hydrophobic protein have been previously mentioned in connection with the process [1] of the invention as well as the particulars of the solution of the vegetable hydrophobic protein, e.g., alcohols, concentration, etc. In a preferred embodiment, the vegetable hydrophobic protein is a prolamine, preferably zein. The particulars of the water miscible non-volatile organic solvent have been previously mentioned in connection with the process [1] of the invention. In a particular embodiment, the alcohol present in the alcoholic solution is a polyol, preferably a glycol, more preferably is propylene glycol (PG).

All the embodiments disclosed in connection with the process [1] of the invention are also applicable to process [2] of the invention.

According to the process [2] of the invention, a solution, or suspension of a vegetable hydrophobic protein in a water miscible non-volatile organic solvent comprising a POI is contacted with a vegetable hydrophobic protein non-solvent, preferably an aqueous medium, i.e., a medium comprising water, which acts as a water miscible polymer non-solvent, in order to form the nanoparticles loaded with said POI ("POI-loaded nanoparticles"). In a particular embodiment, the vegetable hydrophobic protein non-solvent comprises water, preferably, distilled or bidistilled water. The volume ratio between the protein solvent (alcohol, e.g., PG) and the protein non-solvent (e.g., water) [solvent: non-solvent] can vary within a broad range, typically between 1:0.001 (v/v) and 1:5000 (v/v), preferably between 1:4 (v/v) and 1:5 (v/v).

The step of contacting the vegetable hydrophobic protein solution, or suspension in water miscible non-volatile organic solvent comprising POI with the protein non-solvent medium is performed at a suitable temperature, typically comprised between 1° C. and 150° C., preferably, between 10° C. and 40° C., and more preferably between 15° C. and 25° C.

Subsequently, if necessary, the suspension of POI-loaded nanoparticles so obtained is subjected to a suitable treatment to eliminate the water miscible non-volatile organic solvent in order to obtain a protein non-solvent suspension, preferably an aqueous suspension, of POI-loaded nanoparticles free from polyols. Elimination of the water miscible non-volatile organic solvent (preferably polyol) can be performed by conventional methods known by the skilled person in the art including, for example, centrifugation or dialysis, etc.; in a particular embodiment, the POI-loaded nanoparticles suspension is centrifuged to eliminate PG. However, when the solvent is PG it is not necessary to remove it since it can be used in human by oral or parenteral routes.

In a preferred embodiment the medium further comprises a surfactant and/or a polyanionic polymer.

According to the process [2] of the invention, in order to obtain ("POI-loaded nanoparticles"), a solution or suspension of zein in non-volatile organic solvent comprising a POI in the form of suspension or solution is contacted with a vegetable hydrophobic protein non solvent, preferably with an aqueous medium, i.e., a medium comprising water, which acts as a water miscible zein non-solvent spontaneously or under magnetic stirring. Illustrative, non-limitative, examples of said operation conditions include stirring, at room temperature, for a suitable period of time, for example, from 1 to 30 minutes.

Alternatively, due to the possibility of the vegetable hydrophobic protein to form in situ self-assembled nanoparticles (ZSNP), the invention provides an additional process for producing a matrix nanosphere which comprises a matrix and a product of interest (POI), said matrix comprising a vegetable hydrophobic protein and at least a water miscible non-volatile organic solvent, which comprises contacting an organic solution, or suspension comprising said POI and said vegetable hydrophobic protein, wherein said organic solution, or suspension comprises a non-volatile water miscible solvent, with a body fluid, for example, gastrointestinal fluid, blood, intravitreal, vaginal etc., and, consequently, in situ self-assembled nanoparticles of the vegetable hydrophobic protein loaded with POI (Loaded-ZSNP) are directly formed. This process renders "loaded" nanoparticles of the invention, namely, in situ self-assembled matrix nanospheres loaded with at least a POI. According to this process, an organic solution, or suspension comprising a POI and a vegetable hydrophobic protein, in at least a non-volatile water miscible solvent is contacted with an aqueous body fluid.

This process is useful when the POI is a hydrophobic, hydrophilic or amphiphilic compound. Briefly, an organic solution, or suspension comprising a POI and a vegetable hydrophobic protein in a non-volatile water miscible solvent is obtained by mixing a solution, or suspension of said POI (obtainable by dissolving, or dispersing the POI in a non-volatile water miscible solvent or in an aqueous medium wherein the amount of aqueous medium is lower than the necessary amount of aqueous medium to form nanoparticles) with a solution of said vegetable hydrophobic protein in a non-volatile water miscible organic solvent, under suitable conditions to obtain said solution, or suspension comprising a POI and a vegetable hydrophobic protein, particularly zein, in a non-volatile water miscible solvent.

Illustrative, non-limitative, examples of said operation conditions to obtain POI:protein solution, or suspension in non-volatile organic solvent include stirring, at room temperature, for a suitable period of time, for example, from 1 to 30 minutes, preferably around 20 minutes, typically, less than 15 minutes, preferably around 5 minutes. Although the solvents of said solutions or suspensions (the solution or suspension of the POI and the solution of the vegetable hydrophobic protein) may be different, in practice, it is preferred that the solvent of both solutions or suspensions is the same; in a particular embodiment, said solvent is a polyol such as PG.

The particulars of the POI have been previously mentioned in the "Definitions" section. The particulars of the vegetable hydrophobic protein, preferably a prolamine, more preferably zein, have been previously mentioned in connection with the process [1] of the invention. The particulars of the water soluble non-volatile organic solvent have been previously mentioned in connection with the process [1] of the invention.

As mentioned above, the solvent may be any suitable solvent, such as a non-volatile water miscible solvent, in which the vegetable hydrophobic protein can be solubilized, preferably a pharmaceutically or cosmetically acceptable non-volatile water miscible solvent. Illustrative, non-limitative, examples of non-volatile water miscible primary solvents which can be used within the context of the process [2] of the invention, include non-volatile water miscible alcohols, for example, PG, etc. The non-volatile water miscible primary solvent(s) may be mixed in appropriate proportions with a secondary solvent, for example non-volatile water miscible solvents other than alcohols, such as polyoxyglycerides, e.g., caprylocaproyl polyoxy-glycerides (Labrasol®), fatty acid derivatives, e.g., their PG or PEG derivatives, etc., and any mixture thereof, for example, a mixture of two or more non-volatile water miscible alcohols, a mixture of two or more non-volatile water miscible solvents other than alcohols, or a mixture of at least one non-volatile water miscible alcohol and at least one non-volatile water miscible solvent other than an alcohol. In a preferred embodiment the water miscible non-volatile organic solvent is propylene glycol.

The concentration of said vegetable hydrophobic protein, preferably zein, in the solution, or suspension comprising said POI and said non-volatile water miscible solvent can vary within a broad range; nevertheless, in a particular embodiment, the concentration of the vegetable hydrophobic protein, preferably zein, in said solution, or suspension is comprised between 0.01% and 50% (w/v), preferably between 0.1% and 30% (w/v), more preferably between 1% and 15% (w/v), still more preferably between 1% and 10% (w/v); in a specific embodiment, the concentration of the vegetable hydrophobic protein, preferably zein, in the organic solution or suspension is about 2.5% (w/v).

According to process [2] of the invention, a solution, or suspension comprising a POI and a vegetable hydrophobic protein in a non-volatile water miscible solvent is contacted with an aqueous body fluid, for example, gastro intestinal fluids, to form the nanoparticles loaded with said POI ("POI-loaded nanoparticles") by in situ self-assembly of the protein chains. In a particular embodiment, the aqueous body fluid comprises simulated intestinal fluid. This step is performed at a suitable temperature, between 10° C. and 50° C., and more preferably between 35° C. and 37° C.

The solution or suspension containing a vegetable hydrophobic protein and a product of interest dissolved or suspended in a medium, said medium comprising at least a water miscible non-volatile organic solvent and, optionally, a surfactant and, optionally, an aqueous medium, wherein the amount of aqueous medium is lower than the necessary amount of aqueous medium to form nanoparticles, wherein the medium comprising at least a water miscible non-volatile organic solvent does not comprise a volatile organic solvent and wherein the amount of vegetable hydrophobic protein is comprised between 0.01% and 50% (w/v), preferably between 0.01% and 40% (w/v), more preferably between 0.01% and 30% (w/v), still more preferably between 0.01% and 20% (w/v), still more preferably between 0.01% and 15% (w/v), even more preferably between 0.01% and 10% (w/v), even more preferably between 0.01% and 5% (w/v), the most preferred between 0.01% and 2.5% (w/v) constitutes an additional aspect of the present invention. In a preferred embodiment the vegetable hydrophobic protein of said solution or suspension is selected from hordein, secalin, zein, kafirin, panicin, orzenin and avenin; more preferably is selected from hordein, secalin, zein, kafirin and avenin; even more preferably is selected from zein, hordein and kafirin; the most preferred being zein. In another embodiment, the amount of vegetable hydrophobic protein in said solution or suspension is higher than 0.1% (w/v), at least 0.2% (w/v), at least 0.5% (w/v), at least 1% (w/v), at least 5% (w/v), at least 10% (w/v), at least 15% (w/v), at least 20% (w/v), at least 25% (w/v), at least 30% (w/v), at least 35% (w/v), at least 40% (w/v) and not more than 50% (w/v). In another embodiment the amount of vegetable hydrophobic protein is comprised between 0.01% and 50% with the proviso that when the vegetable hydrophobic protein is gliadin, then the amount of vegetable hydrophobic protein is higher than 0.1%. Said solution or suspension must be able to form vegetable hydrophobic protein nanoparticles when mixed with appropriate amount of vegetable hydrophobic protein non-solvent, preferably an aqueous medium. Said organic solution or suspension can be used to produce POI-loaded nanoparticles, mainly matrix nanospheres wherein said matrix comprises a vegetable hydrophobic protein and at least a water miscible non-volatile organic solvent, after entering into contact with a protein non-solvent medium, preferably with an aqueous medium, more preferably with a biological fluid. In a particular embodiment, the water miscible non-volatile organic solvent is propylene glycol, and the vegetable hydrophobic protein non-solvent is an aqueous medium that comprises water, and preferably is a biological fluid. In a preferred embodiment, the medium comprises a binary or ternary mixture of a water miscible non-volatile organic solvent. In a preferred embodiment, the vegetable hydrophobic protein is a prolamine, preferably zein. In a preferred embodiment the water miscible non-volatile organic solvent is a polyol, preferably is a glycol, more preferably propylene glycol. In a preferred embodiment, the solution or suspension further comprises a surfactant and/or a polyanionic polymer.

In another aspect, the invention relates to a process for producing a core-shell vesicular nanocapsule which comprises a product of interest (POI) associated to core-shell, wherein said core-shell vesicular nanocapsule comprises a core and a shell, said shell comprising a vegetable hydrophobic protein and at least a water miscible non-volatile organic solvent, hereinafter referred to as "process [3] of the invention", which comprises contacting a solution, suspension or emulsion comprising said POI and said vegetable hydrophobic protein in at least a water miscible non-volatile organic solvent, with a vegetable hydrophobic protein non-solvent, preferably an aqueous medium, in order to form said core-shell vesicular nanocapsule and wherein the solution, suspension or emulsion comprising the vegetable hydrophobic protein and the product of interest does not comprise a volatile organic solvent. The solution, suspension or emulsion comprising a POI and a vegetable hydrophobic protein, is contacted with the protein non-solvent, preferably an aqueous medium, in the absence or in the presence of a surfactant or other excipients. In a particular embodiment, the solution, suspension or emulsion comprising a POI and a vegetable hydrophobic protein, preferably zein, is contacted with an aqueous medium in the presence of a surfactant.

Process [3] of the invention renders "loaded" nanoparticles of the invention, namely, "core-shell vesicular nanocapsules" loaded with at least a POI. The POI can be within the nanocapsule or adsorbed on the surface of the shell nanocapsule.

The particulars of the POI have been defined in the "Definitions" section.

The POI may be in a liquid, semi-solid or solid state. In a particular embodiment, said POI is an oil. Core-shell nanocapsules, preferably zein nanocapsules (ZSNC) can be obtained by either in situ nanoprecipitation-surface deposition technique or emulsification-in situ surface deposition technique. The in situ nanoprecipitation-surface deposition technique is used when oil is miscible with PG, and emulsification-in situ surface deposition technique when the oily material is immiscible with PG.

In another particular embodiment, said POI is dissolved, emulsified or dispersed in a water miscible non-volatile organic solvent where the vegetable hydrophobic protein, was dissolved. In another particular embodiment, said POI is a drug, a cosmetical or a food product in the form of an oily solution or suspension or in the form of a solution or dispersion in a water immiscible solvent.

In another particular embodiment said POI is an excipient, for example liquid paraffin or a melted lipid such as wax. Said excipient is contained in the core of the core-shell vesicular nanocapsule.

According to process [3] of the invention, said POI may be, as example, (i) a volatile oil such as essential peppermint oil, eugenol, cinnamon oil, thyme (*Thymus vulgaris*) oil or their chemical components (i.e., menthol, menthone, etc.) that are miscible with non-volatile organic solvents comprising a vegetable hydrophobic protein, leading to form an organic solution containing oil and protein; (ii) volatile oils such as essential lemon oil or their chemical components (i.e., lemonen) that are immiscible with non-volatile organic solvents comprising a vegetable hydrophobic protein, leading to form an emulsion containing oil droplets and protein solution (iii) non-volatile oils or fatty acids, in liquid, semi solid or solid state, for example oleic acid or linoleic acid, that are miscible or immiscible with non-volatile organic solvents comprising a vegetable hydrophobic protein, leading to form an organic solution or emulsion of said oil in protein solution.

The particulars of the water miscible non-volatile organic solvent have been previously mentioned in connection with the process [1] of the invention. In a particular embodiment, the water miscible non-volatile organic solvent is a polyol, preferably a glycol, more preferably is propylene glycol (PG).

The particulars of the vegetable hydrophobic protein have been previously mentioned in connection with the process [1] of the invention. In a particular embodiment, the vegetable hydrophobic protein is a prolamine, preferably zein.

All the embodiments disclosed in connection with the process [1] of the invention are also applicable to process [3] of the invention.

According to process [3] of the invention, a solution, suspension or emulsion comprising a POI and a vegetable hydrophobic protein is contacted with a vegetable hydrophobic protein non-solvent, preferably with an aqueous medium, in the absence or the presence of a surfactant or in the presence of other excipients. This process is particularly useful when the POI is a hydrophobic, hydrophilic or amphiphilic compound.

Briefly, a solution, suspension or emulsion comprising a POI and a vegetable hydrophobic protein is obtained by mixing, dissolving or emulsifying a POI in an organic solution of a vegetable hydrophobic protein in a water miscible non-volatile organic solvent under suitable conditions to obtain said solution, suspension or emulsion comprising a POI and a vegetable hydrophobic protein.

The water miscible non-volatile organic solvent to be mixed with both the POI and the solution of the vegetable hydrophobic protein, in a particular embodiment, may be the same or different from the solvent which forms the solution of the vegetable hydrophobic protein.

The organic solution, suspension or emulsion containing both the POI and the vegetable hydrophobic protein, preferably zein, may be a water miscible non-volatile polyol, preferably PG. Examples of said organic solutions include virtually any non-volatile water miscible solvent, preferably a pharmaceutically, food or cosmetically acceptable alcohol, e.g., a polyol, e.g., PG, etc., or any mixture of polyols, or at least one polyol, e.g., PG, and at least a non-volatile water miscible solvent other than polyol, such as polyoxyglycerides, e.g., caprylocaproyl polyoxy-glycerides (Labrasol®), fatty acid derivatives, e.g., their PG or PEG derivatives, etc. In a particular embodiment, the water miscible non-volatile organic solvent to be mixed with both the POI and the solution of said vegetable hydrophobic protein is PG (when the liquid phase comprising the POI is highly soluble in PG).

Depending, among other characteristics, on the solubility or miscibility of the POI in a water miscible non-volatile organic solvent containing the vegetable hydrophobic protein, a solution, suspension or emulsion ("the oil droplet size in the range of 10-999 nm") can be obtained in the presence or absence of surfactants.

In a particular embodiment, a solution, suspension or emulsion comprising a POI and a vegetable hydrophobic protein, in the absence or the presence of a surfactant, is contacted with a vegetable hydrophobic protein non-solvent, preferably an aqueous medium, in the absence or the presence of a surfactant or of other excipients to form a core-shell vesicular nanocapsule.

Illustrative, non-limitative, examples of the operation conditions to obtain the solution, suspension or emulsion comprising a POI and a vegetable hydrophobic protein, preferably zein, in a water miscible non-volatile organic solvent, particularly PG, include sonication, high shear homogenization or stirring, at room temperature, for a suitable period of time, for example, from 1 to 30 minutes, typically, less than 15 minutes, preferably around 5 minutes if it is necessary to use stirring.

Illustrative, non-limitative, examples of the operation conditions to obtain core-shell nanocapsules, include mixing the solution, suspension or emulsion comprising a POI and a vegetable hydrophobic protein, preferably zein, in water miscible non-volatile organic solvent, particularly PG, with a vegetable hydrophobic protein non-solvent, preferably an aqueous medium, under mild stirring for a suitable period of time, at room temperature, for example, from 1 to 30 minutes, typically, less than 15 minutes, preferably around 5 minutes if it is necessary to use stirring.

The POI:non-volatile water miscible solvent ratio by weight in volume (mg/mL), can vary within a broad range; nevertheless, in a particular embodiment, said POI:non-volatile water miscible solvent, is comprised between $0.001:1$ and $10^4:1$, preferably between $0.01:1$ and $50:1$.

The particulars of the POI have been previously mentioned in the "Definitions" section; nevertheless, in this case, the POI should be of water immiscible characteristics and able to form a solution, suspension or emulsion in a water miscible non-volatile solvent containing a vegetable hydrophobic protein. Thus, in a particular embodiment, the POI is an oil or solid fats, for example, an essential oil, mineral oil, solid fats (i.e., wax). In another particular embodiment, the POI is dissolved, suspended or emulsified in a water miscible solvent, for example, a polyol, such as PG and thus forming one phase solution or two phase emulsion, etc. Thus, virtually any POI capable of being dissolved, dispersed or emulsified in a water miscible non-volatile solvent, comprising a vegetable hydrophobic protein, can be used within the context of process [3] of the invention.

In a specific embodiment, said POI is a drug or a cosmetical or food product being dissolved, dispersed or emulsified in a water miscible non-volatile solvent comprising both POI and a vegetable hydrophobic protein, preferably zein.

In a specific embodiment, said POI can include a drug or a cosmetical or food product being dissolved, dispersed or emulsified in another POI.

According to process [3] of the invention, a non-volatile water miscible organic solvent comprising a POI in a form of solution or suspension or emulsion and a vegetable hydrophobic protein, e.g., an oily solution, suspension or emulsion, is contacted with a vegetable hydrophobic protein non-solvent, preferably an aqueous medium, i.e., a medium comprising water, non-solvent, optionally in the presence of a surfactant, in order to form the core-shell vesicular nanocapsules loaded with said POI ("POI-loaded shell core-shell vesicular nanocapsules"). In a particular embodiment, the protein non-solvent comprises water, preferably, distilled or bidistilled water. The volume ratio of the (solution or suspension or emulsion comprising the POI and the vegetable hydrophobic protein, preferably zein):protein non-solvent phase can vary within a broad range, for example, between 1:0.5 and 1:10$^6$ (v/v), preferably 1:0.5 and 1:1000 (v/v), more preferably between 1:50 and 1:100, and even more preferably between 1:2 and 1:10.

In a preferred embodiment the medium further comprises a surfactant and/or a polyanionic polymer.

Although it is not necessary to use surfactants for producing the core-shell vesicular nanocapsules provided by the instant invention, in practice it may be of interest to use a surfactant, e.g., a hydrophilic, hydrophobic or mixtures thereof, in order to obtain the suitable HLB. Illustrative, non-limitative, examples of surfactants which can be used within the context of the present invention include non-ionic surfactants, for example, polysorbates (i.e., oily liquids derived from pegylated sorbitan esterified with fatty acids, e.g., lauric acid, palmitic acid, stearic acid, oleic acid, etc.; esters of plain (non-PEG-ylated) sorbitan with fatty acids are usually referred to by the name "Span"), polyoxyethylene derivative of sorbitan monolaurate (Tween® 20), polyoxyethylene derivative of sorbitan oleate (Tween® 80), etc., anionic surfactants, e.g., sodium dodecyl sulfate (SDS), etc., block copolymers based on ethylene oxide and propylene oxide commercialized as Pluronics® by BASF, polyvinylic alcohol (PVA), etc. In a particular embodiment, the surfactant is TPGS (alpha-tocopheryl succinate esterified to PEG1000). The amount of the surfactant can vary within a broad range; nevertheless, in a particular embodiment, the concentration of surfactant is comprised between 0.001% and 50% (w/v), preferably between 0.01% and 10% (w/v), more preferably between 0.05% and 5% (w/v).

This step is performed at a suitable temperature, typically comprised between 1° C. and 100° C., preferably, between 15° C. and 50° C.

The solution, suspension or emulsion containing a vegetable hydrophobic protein and a product of interest dissolved, suspended or emulsified in a medium, said medium comprising at least a water miscible non-volatile organic solvent and, optionally, a surfactant and, optionally, an aqueous medium, wherein the amount of aqueous medium is lower than the necessary amount of aqueous medium to form nanoparticles, wherein the medium comprising at least a water miscible non-volatile organic solvent does not comprise a volatile organic solvent and wherein the amount of vegetable hydrophobic protein is comprised between 0.01% and 50% (w/v), preferably between 0.01% and 40% (w/v), more preferably between 0.01% and 30% (w/v), still more preferably between 0.01% and 20% (w/v), still more preferably between 0.01% and 15% (w/v), even more preferably between 0.01% and 10% (w/v), even more preferably between 0.01% and 5% (w/v), the most preferred between 0.01% and 2.5% (w/v) constitutes an additional aspect of the present invention. In a preferred embodiment the vegetable hydrophobic protein of said solution, suspensior or emulsion is selected from hordein, secalin, zein, kafirin, panicin, orzenin and avenin; more preferably is selected from hordein, secalin, zein, kafirin and avenin; even more preferably is selected from zein, hordein and kafirin; the most preferred being zein. In another embodiment, the amount of vegetable hydrophobic protein in said solution, suspension or emulsion is higher than 0.1% (w/v), at least 0.2% (w/v), at least 0.5% (w/v), at least 1% (w/v), at least 5% (w/v), at least 10% (w/v), at least 15% (w/v), at least 20% (w/v), at least 25% (w/v), at least 30% (w/v), at least 35% (w/v), at least 40% (w/v) and not more than 50% (w/v). In another embodiment the amount of vegetable hydrophobic protein is comprised between 0.01% and 50% with the proviso that when the vegetable hydrophobic protein is gliadin, then the amount of vegetable hydrophobic protein is higher than 0.1%. Said solution, suspension or emulsion must be able to form vegetable hydrophobic protein nanoparticles when mixed with appropriate amount of vegetable hydrophobic protein non-solvent, preferably water. Said organic solution, suspension or emulsion can be used to produce POI-loaded nanoparticles, mainly core-shell nanocapsules wherein said shell comprises a vegetable hydrophobic protein and at least a water miscible non-volatile organic solvent, after entering into contact with a vegetable hydrophobic protein non-solvent, preferably an aqueous medium, preferably with a biological fluid. In a particular embodiment, the water miscible non-volatile organic solvent is propylene glycol, and the protein non-solvent comprises water, and preferably is a biological fluid. In a preferred embodiment, the medium comprises a binary or ternary mixture of a water miscible non-volatile organic solvent. In a preferred embodiment, the vegetable hydrophobic protein is a prolamine, preferably zein. In a preferred embodiment the water miscible non-volatile organic solvent is a polyol, preferably is a glycol, more preferably propylene glycol. In a preferred embodiment, the solution or suspension further comprises a surfactant and/or a polyanionic polymer.

If desired, the nanoparticles of the invention, both those that are loaded with a POI (POI-loaded nanoparticles) and those that are not loaded ("empty" nanoparticles), may incorporate an antioxidant, e.g., ascorbic acid (vitamin C), etc., in their formulation for the purpose of increasing their stability with regard to temperature and oxidation. In this case, said antioxidant could be co-encapsulated with the POI (where appropriate) or in the coating of the nanoparticles of the invention; to that end, said processes [1] to [3] of the invention will be suitably adapted to incorporate the antioxidant in the formulation of the nanoparticles, for example, by adding the antioxidant to the protein non-solvent medium, preferably aqueous medium, used for producing the nanoparticles.

Additionally, if desired, said process [1], [2] and [3] of the invention may include an anionic molecule or polymer, for example, anionic poly saccharides (e.g, pectin, arabic gum) or polyanionic salts that can be associated to the nanoparticles of the invention to obtain anionic nanoparticles. Said anionic nanoparticles may be obtained by coating nanoparticles with said anionic molecules or polymers or by complexation of the anionic molecules or polymers in the matrix or shell of the nanoparticles.

Additionally, if desired, said processes [1], [2] and [3] of the invention may include a drying step for drying the suspension containing the nanoparticles so formed, in order to obtain the nanoparticles of the invention, i.e., both the POI-loaded nanoparticles and the "empty" nanoparticles, in the form of a powder. In a particular embodiment said drying step is performed by lyophilization. This form of presentation of said nanoparticles contributes to their stability and is further particularly useful for their eventual application in solid foods, such as flour, bread, pastry products, cereals, milk powder, etc., as well as in cosmetic and/or pharmaceutical compositions and products.

Virtually any conventional technique or method suitable for drying suspensions containing nanoparticles can be used to perform this drying step; however, in a particular embodiment, the drying of the suspension containing nanoparticles is carried out by means of spray drying or by means of lyophilization. This treatment is generally carried out by adding a suitable protective agent of said nanoparticles, such as a saccharide, for example, lactose, trehalose, mannitol, sucrose, maltodextrine, glucose, sorbitol, maltose, etc., and mixtures thereof to the suspension of the nanoparticles. Said protective agent protects the nanoparticles of the invention against heat degradation as well as oxidation during the drying process.

The "vegetable hydrophobic protein, preferably zein:saccharide" ratio by weight may vary within a broad range; however, in a particular embodiment, the "vegetable hydrophobic protein, preferably zein:saccharide" by weight is comprised between 1:1 and 1:1000, preferably about 1:1-5.

Likewise, in a particular embodiment, the solution containing the saccharide could further contain an antioxidant agent, such as ascorbic acid (vitamin C), etc.; in this case the "vegetable hydrophobic protein, preferably zein:saccharide:antioxidant agent", ratio by weight could be from 1:0.01-1000:0.001-100, preferably about 1:1-5:0.2.

As mentioned above, the skilled person in the art will understand that a loaded nanoparticle of the invention can incorporate one or more POI in the same nanoparticle provided that said POIs are not incompatible each other. To that end, process [1], [2] and [3] will be properly modified to incorporate the POIs in the same solution of water miscible non-volatile organic solvent comprising the vegetable hydrophobic protein, or in the same solution, suspension or emulsion comprising the vegetable hydrophobic protein and other POI, or, alternatively, in different preparations.

The nanoparticles of the invention obtained according to process [1], [2] or [3] of the invention constitute an additional aspect of the present invention.

A further aspect of the invention is a suspension of nanoparticles according to the invention in a medium, said medium comprising at least a water miscible non-volatile organic solvent and a vegetable hydrophobic protein non-solvent medium, preferably an aqueous medium, and not comprising a volatile organic solvent.

Applications

The nanoparticles of the invention have a lot of properties which make them potentially useful in a wide variety and diversity of industries, for example, in the pharmaceutical, cosmetic, agricultural or food industries, as a system for the delivery of products of interest to different surfaces, e.g., buccal, gastrointestinal tract, hair, nasal, oral, rectal, skin, vaginal, etc.

It has been considered an important advantage the spontaneous formation of the nanoparticles based on a vegetable hydrophobic protein by an in situ self-assembly technique. This would allow the fabrication of big industrial batches of nanoparticles for the delivery of products of interest to different applications.

Illustrative, non-limitative, examples of said properties of the nanoparticles of the invention include the facility to obtain the nanoparticles without the use of volatile organic solvents and sonication to dissolve hydrophobic proteins or evaporation technique applied to eliminate these solvents. This would allow the direct addition of the freshly prepared nanosystems to any final product. In addition, the self-assembled zein nanoparticles have a high capacity to incorporate different types of molecules with different physicochemical properties including high encapsulation efficiency of products of interest, such as small or large, hydrophilic, hydrophobic or amphiphillic compounds. The use of one water miscible non-volatile organic solvent or a mixture of them, that have a high solubility power for zein and other vegetable hydrophobic proteins, can act as plasticisers to enhance the bioadhesive capacity to the mucosal surfaces and thus allowing the effective mucosal drug delivery. In addition, an interesting application is related to the possibility of the direct administration of a vegetable hydrophobic protein solution, suspension or emulsion containing POI into the body fluids which would allow the in situ formation of the nanoparticles and subsequent entrapment of the molecule, for example a subcutaneous injection of a biocompatible water miscible non-volatile organic solvent containing a vegetable hydrophobic protein, preferably zein, and therapeutic molecules for delivery would allow the in situ formation of nanoimplants.

In a particular embodiment, the nanoparticles of the invention allow the direct incorporation of a POI, in agricultural, cosmetic, food or pharmaceutical compositions.

The nanoparticles of the invention can be presented in the form of a suspension, preferably in an aqueous medium, or, alternatively, they can be presented in the form of a dry powder, maintaining the POI in a stable condition and enabling its storage for long periods of time (particularly, for its incorporation in solid food preparations).

Therefore, in another aspect, the invention relates to a composition, hereinafter "composition of the invention", comprising at least one nanoparticle of the invention or a solution, suspension or emulsion according to the invention, or a suspension of nanoparticles according to the invention and a carrier, particularly an agricultural, cosmetically or pharmaceutically acceptable carrier or a carrier suitable for food.

In a preferred embodiment the composition is selected from a pharmaceutical composition, a cosmetic composition, an agricultural composition and a food composition.

In a particular embodiment, the particle of the invention is an "empty" nanoparticle of the invention, i.e., a nanoparticle of the invention without a POI, such as i) a matrix nanosphere which comprises a matrix, said matrix comprising a vegetable hydrophobic protein, preferably zein, and at least a water miscible non-volatile organic solvent. In another particular embodiment, the particle of the invention is a core-shell vesicular nanocapsule, wherein said core-shell vesicular nanocapsule comprises a core and a shell, said shell comprising a vegetable hydrophobic protein and at least a water miscible non-volatile organic solvent, and wherein said core-shell vesicular nanocapsule comprises a core, said core comprising a excipient in solid, semisolid or liquid state.

In another particular embodiment, the nanoparticle of the invention is a "loaded" nanoparticle of the invention, i.e., a nanoparticle of the invention loaded with a POI, such as (i) a matrix nanosphere which comprises a POI and a matrix, said matrix comprising a vegetable hydrophobic protein, preferably zein, and at least a water miscible non-volatile organic solvent, (ii) a core-shell vesicular nanocapsule which comprises a POI in the core and a shell, said shell comprising a vegetable hydrophobic protein, preferably zein, and at least a water miscible non-volatile organic solvent, or (iii) a combination of (i) and (ii). In a particular embodiment, said POI is a POI having agricultural, cosmetic, nutritional, and/or therapeutic activity. The particulars of said POI have been mentioned in the "Definitions" section.

In another particular embodiment, the composition of the invention is an agricultural composition; to that end, said composition comprises a "loaded" nanoparticle of the invention comprising a POI susceptible of being used in the agricultural field, in the broadest sense, for example, a phytosanitary product for controlling pests and pathogens, a plant growth promoting agent, etc., for example, an herbicide (glyphosate, etc.), an insecticide (e.g., lambda-cyhalothrin, etc.), a fungicide (e.g., Mancozeb), etc., or an antitranspirant in case of "empty" nanoparticles, etc., and an agriculturally acceptable carrier comprising one or more excipients suitable for its application; the agricultural composition can be formulated in the form of a gel, suspension, etc., by using the carriers known by the skilled person in the art.

In another particular embodiment, the composition of the invention is a cosmetic composition; to that end, said composition comprises "empty" nanoparticles of the invention, e.g., empty nanoparticles for use in hair styling products such as hair fixatives, styling, etc., or "loaded" nanoparticles of the invention comprising a POI having cosmetic activity or susceptible of being used with cosmetic purposes, or mixtures thereof, and a cosmetically acceptable carrier comprising one or more excipients suitable for its administration by a suitable route, such as, for example, by the topical route; the cosmetic composition can be formulated in the form of skin-care creams, lotions, powders, perfumes, lipsticks, fingernail and toe nail polish, eye and facial makeup, towelettes, permanent waves, colored contact lenses, hair colors, hair sprays and gels, deodorants, hand sanitizer, baby products, bath oils, bubble baths, bath salts, suspensions, butters and many other types of products. Information about excipients suitable for the formulation of cosmetic compositions as well as about the production of said cosmetic compositions can be found in the book "Manual de Cosmetologia", by Octavio Díez Sales, 1st Edition, 1998, Editorial Videocinco, S. A. Illustrative, non-limitative, examples of POI used in the cosmetic industry include the products already mentioned in the "Definitions" section.

In another particular embodiment, the composition of the invention is a food composition, such as a solid, liquid or semi-solid food preparation; to that end, said composition comprises a "loaded" nanoparticle of the invention comprising a POI having nutritional activity and a carrier for use in food. Alternatively, the composition of the invention can be incorporated into a foodstuff; therefore, in another aspect, the invention relates to a foodstuff comprising a composition of the invention, namely, a composition which comprises a "loaded" nanoparticle of the invention, said nanoparticle comprising a POI having nutritional activity and a carrier for use in food. The foodstuff can be found in liquid, semi-solid or solid form. Illustrative examples of foodstuffs that can be enriched or fortified with the composition of the invention include milk and derivatives thereof (yoghurts, cheeses, curds, etc.), juices, jams, bakery and pastry products, bread, fermented meat, sauces, etc. Similarly, the composition of the invention can be incorporated into an animal food product, for example, in feeds. In a particular embodiment, the foodstuff is a nutraceutical (i.e. a product derived from food sources that provides extra health benefits in addition to the basic nutritional value found in foods), particularly a functional food, i.e. a food where a new ingredient or an existing ingredient has been added to resulting in a new product having a new function often related to health-promotion or disease prevention.

In another particular embodiment, the composition of the invention is a pharmaceutical composition; to that end, said composition comprises a "loaded" nanoparticle of the invention comprising a POI having therapeutic activity or susceptible of being used with therapeutic purposes, and a pharmaceutically acceptable carrier which comprises one or more excipients or vehicles. The POI which is present in the "loaded" nanoparticle of the invention can be trapped or encapsulated within the nanoparticle (i.e., nanosphere or nanocapsule) or, alternatively, the product of interest can be adsorbed on or conjugated to the surface of the nanoparticle.

Examples of pharmaceutical compositions include liquid, solid or semi-solid compositions.

The pharmaceutical compositions will comprise suitable excipients for each formulation and will be conventionally prepared by methods known by the persons skilled in the art. The excipients will be chosen according to the selected pharmaceutical dosage form. A review of the different pharmaceutical dosage forms of drugs and of their preparation can be found in the book "Tratado de Farmacia Galénica", by C. Faulí i Trillo, 10 Edition, 1993, Luzán 5, S. A. de Ediciones.

The dose of "loaded" nanoparticles of the invention to be administered to a subject in need of treatment with the POI can vary within a broad range and will depend, among other features, on the nature of the POI, its activity or potency, the amount of POI per nanoparticles, etc.; only by illustrative purposes, the dose of "loaded" nanoparticles to be administered to a subject may be comprised, for example, between approximately 0.01 and approximately 100 mg per kg of body weight per day, preferably, between 0.1 and 2 mg per kg of body weight per day.

In a particular embodiment, said pharmaceutical composition is formulated as a pharmaceutical dosage form suitable for its administration by any suitable route, for example, by the buccal, dental, nasal, ocular, oral, parenteral, rectal, topical, or vaginal route. Illustrative, non-limitative, examples of said pharmaceutical dosage forms include solid (e.g., soft or hard gelatin and non-gelatin capsules, adhesive films, dental adhesives parches, suppositories, tablets, granules, microparticles, etc.), semisolids (e.g., creams, gels, lotions, ointments, etc.), liquids (e.g., solutions, suspensions, emulsions, etc.). In a preferred embodiment, due to the bioadhesive properties of the nanoparticles of the invention, the pharmaceutical composition is formulated in the form of a composition for its administration through a route of access to mucosae.

In a specific embodiment, the pharmaceutical composition is formulated as a pharmaceutical form suitable for its administration by the rectal route (suppositories), by the vaginal route (ovules), or by the oral or parenteral (e.g., s.c., or intravitreal) routes; if desired, in this embodiment, the nanoparticles can be formed when the solution, suspension or emulsion comprising the POI, the vegetable hydrophobic protein, preferably zein, and the water miscible non-volatile organic solvent, contacts with a body fluid, e.g., the vaginal fluid, gut fluids and others. Thus, in a preferred embodiment the carrier of the composition comprises a pharmaceutically acceptable excipient for the administration thereof by the buccal, dental, nasal, ocular, intravitreal, oral, parenteral, rectal, topical, or vaginal routes, or a cosmetically acceptable excipient for the administration thereof by topical route.

In a particular embodiment, the composition is a cosmetic composition or a pharmaceutical composition suitable for its administration by the buccal, dental, nasal, ocular, oral, parenteral, rectal, topical, or vaginal route.

In another particular embodiment, the composition of the invention is prepared in the form of a dry powder, for example as a lyophilizate, together with a cryoprotecting agent, to be reconstituted before use by mixing with the reconstitution agent.

In a specific embodiment, the invention provides a pharmaceutical composition in the form of solution, suspension or emulsion comprising:

| Component | % by weight with respect to total volume |
|---|---|
| Vegetable hydrophobic protein (zein) | 0.01-50 |
| POI* | 0.001-99.988 |
| water miscible non-volatile organic solvent/s | 0.001-99.98 |
| vegetable hydrophobic protein non-solvent (water) | 0.00-15% |

*The POI may be any POI as defined in the "Definitions" section including excipients. Said pharmaceutical composition is suitable for the in situ formation of the nanoparticles after contact with body fluids.

In another specific embodiment, the invention provides a pharmaceutical composition in the form of a suspension of nanoparticles comprising:

| Component | % by weight with respect to total volume |
|---|---|
| Vegetable hydrophobic protein (zein) | 0.01-50 |
| POI* | 0.001-99.988 |
| water miscible non-volatile organic solvent/s | 0.001-75 |
| anionic polymer | 0.00-10 |
| vegetable hydrophobic protein non-solvent | 15.00-99.98 |

*The POI may be any POI as defined in the "Definitions" section including excipients.

The "loaded" nanoparticles of the invention, in particular, those nanoparticles loaded with a POI wherein said POI is a drug, can be used in the treatment of diseases. The drug will be selected in function of the disease to be treated. Therefore, in another aspect, the invention relates to a nanoparticle of the invention loaded with a POI, wherein said POI is a drug, for use in medicine. Therefore, in another aspect, the invention relates to the use of a nanoparticle of the invention loaded with a POI, wherein said POI is a drug, in the manufacture of a medicament for the prevention and/or treatment of a disease, or, alternatively, the invention relates to a nanoparticle of the invention loaded with a POI, wherein said POI is a drug, for use as a medicament or in the treatment and/or prevention of a disease. Furthermore, the invention also relates to a method of treatment or prevention of a disease in a subject comprising the administration to said subject of a nanoparticle of the invention loaded with a POI, wherein said POI is a drug.

The invention also relates to a solution, suspension or emulsion of a vegetable hydrophobic protein in an amount comprised between 0.01% and 50% (w/v) and a POI in a water miscible non-volatile organic solvent and, optionally, a surfactant or/and a polyanionic polymer, and, optionally, an aqueous medium, wherein the amount of aqueous medium is lower than the necessary amount of aqueous medium to form nanoparticles; wherein the POI is a drug and wherein said solution, suspension or emulsion does not comprise a volatile organic solvent for use in medicine or in the treatment and/or prevention of a disease. Alternatively, in other words, the invention relates to the use of a solution, suspension or emulsion of a vegetable hydrophobic protein in an amount comprised between 0.01% and 50% (w/v) and a POI in a water miscible non-volatile organic solvent and, optionally, a surfactant or/and a polyanionic polymer, and, optionally, an aqueous medium, wherein the amount of aqueous medium is lower than the necessary amount of aqueous medium to form nanoparticles; wherein the POI is a drug and wherein said solution, suspension or emulsion does not comprise a volatile organic solvent, in the manufacture of a medicament for the prevention and/or treatment of a disease. Furthermore, the invention relates to a method of treatment or prevention of a disease in a subject comprising the administration to said subject of a solution, suspension or emulsion of a vegetable hydrophobic protein in an amount comprised between 0.01% and 50% (w/v) and a POI in a water miscible non-volatile organic solvent and, optionally, a surfactant or/and a polyanionic polymer, and, optionally, an aqueous medium, wherein the amount of aqueous medium is lower than the necessary amount of aqueous medium to form nanoparticles; wherein the POI is a drug and wherein said solution, suspension or emulsion does not comprise a volatile organic solvent. In a preferred embodiment, said solution, suspension or emulsion contains an amount of a vegetable hydrophobic protein comprised between 0.01% and 40% (w/v), preferably between 0.01% and 30% (w/v), more preferably between 0.01% and 20% (w/v), still more preferably between 0.01% and 15% (w/v), even more preferably between 0.01% and 10% (w/v), even more preferably between 0.01% and 5% (w/v), the most preferred between 0.01% and 2.5% (w/v). In a preferred embodiment the vegetable hydrophobic protein of said solution, suspension or emulsion is selected from hordein, secalin, zein, kafirin, panicin, orzenin and avenin; more preferably is selected from hordein, secalin, zein, kafirin and avenin; even more preferably is selected from zein, hordein and kafirin; the most preferred being zein. In another embodiment, the amount of vegetable hydrophobic protein in said solution, suspension or emulsion is higher than 0.1% (w/v), at least 0.2% (w/v), at least 0.5% (w/v), at least 1% (w/v), at least 5% (w/v), at least 10% (w/v), at least 15% (w/v), at least 20% (w/v), at least 25% (w/v), at least 30% (w/v), at least 35% (w/v), at least 40% (w/v) and not more than 50% (w/v). In another embodiment the amount of vegetable hydrophobic protein is comprised between 0.01% and 50% with the proviso that when the vegetable hydrophobic protein is gliadin, then the amount of vegetable hydrophobic protein is higher than 0.1%.

In a particular embodiment, the drug is the antimicrobial chlorhexidine, and, thus, the invention relates to the use of a cationic bioadhesive nanoparticle of the invention loaded with chlorhexidine in the manufacture of a medicament for the treatment and prevention of buccal or external body infections or, alternatively, in other words, a nanoparticle of the invention loaded with chlorhexidine for use in the treatment and prevention of buccal or external body infections. Alternatively, the invention also relates to a method of treatment or prevention of buccal or external body infections in a subject comprising the administration to said subject of a nanoparticle of the invention loaded with chlorhexidine.

In a particular embodiment, the molecule is useful in functional food, specifically is the antioxidant curcumin and, thus, the invention relates to the use of a nanoparticle of the invention loaded with curcumin as food additive and antioxidant to improve human and animal health.

In another particular embodiment, the molecule is an essential oil (aroma) and, thus, the invention relates to the use of a nanoparticle of the invention loaded with essential oils (aromas) in food, cosmetic, agriculture and pharmaceutical fields.

In another particular embodiment, the molecule is an omega fatty acid or oil and, thus, the invention relates to the use of a nanoparticle of the invention loaded with omega fatty acids or oils as dietary supplement.

In another particular embodiment, the invention relates to a cationic loaded and empty nanoparticle of the invention for use in the agglutination, capture or attachment to the surface of anionic soluble molecules, anionic microorganisms (i.e., yeast, bacteria, virus, fungi, etc.), or any anionic particles.

The invention is described below by means of several examples which do not limit, but rather illustrate the invention.

EXAMPLES

The following examples describe the production of nanoparticles (matrix nanospheres and core-shell vesicular nanocapsules), based on the vegetable hydrophobic protein zein, that may incorporate a product of interest, for example, an oil or aroma (e.g., lemon or peppermint essential oil, cod liver oils, oleic acid, linolenic acid), a protein (e.g., bovine serum albumin (BSA)), a drug (e.g., chlorhexidine), or a food antioxidant (e.g., curcumin). Said examples show that said nanoparticles have high mucosal bioadhesion, facility of the industrial scale process, high encapsulation efficiency of products of interest, such as small or large, hydrophilic, hydrophobic or amphiphillic compounds, high encapsulation efficiency of oils, and that the nanoparticles enhance the solubility in water of hydrophobic compounds.

The materials used for the production of said nanoparticles are described below.

Materials

Zein, linolenic acid, curcumin, fluorescein isothiocyanate labelled bovine serum albumin (FITC-BSA) and lipophilic fluorescent probe 1,1'-dioctadecyl-3,3,3',3'-tetramethylindocarbocyanine perchlorate were supplied from Sigma (Spain).

Medium chain triglycerides (Labrafac™ CC) was a gift sample provided by Gattefosse (Gennevilliers, France).

Labrasol® was supplied by Gattefosse.

Arabic gum, chlorhexidine, *Mentha piperita* (Peppermint) oil, cinnamon oil, thyme oil, eugenol, Tween® 20, Tween® 80, glycerol and propylene glycol were supplied by Fagron.

Lutrol® L 44 was a kind gift from BASF.

All the other chemical reagents including excipients were of analytical grade and supplied by Sigma (Spain).

Example 1

Preparation and Characterization of Empty Self-Assembled Zein Nanoparticles (ZSNP) at Small and Large Scale

1.1 Preparation of Cationic and Anionic Empty Self-Assembled Zein Nanoparticles To obtain empty cationic ZSNP, at small scale, zein was dissolved in propylene glycol (PG) at different zein concentrations (0.5, 1, 2.5, 5 and 10% (w/v)). Then, the nanoparticles were formed by mixing 1 mL of said zein-propylene glycol solution with 5 mL of bidistilled water as propylene glycol miscible zein non-solvent. Thus the zein was precipitated in the form of matrix nanoparticles.

For large scale production, 5 L of zein-propylene glycol solution, at a concentration of 5% (w/v), were poured at a constant flow of 250 mL/min into 25 L of bidistilled water in a reactor at room temperature under mild agitation.

Nanoparticles prepared by a traditional method were obtained according to the previously described protocol with slight modifications [29]. For this purpose, 100 mg of zein were dissolved in 5 mL of 70% ethanol (w/w) ultrasonically. The resulting solution was immediately added in 7.5 mL of distilled water. Then the resulting nanoparticles suspension was evaporated under reduced pressure using a rotavapor (Büchi R-144, Switzerland) to eliminate ethanol.

In order to obtain anionic zein nanoparticles, 1 mL of the zein solution in propylene glycol (5% w/v) was mixed with 5 mL of bidistilled water as PG miscible zein non-solvent. Then, 1 mL of anionic polymer (arabic gum at 0.25% w/v) was added to zein nanoparticles suspension under magnetic stirring. After that, the mixture was left under magnetic agitation for 5 min at room temperature. In a similar way, a direct complexation process was applied to obtain zein nanoparticles. For this purpose, 1 mL of the zein solution in propylene glycol (5% w/v), was added to 5 mL of an aqueous solution of anionic polymer (arabic gum at 0.04% w/v) as PG miscible zein non-solvent.

In both types of nanoparticles, the resulting nanoparticles suspension were centrifuged twice at 27,000×g for 20 min and then were collected for further characterization.

1.2 Characterization of Empty Zein Nanoparticles

1.2.1 Size, Zeta Potential, Yield and Morphology of the Nanoparticles

The size and zeta potential of the nanoparticles were determined by photon correlation spectroscopy and electrophoretic laser Doppler anemometry, respectively, using a Zetamaster analyser system (Malvern Instruments, UK). Samples were diluted with bidistilled water and measured at 25° C. with a scattering angle of 90°.

The yield of the nanoparticles preparation process, which is the percent of zein transformed into nanoparticles, was determined by gravimetry from freeze-dried samples as described previously [38]. For this purpose, the aqueous suspensions of the obtained nanoparticles were centrifuged twice at 27,000×g for 20 min (Sigma lab centrifuge, Rotor 3336, Biofuge Heraeus, Germany), recollected and lyophilized in a Genesis 12EL apparatus (Virtis, USA). The percentage yield of the nanoparticles (the amount of zein transformed into nanoparticles) was calculated as the ratio between the dry lyophilized nanoparticles samples and the initial amount of the zein used to prepare the formulations.

The morphological characteristics of the nanoparticles were visualized by transmission electron microscopy (TEM) in an electron microscope Zeiss Libra® 120 (Oberkochen, Germany).

1.3 Results

1.3.1 Characterization of Empty Zein Nanoparticles

Table 1 shows the main physico-chemical characteristics of both ZSNP of the invention prepared at small (ZSNP-0.5, ZSNP-1, ZSNP-2.5, ZSNP-5, ZSNP-10) and large scale (ZSNP-5 large scale) and zein nanoparticles prepared by a traditional solvent evaporation method (Z-NP-1 TRAD) [29]. Generally, cationic empty self-assembled zein nanoparticles displayed a homogenous size and positive surface charge. Transmission electron microscopy corroborated the size of the nanoparticles and nanoparticles were found to be spherical (FIG. 1). The positive surface charge was increased by increasing the concentration of zein. There was no significant difference between the size and zeta potential for ZSNP prepared at small or large scale. The percentage yield of the nanoparticles was very high for all formulations (about 98%). It has been observed that in case of ZSNP at high concentrations of zein (ZSNP-5 and ZSNP-10), a small percent of aggregates were formed. On the other hand, coating zein nanoparticles with anionic polymers (ZSNP-5 AG) or complexation of the anionic polymer (arabic gum) in the matrix of zein nanoparticles (ZSNP-5 AG complex) significantly increased the particles size to be around 200 to 250 nm compared to non coated or non complexed ones. Arabic gum coated nanoparticles (ZSNP-5 AG and ZSNP-5 AG complex) have homogeneous negative surface charges.

TABLE 1

Physico-chemical characteristics of ZSNP.
Data expressed as mean ± SD (n = 6)

| | $^a$Size (nm), (±SD) Peak and percentage | | | | $^b$PDI | $^c$Zeta potential (mV), (±SD) | $^d$% yield, (±SD) |
|---|---|---|---|---|---|---|---|
| | Peak 1 (nm) | % | Peak 2 (nm) | % | | | |
| ZSNP-0.5 | 111.08 (0.21) | 100% | | | 0.115 | +6.67 (0.11) | 97.12 (2.21) |
| ZSNP-1 | 125.03 (1.22) | 100% | | | 0.103 | +24.21 (0.06) | 97.83 (1.35) |
| ZSNP-2.5 | 143.86 (2.11) | 100% | | | 0.123 | +34.90 (0.20) | 99.10 (2.29) |
| ZSNP-5 | 173.65 (4.22) | 95% | 3073.65 (22.31) | 5% | 0.230 | +32.84 (1.79) | 96.12 (3.90) |
| ZSNP-10 | 211.81 (2.12) | 83% | 7314.65 (11.21) | 17% | 0.378 | +38.85 (1.12) | 97.70 (2.10) |
| ZSNP-5 AG | 198.97 (5.37) | 95% | 1823.12 (27.77) | 5% | 0.211 | −6.23 (0.32) | 96.10 (1.13) |
| ZSNP-5 AG complex | 250.11 (3.12) | 94% | 3453.33 (23.01) | 6% | 0.291 | −8.14 (0.66) | 97.35 (2.55) |
| Z-NP-1 TRAD | 188.44 (5.62) | 94% | 2923.12 (13.33) | 6% | 0.178 | +33.28 (0.42) | 96.00 (0.77) |
| ZSNP-5 large scale | 173.97 (5.32) | 96% | 2132.10 (25.69) | 4% | 0.238 | +32.76 (0.52) | 95.13 (2.15) |

ZSNP-0.5 to ZSNP-10: Self-assembled zein nanoparticles prepared from different concentrations of zein solution in propylene glycol (0.5, 1, 2.5, 5 and 10% w/v) prepared at small scale
ZSNP-5 AG: Self-assembled zein nanoparticles coated with arabic gum
ZSNP-5 AG complex: Self-assembled zein nanoparticles prepared by complexation between zein and arabic gum
Z-NP-1 TRAD: Zein nanoparticles obtained by a traditional solvent replacement method [29]
ZSNP-5 large scale: Self-assembled zein nanoparticles prepared at large scale
$^a$Determination of the nanoparticles size (nm) by photon correlation spectroscopy.
$^b$Polydispersity Index.
$^c$Determination of the zeta potential by electrophoretic laser Doppler anemometry.
$^d$Percentage of the nanoparticles formed from the initial amount of the zein protein used.

Example 2

Preparation and Characterization of Self-Assembled Zein Nanoparticles Obtained from Different Solvent Mixtures Biocompatible and biodegradable non-toxic mixtures of solvents were also used to obtain self-assembled zein nanoparticles (ZSNP). As example, a binary mixture of propylene glycol and PG miscible non-volatile solvents (i.e., water or glycerol) or other liquid surfactants that are miscible with propylene glycol, such as Labrasol® (Caprylocaproyl polyoxyl-8 glycerides NF), nonionic polyoxyethylene-polyoxypropylene copolymers (liquid Lutrol® L 44 (Poloxamer USP-NF)) or Tween® 80 were used, at a concentration that kept zein soluble in PG.

2.1 Determination of Solubility of Zein in Water Miscible Non-Volatile Solvent Binary Mixtures The solubility of zein in different binary mixtures of PG and other water miscible non-volatile organic solvents that are miscible with PG was studied. This example studies the incorporation of different surfactants or solvents to enhance the solubility of a molecule in PG, if necessary. For this purpose, turbidity change of PG zein solution was monitored at 405 nm after the addition of different amounts of water, glycerol, Labrasol®, Tween® 80 or Lutrol® L 44 to 5 mL of zein solution in PG (2.5% w/v), at room temperature. The end point zone, at which zein was precipitated from PG solution, was calculated monitoring the turbidity change at 405 nm, that is, the absorbance increase (in percentage) after each solvent/surfactant addition with respect to the initial absorbance value in a spectrophotometer (Labsystems iEMS Reader MF, Finland).

2.2 Preparation and Characterization of Self-Assembled Zein Nanoparticles Obtained from Binary Miscible Non-Volatile Solvent Mixtures In order to obtain ZSNP from PG binary solvent mixtures, 5 mL of zein in propylene glycol solution (zein PG) was prepared at different concentrations. Then, different amounts of secondary solvents that are miscible with PG such as glycerol (2 mL), water (0.8 mL), Labrasol® (3 mL), Tween® 80 (3 mL) and Lutrol® L 44 (1.2 mL) were added to zein PG solution. The final zein concentration was usually kept at 2.5% w/v in the solvent mixture. The volume of the secondary solvents was selected according to the previous study performed to determine the miscibility zone between zein PG and PG miscible non-volatile solvents in which zein was not soluble. Then, the nanoparticles were formed by mixing 1 mL of the zein solvent binary mixture solution with 5 mL of bidistilled water as zein miscible non-solvent. The resulting nanoparticles were characterized as previously described in Example 1.

On the other hand, in order to form ZSNP from PG binary solvent mixtures by adding a zein protein non-solvent other than water, 5 mL of zein in propylene glycol solution (zein PG) was prepared at different concentrations. Then, different amounts of secondary solvents that are miscible with PG such as glycerol (2 mL), Labrasol® (3 mL) and Lutrol® L 44 (1.2 mL) were added to zein PG solution. The final zein concentration was usually kept at 2.5% w/v in the solvent mixture. The volume of the secondary solvents was selected according to the previous study performed to determine the miscibility zone between zein PG and PG miscible non-volatile solvents in which zein was soluble. Then, the nanoparticles were formed by adding the appropriate amount of each secondary solvent to achieve the final volume of 25 mL. The resulting nanoparticles were characterized as previously described in Example 1.

2.3 Results 2.3.1 Solubility of Zein in PG Solvent Mixtures

Figure 2:
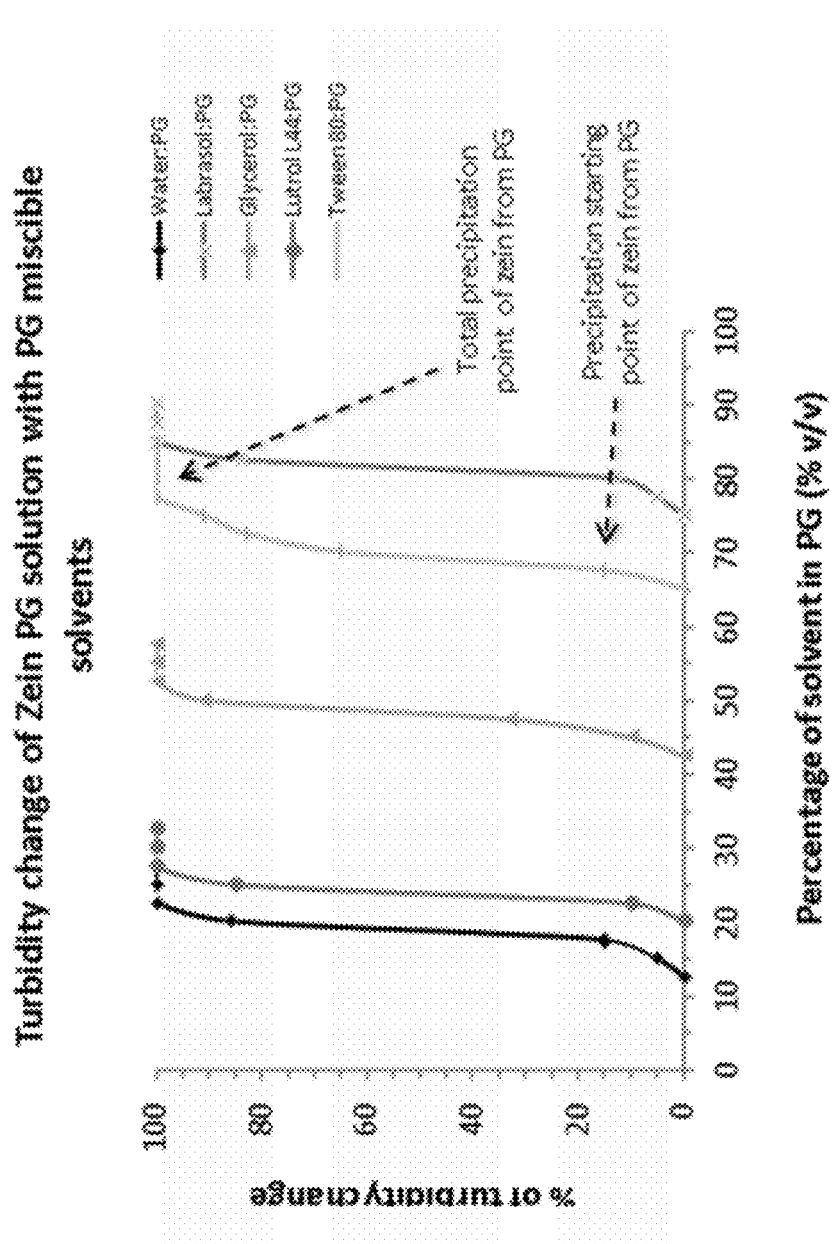

FIG. 2 shows the percentage of turbidity changes monitored by UV at 405 nm after the addition of different percentages (v/v) of PG miscible, non-volatile solvents or surfactants in which zein was not soluble. The end point range shown in FIG. 2, has been considered as a zone at which the percentage of zein non-solvent initiates the precipitation of zein from PG solution to achieve complete precipitation. From this figure, it has been observed that the end point range (represented by the wide range of each curve at x-axis) for both water and Lutrol® L 44 was from 15 to 22.5 and 22 to 28% v/v respectively. This indicated the low solubilization power of both solvents for zein. On the other hand, the percentage of glycerol: PG (v/v) zein solution demonstrated a higher end point range (45-55% v/v). The solubilization capacity of both Labrasol® and Tween® 80 for zein in PG were the highest, approximately from 65-75% (v/v) in the case of Tween® 80 and from 75 to 85% (v/v) in the case of Labrasol®.

2.3.2 Characterization of Self-Assembled Zein Nanoparticles Obtained from Binary Miscible Non-Volatile Solvent Mixtures Table 2 shows the main physico-chemical characteristics of ZSNP prepared from solvent mixtures for zein comprising a zein-PG solution mixed with other solvents such as water (ZSNP-PG:W), glycerol (ZSNP-PG:G), Labrasol® (ZSNP-PG:Lab), Lutrol® L 44 (ZSNP-PG:Lut) and Tween® 80 (ZSNP-PG:T80) formed after the addition of appropriate amount of water as protein non-solvent. ZSNP formed after the addition of a zein non-solvent other than water (Lutrol®, glycerol and Labrasol®) to the zein-PG binary solvent mixture solution were obtained after the addition of glicerol to zein_PG-glicerol binary mixture solution (ZSNP-PG:G/G), of Lutrol® to zein PG-Lutrol® binary mixture solution (ZSNP-PG:Lut/Lut), and of Labrasol® to zein PG-Labrasol® binary mixture solution (ZNSP-PG:Lab/Lab).

All nanoparticles formulations obtained using water as protein non-solvent displayed a size below 200 nm and a homogeneous positive surface charge. In case of ZSNP prepared from PG:glycerol mixture (ZSNP-PG:G), the nanoparticles size increased compared to ZSNP-PG:W and a small percent of agglomerates was observed (9%). This phenomenon is related to the high viscosity of PG:glycerol solution. The percentage yield of the nanoparticles was very high for all formulations (about 95-98%).

In the case of nanoparticles obtained after the addition of a protein non-solvent other than water, sizes and polydispersity indexes were higher than those obtained for ZSNP obtained with water. Therefore, nanoparticles formed after the addition of a protein non-solvent other than water were less homogeneous in size and showed bigger percent of agglomerates than ZSNP obtained with water.

TABLE 2

Physico-chemical characteristics of ZSNP prepared from binary mixtures of PG and other solvents.
Data expressed as mean ± SD (n = 6)

| | [a]Size (nm), (±SD) Peak and percentage | | | | [b]PDI | [c]Zeta potential (mV), (±SD) | [d]% yield, (±SD) |
|---|---|---|---|---|---|---|---|
| | Peak 1 (nm) | % | Peak 2 (nm) | % | | | |
| ZSNP-PG:W | 117.11 (0.120) | 100% | | | 0.189 | +32.12 (0.41) | 96.22 (1.16) |
| ZSNP-PG:G | 125.03 (1.22) | 91% | 2320.11 (34.21) | 9% | 0.273 | +30.20 (1.36) | 98.13 (0.56) |
| ZSNP-PG:Lab | 151.16 (3.71) | 100% | | | 0.143 | +31.43 (0.60) | 98.10 (3.25) |
| ZSNP-PG:Lut | 143.05 (1.42) | 100% | | | 0.220 | +32.73 (1.99) | 95.12 (2.10) |
| ZSNP-PG:T80 | 161.21 (4.60) | 100% | | | 0.178 | +34.33 (1.62) | 96.55 (3.87) |
| ZSNP-PG:G/G | 557.21 | Nd | 1393.6 | nd | 0.462 | nd | nd |
| ZSNP-PG:Lut/Lut | 331.82 | 100% | | | 0.339 | nd | nd |
| ZSNP-PG:Lab/Lab | 429.22 | Nd | 343.75 | nd | 0.333 | nd | nd |

ZSNP-PG:W: Self-assembled zein nanoparticles prepared from zein PG solution mixed with water by the addition of required additional amount of water.
ZSNP-PG:G: Self-assembled zein nanoparticles prepared from zein PG solution mixed with glycerol by the addition of required amount of water.
ZSNP-PG:Lab: Self-assembled zein nanoparticles prepared from zein PG solution mixed with Labrasol ® by the addition of required amount of water.
ZSNP-PG:Lut: Self-assembled zein nanoparticles prepared from zein PG solution mixed with Lutrol ® L 44 by the addition of required amount of water.
ZSNP-PG:T80: Self-assembled zein nanoparticles prepared from zein PG solution mixed with Tween ® 80 by the addition of required amount of water.
ZSNP-PG:G/G: Self-assembled zein nanoparticles prepared from zein PG solution mixed with glycerol by the addition of required additional amount of glycerol.
ZSNP-PG:Lut/Lut: Self-assembled zein nanoparticles prepared from zein PG solution mixed with Lutrol ® by the addition of required additional amount of Lutrol ®.
ZSNP-PG:Lab/Lab: Self-assembled zein nanoparticles prepared from zein PG solution mixed with Labrasol ® by the addition of required additional amount of Labrasol ®.
[a]Determination of the nanoparticles size (nm) by photon correlation spectroscopy.
[b]Polydispersity Index.
[c]Determination of the zeta potential by electrophoretic laser Doppler anemometry.
[d]Percentage of the nanoparticles formed from the initial amount of the zein protein used.

Example 3

Encapsulation of Bovine Serum Albumin (BSA) as Large Hydrophilic Molecule Model in Self-Assembled Zein Nanoparticles (ZSNP)

3.1 Encapsulation of BSA in Self-Assembled Zein Nanoparticles

A fluorescently labelled protein was used as a large molecule drug model to be incorporated into self-assembled zein nanoparticles (ZSNP). For that purpose, 200 µL of aqueous solution of fluorescein isothiocyanate labelled bovine serum albumin (FITC-BSA) at a concentration of 1 mg/mL were incorporated in 2 mL of zein PG solution (2.5% zein w/v). To obtain traditional zein nanoparticles, 200 µL of FITC-BSA (1 mg/mL) were incorporated in 70% hydroalcoholic solution having a similar concentration of zein. In order to obtain ZSNP, one mL of zein PG solution containing FITC-BSA was added to 5 mL of bidistilled water. FITC-BSA-loaded nanoparticles prepared by a traditional method were obtained according to the previously described in Example 1 with the same amounts of zein and FITC-BSA. The final aqueous suspension of FITC-BSA-loaded nanoparticles was purified by centrifugation and collected for further characterization as described in Example 1.

3.2 Characterization of FITC-BSA-Loaded Self-Assembled Zein Nanoparticles (ZSNP)

The size, zeta potential and yield of the nanoparticles preparation process were determined as described in Example 1. In order to calculate the encapsulation efficiency of FITC-BSA in ZSNP and nanoparticles obtained by a traditional method using ethanol, the nanoparticles suspensions were centrifuged at 27,000×g for 20 min. Then, the quantity of loaded FITC-BSA was estimated as the difference between its initial concentration added and the concentration measured in the supernatants after the centrifugation step. For that purpose, calibration curves were prepared with FITC-BSA standard solutions at a concentration range from 1 to 20 µg/mL (r=0.996). The assay was performed by spectrofluorimetry at 480 nm (excitation wavelength) and 520 nm (emission wavelength) (GENios, TECAN, Austria).

3.3 Results

3.3.1 Characterization of FITC-BSA-Loaded Self-Assembled Zein Nanoparticles (ZSNP)

Table 3 describes the main physico-chemical characteristics of FITC-BSA-loaded ZSNP (ZSNP-BSA) and zein nanoparticles prepared by solvent displacement method (Z-NP-BSA-T). It was observed that both types of nanoparticles displayed a homogeneous size and positive surface charge. The encapsulation efficiency of FITC-BSA in zein nanoparticles prepared by the self-assembly method (ZSNP-BSA) was 1.5 times higher than that obtained by the traditional method (Z-NP-BSA-T). This may be due to the precipitation of BSA that associated in ethanol phase. The encapsulation efficiency indicated the high capacity of the self-assembly method to incorporate large molecules such as proteins.

TABLE 3

Physico-chemical characteristics of FITC-BSA-loaded zein nanoparticles
Data expressed as mean ± SD (n = 6)

|  | [a] Size (nm), (±SD) | [b] PDI | [c] Zeta potential (mV), (±SD) | [d] % yield, (±SD) | [e] % Encapsulation efficiency of FITC-BSA, (±SD) |
|---|---|---|---|---|---|
| ZSNP-BSA | 116.41 (1.34) | 0.271 | +23.8 (0.77) | 96.39 (3.11) | 92.22 (1.59) |
| Z-NP-BSA-T | 121.83 (0.51) | 0.222 | +28.7 (1.10) | 98.37 (2.11) | 61.11 (2.12) |

ZSNP-BSA: Self assembled zein nanoparticles loaded with FITC-BSA
Z-NP-BSA-T: Zein nanoparticles prepared by a traditional solvent displacement method loaded with FITC-BSA
[a] Determination of the nanoparticles size (nm) by photon correlation spectroscopy.
[b] Polydispersity Index.
[c] Determination of the zeta potential by electrophoretic laser Doppler anemometry.
[d] The percentage of the nanoparticles formed from the initial amount of the zein protein used.
[e] % Encapsulation efficiency: Percentage of the amount of encapsulated FITC-BSA protein in zein nanoparticles in relation with the initial amount used.

Example 4

Encapsulation of Rhodamine B as Small Hydrophilic Molecule Model in Self-Assembled Zein Nanoparticles (ZSNP)

4.1 Encapsulation of Rhodamine B in Self-Assembled Zein Nanoparticles

Rhodamine B isothiocianate (RB), a fluorescently small molecule, was used as a small hydrophilic molecule model to be incorporated into ZSNP for the bioadhesion study. For that purpose, 500 µL of aqueous solution of RB (1 mg/mL), were incorporated in 4 mL of zein PG solution or PG binary mixture with glycerol or Lutrol® L 44 as described in Example 2. The final zein concentration was usually kept at 2.5% w/v. In order to obtain RB-loaded ZSNP nanoparticles, one mL of zein solution containing RB was added to 5 mL of bidistilled water. The final aqueous suspension of RB-loaded zein nanoparticles was collected for further characterization. The formulations were prepared from a primary solvent propylene glycol (RB-ZSNP-PG), or binary mixture of PG and other secondary solvents including Lutrol® L 44 (RB-ZSNP-PG:Lut) or glycerol (RB-ZSNP-PG:G). The volume of the secondary solvents was selected according to the previous study performed to determine the miscibility zone between zein PG and PG miscible non-volatile solvents in which zein was not soluble.

In order to compare the encapsulation efficiency of ZSNP with traditional zein nanoparticles prepared by a solvent displacement method, RB-loaded zein nanoparticles prepared by a traditional method were obtained according to the previously described protocol with slight modifications as described in Example 1 with the same amounts of zein and RB. The final aqueous suspension of RB-loaded zein nanoparticles was collected for further characterization as described in Example 1.

4.2 Characterization of RB-Loaded Self-Assembled Zein Nanoparticles (RB-ZSNP)

The size, zeta potential and yield of the nanoparticles preparation process were determined as described in Example 1. In order to calculate the encapsulation efficiency of RB in ZSNP, the nanoparticles suspensions were centrifuged at 27,000×g for 20 min. Then, the amount of the RB loaded into the nanoparticles was determined by colorimetry at 540 nm (Labsystems iEMS Reader MF, Finland). The quantity of loaded RB was estimated as the difference between its initial concentration added and the concentration measured in the supernatants after the centrifugation step. For that purpose, calibration curves were prepared with RBITC (Rhodamine β isothiocyanate) standard solutions at a concentration range from 10 to 100 µg/mL (r=0.996).

4.3 Release of RB from ZSNP in Simulated Gastrointestinal Tract Fluids

In vitro release of RB from the nanoparticles was studied according to a modified protocol described elsewhere [39]. For that purpose, 5 mL of RB-loaded ZSNP, prepared from primary solvent propylene glycol (RB-ZSNP-PG), or binary mixture of PG and other secondary solvents including Lutrol® L 44 (RB-ZSNP-PG:Lut) or glycerol (RB-ZSNP-PG:G), and RB-traditional nanoparticles (RB-Traditional NP) were centrifuged at 27,000×g for 20 min to eliminate the non-encapsulated RB. Then, the precipitated RB-loaded nanoparticles were dispersed in 20 mL of simulated gastric fluid (SGF; USP XXIII, pH 1.2; pepsin 0.32% w/v) at 37±1° C. Then, 1 mL of the suspension was incubated for 2 hours. After that, the nanoparticles were centrifuged at 27,000×g for 20 min and the supernatants were collected to calculate the amount of RB released from the nanoparticles under acidic conditions. Then, the pellets were resuspended in 1 mL of simulated intestinal fluid (SIF; USP XXIII, pH 7.5; pancreatin 1% w/v) at 37±1° C. At different times (1, 2, 3, 4, 5, 6, 7 and 8 h) the nanoparticles were centrifuged at 27,000×g for 20 min and the supernatants were collected to calculate the amount of RB released from the nanoparticles after the incubation under SIF conditions as described above and the resulting pellets always dispersed in the SIF after each corresponding time. In all cases, the amount of released RB from both fluids was assayed by spectrofluorimetry at 540 nm (excitation wavelength) and 580 nm (emission wavelength) (GENios, TECAN, Austria).

4.4 Results

4.4.1 Characterization of RB-Loaded Self-Assembled Zein Nanoparticles (RB-ZSNP)

Table 4 describes the main physico-chemical characteristics of RB-loaded self-assembled nanoparticles (RBZ-SNP). The formulations were prepared from a primary solvent propylene glycol (RB-ZSNP-PG), or binary mixture of PG and other secondary solvents including Lutrol® L 44 (RB-ZSNP-PG:Lut) or glycerol (RB-ZSNP-PG:G). Traditional zein nanoparticles were prepared by a solvent displacement method (RB-Traditional NP). The encapsulation efficiency indicated the slight higher capacity of nanoparticles prepared by the self-assembly method to incorporate small hydrophilic molecules compared to nanoparticles prepared by a traditional method. In both cases, the size of the nanoparticles was homogeneous. In both cases, the association of RB did not affect the surface charge of the nanoparticles.

TABLE 4

Physico-chemical characteristics of Rhodamine B-loaded zein nanoparticles. Data expressed as mean ± SD (n = 6).

| | [a] Size (nm), (±SD) | [b] PDI | [c] Zeta potential (mV), (±SD) | [d] % yield, (±SD) | [e] % Encapsulation efficiency of Rhodamine B (±SD) |
|---|---|---|---|---|---|
| RB-ZSNP-PG | 123.44 (1.73) | 0.122 | +36.03 (3.66) | 95.32 (1.73) | 81.44 (1.18) |
| RB-ZSNP-PG: Lut | 164.10 (0.31) | 0.187 | +32.46 (3.23) | 95.26 (1.74) | 83.16 (2.77) |
| RB-ZSNP-PG: G | 155.64 (3.81) | 0.146 | +31.03 (2.00) | 95.59 (1.01) | 84.35 (3.54) |
| RB-Traditional NP | 133.50 (1.81) | 0.129 | +35.51 (1.63) | 96.52 (2.54) | 75.31 (1.33) |

RB-ZSNP-PG Self-assembled zein nanoparticles loaded with RB obtained from a primary solvent propylene glycol
RB-ZSNP-PG: Lutrol RB-ZSNP-PG: G: Self-assembled zein nanoparticles loaded with RB obtained from binary mixture of PG with Lutrol ® L 44 or glycerol, respectively
RB-Traditional NP: Zein nanoparticles prepared by a solvent displacement method loaded with RB
[a] Determination of the nanoparticles size (nm) by photon correlation spectroscopy.
[b] Polydispersity Index.
[c] Determination of the zeta potential by electrophoretic laser Doppler anemometry.
[d] The percentage of the nanoparticles formed from the initial amount of the zein protein used.
[e] % Encapsulation efficiency: Percentage of the amount of encapsulated Rhodamine B in zein nanoparticles in relation with the initial amount used.

4.4.2 Release of RB from ZSNP in Simulated Gastrointestinal Tract Fluids

Figure 3:
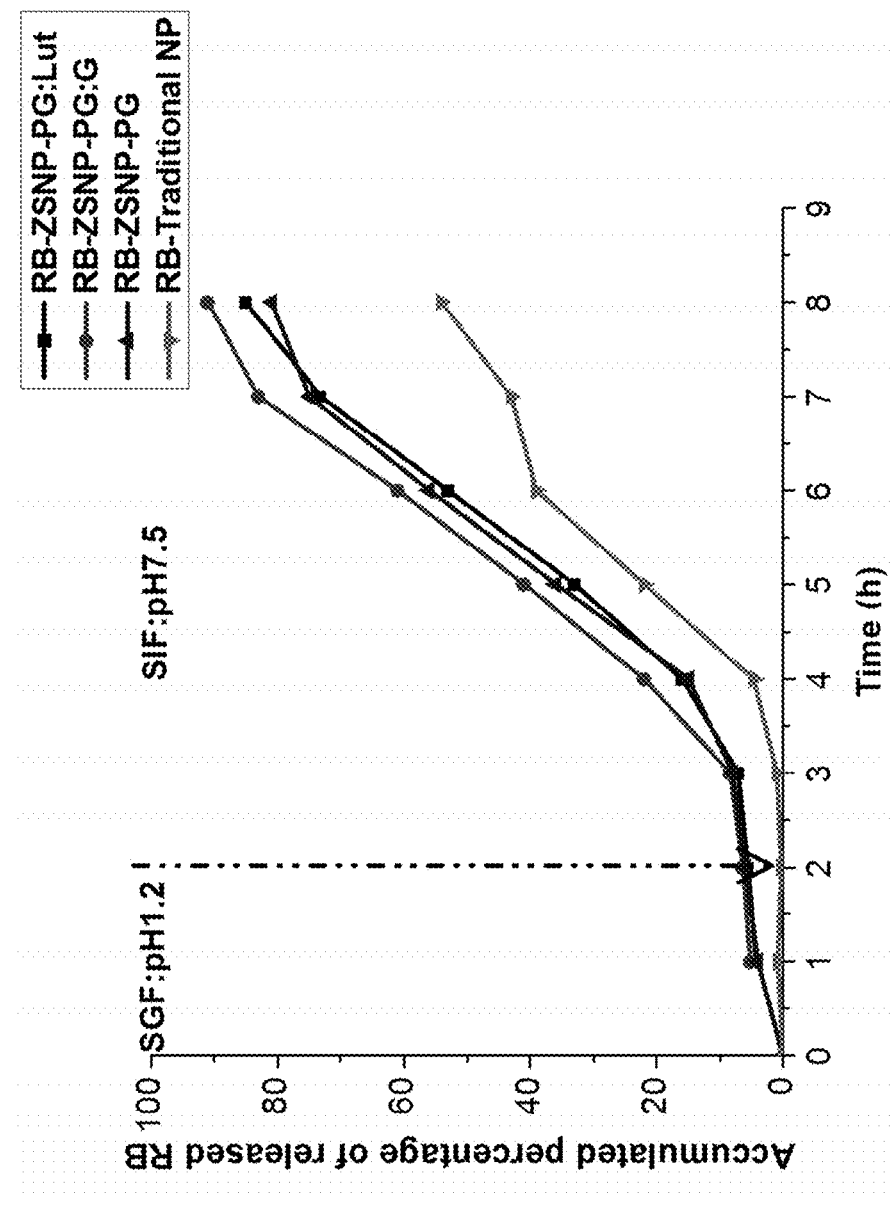

FIG. 3 shows that all of the types of nanoparticles formulations have a high stability in acidic simulated gastric fluid (SGF). In this case, the total amount of released RB from all of the types of nanoparticles formulations was less than 5%. On the other hand, after the incubation in SIF, the release profile of RB-self-assembled zein nanoparticles (RB-ZSNP) was different from the profile described for zein nanoparticles obtained by a traditional method (RB-Traditional NP). It has been observed that the association of PG in the nanoparticles matrix enhanced the release of RB in RB-ZSNP compared to traditional ones. In fact, the total amount of released RB in SIF at the end of the study was between 1.4 and 1.5 times higher for RB-ZSNP than for RB-Traditional NP.

Example 5

Encapsulation of a Fluorescent Probe as Small Lipophilic Molecule Model in ZSNP

5.1 Production of ZSNP Loaded with a Lipophilic Small Molecule

In order to investigate the capacity of ZSNP to entrap hydrophobic molecules, the lipophilic fluorescent probe 1,1'-dioctadecyl-3,3,3',3'-tetramethylindocarbocyanine perchlorate (TP) was selected as water insoluble hydrophobic molecule. For that purpose, 1 mg of 1,1'-dioctadecyl-3,3,3',3'-tetramethylindocarbocyanine perchlorate was dissolved in different volumes of PG zein solution (1% w/v) under magnetic agitation overnight. The ratio zein:1,1'-dioctadecyl-3,3,3',3'-tetramethylindocarbocyanine perchlorate was 2.5:1, 5:1 and 10:1 w/w. Then, one mL of zein PG solution containing 1,1'-dioctadecyl-3,3,3',3'-tetramethylindocarbocyanine perchlorate was added to 5 mL of bidistilled water. The final aqueous suspension of 1,1'-dioctadecyl-3,3,3',3'-tetramethylindocarbocyanine perchlorate-loaded zein nanoparticles was collected for further characterization.

5.2 Characterization of 1,1'-dioctadecyl-3,3,3',3'-tetramethylindocarbocyanine Perchlorate-Loaded Self-Assembled Zein Nanoparticles (ZSNP)

The size, zeta potential and yield of the nanoparticles preparation process were determined as described in Example 1. In order to calculate the encapsulation efficiency of 1,1'-dioctadecyl-3,3,3',3'-tetramethylindocarbocyanine perchlorate in ZSNP, the nanoparticles suspensions were firstly centrifuged at 3,000×g to investigate the presence of crystals of non entrapped 1,1'-dioctadecyl-3,3,3',3'-tetramethylindocarbocyanine perchlorate. Then, the supernatants were centrifuged again at 27,000×g for 20 min. The crystals of 1,1'-dioctadecyl-3,3,3',3'-tetramethylindocarbocyanine perchlorate that precipitated after the first centrifugation were resuspended in absolute ethanol. The amount of 1,1'-dioctadecyl-3,3,3',3'-tetramethylindocarbocyanine perchlorate was assayed by spectrofluorimetry at 540 nm (excitation wavelength) and 580 nm (emission wavelength) (GENios, TECAN, Groedig, Austria). On the other hand, the amount of free 1,1'-dioctadecyl-3,3,3',3'-tetramethylindocarbocyanine perchlorate in the supernatant after the second centrifugation step was assayed by spectrofluorimetry at 540 nm (excitation wavelength) and 580 nm (emission wavelength) (GENios, TECAN, Groedig, Austria). The calibration curves were prepared with absolute ethanol containing 1,1'-dioctadecyl-3,3,3',3'-tetramethylindocarbocyanine perchlorate standard solutions at a concentration range from 1 to 10 µg/mL (r=0.996). The quantity of loaded 1,1'-dioctadecyl-3,3,3',3'-tetramethylindocarbocyanine perchlorate was estimated as the difference between its initial concentration added and the free amount measured in the precipitate after the first centrifugation step and the supernatant after the second centrifugation step.

5.3 Results

5.3.1 Characterization of 1,1'-dioctadecyl-3,3,3',3'-tetramethylindocarbocyanine Perchlorate-Loaded Self-Assembled Zein Nanoparticles (ZSNP)

From the results shown in Table 5, it can be concluded that the encapsulation efficiency of 1,1'-dioctadecyl-3,3,3',3'-tetramethylindocarbocyanine perchlorate was high (more than 80%) for all formulations. However, the encapsulation efficiency significantly decreased by increasing the percentage of the initial amount of 1,1'-dioctadecyl-3,3,3',3'-tetramethylindocarbocyanine perchlorate in relation to zein. In this context, the encapsulation efficiency was found to be 80% for ZSNP prepared from a zein: 1,1'-dioctadecyl-3,3,3',3'-tetramethylindocarbocyanine perchlorate weight ratio of 2.5:1 (ZSNP-TP-2.5:1) and approximately 90% for ZSNP prepared from a zein:1,1'-dioctadecyl-3,3,3',3'-tetramethylindocarbocyanine perchlorate w/w ratio of 5:1 (ZSNP-TP-5:1). However, with increasing initial amount of 1,1'-dioctadecyl-3,3,3',3'-tetramethylindocarbocyanine perchlorate in the formulation (that is, decreasing the ratio Zein:1,1'-dioctadecyl-3,3,3',3'-tetramethylindocarbocyanine perchlorate), the amount of the encapsulated fluorescent probe per mg of nanoparticle increases in the same proportion. In a similar way, the particle size was significantly increased by increasing the amount of loaded 1,1'-dioctadecyl-3,3,3',3'-tetramethylindocarbocyanine perchlorate in relation to zein. In all formulations, the yield of the zein protein was high to achieve 98% of the initial zein used to obtain the nanoparticles. On the other hand, increasing the percentage of 1,1'-dioctadecyl-3,3,3',3'-tetramethylindocarbocyanine perchlorate in relation to zein protein caused a significant decrease in the zeta potential.

TABLE 5

Physico-chemical characteristics of ZSNP loaded with 1,1'-dioctadecyl-3,3,3',3'-tetramethylindocarbocyanine perchlorate.
Data expressed as mean ± SD (n = 6)

|  | [a]Size (nm), (±SD) | [b]PDI | [c]Zeta potential (mV), (±SD) | [d]% yield, (±SD) | [e]% Encapsulation efficiency (±SD) | [f]Loaded TP (µg/mg np) (±SD) |
|---|---|---|---|---|---|---|
| ZSNP-TP-2.5:1 | 206.23 (2.07) | 0.109 | −12.03 (3.66) | 98.19 (1.81) | 81.13 (1.67) | 330.50 (6.80) |
| ZSNP-TP-5:1 | 178.98 (4.00) | 0.211 | +6.51 (1.63) | 99.32 (2.13) | 90.14 (2.61) | 183.60 (5.31) |
| ZSNP-TP-10:1 | 133.12 (3.11) | 0.223 | +13.51 (1.63) | 99.32 (2.13) | 97.66 (2.99) | 99.46 (3.04) |

ZSNP-TP-2.5:1, ZSNP-TP-5:1 and ZSNP-TP-10:1: Self-assembled zein nanoparticles loaded with 1,1'-dioctadecyl-3,3,3',3'-tetramethylindocarbocyanine perchlorate (zein:1,1'-dioctadecyl-3,3,3',3'-tetramethylindocarbocyanine perchlorate was 2.5:1, 5:1 and 10:1 w/w, respectively)
[a]Determination of the nanoparticles size (nm) by photon correlation spectroscopy.
[b]Polydispersity Index.
[c]Determination of the zeta potential by electrophoretic laser Doppler anemometry.
[d]The percentage of the nanoparticles formed from the initial amount of the zein protein used.
[e]% Encapsulation efficiency: Percentage of the amount of encapsulated 1,1'-dioctadecyl-3,3,3',3'-tetramethylindocarbocyanine perchlorate in ZSNP in relation with the initial amount used.
[f]Amount of loaded 1,1'-dioctadecyl-3,3,3',3'-tetramethylindocarbocyanine perchlorate (µg) per mg of nanoparticle (np).

Example 6

Encapsulation of Lipophilic Antioxidant Curcumin in ZSNP

6.1 Production of Self-Assembled Zein Nanoparticles (ZSNP) Loaded with Curcumin In order to investigate the capacity of ZSNP to entrap food antioxidant hydrophobic molecules, curcumin was selected as a water insoluble hydrophobic molecule. Curcumin (diferuloylmethane) is a natural polyphenol obtained from the rhizome of turmeric (*Curcuma longa*). For that purpose, 10 mg of curcumin were dissolved in 10 mL of zein solution in PG with different concentrations of zein (2.5 and 5% w/v) or similar concentrations of zein in 10 mL of PG containing 10% of Labrasol® v/v. Then, one mL of zein PG solution containing curcumin was added to 4 mL of bidistilled water. The final aqueous suspension of curcumin-loaded zein nanoparticles (ZSNP-C-2.5 and ZSNP-C-5) or formulations done with Labrasol® (ZSNP-C-2.5L and ZSNP-C-5L) were purified by centrifugation and collected for further characterization.

6.2 Characterization of Curcumin-Loaded Self-Assembled Zein Nanoparticles (ZSNP-C)

The size, zeta potential and yield of the nanoparticles preparation process were determined as described in Example 1. In order to calculate the encapsulation efficiency of curcumin, 1.5 mL of freshly prepared curcumin-loaded ZSNP were centrifuged at 27,000×g during 20 min and the supernatants were collected, diluted with ethanol, and assayed to calculate the free amount of curcumin by UV spectrophotometry at 425 nm [40] (Shimadzu 1203 UV-VIS). The quantity of curcumin loaded in the nanoparticles was estimated as the difference between its initial concentration added and the concentration measured in the supernatants after the centrifugation step.

6.3 Results

6.3.1 Characterization of Self-Assembled Zein Nanoparticles (ZSNP) Loaded with Curcumin Table 6 describes the main physico-chemical characteristics of curcumin-loaded ZSNP. It has been observed that the presence of Labrasol® significantly decreased the nanoparticles size if compared the size of both ZSNP-C-2.5 and ZSNP-C-5 with the same formulations containing Labrasol® (ZSNP-C-2.5L and ZSNP-C-5L). However, the presence of curcumin did not significantly affect the positive surface charge of the formulations. In all cases, high nanoparticles yield was obtained which was about 95% of the initial amount of zein that was transformed into nanoparticulate structure. Generally, the encapsulation efficiency indicated the high capacity of the self-assembly method to incorporate small hydrophobic molecules (curcumin) which was ranged from 65 to 75%. In this case, it has been observed that the presence of Labrasol® slightly decreased the encapsulation efficiency compared to nanoparticles formulations obtained from zein-PG solution.

TABLE 6

Physico-chemical characteristics of ZSNP loaded with curcumin
Data expressed as mean ± SD (n = 6)

|  | $^a$ Size (nm), (±SD) | $^b$ PDI | $^c$ Zeta potential (mV), (±SD) | $^d$ % yield, (±SD) | $^e$ % Encapsulation efficiency of curcumin (±SD) |
|---|---|---|---|---|---|
| ZSNP-C-2.5 | 366.13 (2.07) | 0.209 | +36.11 (3.66) | 95.22 (1.00) | 70.13 (1.39) |
| ZSNP-C-5 | 358.33 (4.00) | 0.181 | +35.54 (2.63) | 94.11 (2.66) | 75.15 (2.67) |
| ZSNP-C-2.5L | 218.98 (2.00) | 0.241 | +36.51 (0.63) | 96.75 (2.22) | 65.23 (5.61) |
| ZSNP-C-5L | 213.12 (3.98) | 0.273 | +33.41 (2.65) | 95.62 (2.33) | 63.66 (2.12) |

ZSNP-C-2.5 and ZSNP-C-5: Self-assembled zein nanoparticles loaded with curcumin using PG-zein solution at initial zein concentrations of 2.5 and 5% w/v in PG, respectively.
ZSNP-C-2.5L and ZSNP-C-5L: Self-assembled zein nanoparticles loaded with curcumin using PG-zein solution containing Labrasol® (10% v/v) at initial zein concentrations of 2.5 and 5% w/v in PG: Labrasol® solution, respectively.
$^a$ Determination of the nanoparticles size (nm) by photon correlation spectroscopy.
$^b$ Polydispersity Index.
$^c$ Determination of the zeta potential by electrophoretic laser Doppler anemometry.
$^d$ The percentage of the nanoparticles formed from the initial amount of the zein protein used.
$^e$ % Encapsulation efficiency: Percentage of the amount of encapsulated curcumin in the nanoparticles formulations in relation with the initial amount of curcumin used.

Example 7

Encapsulation of Chlorhexidine in ZSNP as Antimicrobial Agent for Buccal Delivery

7.1 Production of Chlorhexidine-Loaded ZSNP

In order to investigate the capacity of ZSNP to entrap antimicrobial agents, such as chlorhexidine (CHX), 0.6 mL of CHX-gluconate solution (20% w/v Eur.Ph.) were mixed with 5 mL of PG solution containing zein (2.5% w/v) under magnetic stirring. Then, CHX-PG solution was poured into 94.4 mL or 44.4 mL of bidistilled water to achieve the formation of CHX-loaded ZSNP with a final CHX concentration of 0.12% and 0.24% w/v, respectively.

7.2 Characterization of Chlorhexidine-Loaded ZSNP

The size, zeta potential and yield of the nanoparticles preparation process were determined as described in Example 1. In order to calculate the encapsulation efficiency of CHX, one mL of freshly prepared CHX-loaded ZSNP was centrifuged at 27,000×g during 20 min and the supernatants were collected and assayed to calculate the free amount of CHX by UV spectrophotometry at 260 nm (Shimadzu 1203 UV-VIS) [41]. The quantity of loaded CHX in the nanoparticles was estimated as the difference between its initial concentration added and the concentration measured in the supernatants after the centrifugation step.

7.3 Results

7.3.1 Characterization of Self-Assembled Zein Nanoparticles (ZSNP) Loaded with CHX Table 7 describes the main physico-chemical characteristics of CHX-loaded ZSNP. In both types of CHX-loaded nanoparticles (CHX-ZSNP-0.12 and CHX-ZSNP-0.24), the size of the nanoparticles was homogeneous (around 135 nm). In addition, the nanoparticles displayed a positive charge. The encapsulation efficiency of CHX was very high, achieving about 90% of the initial amount of CHX used.

TABLE 7

Physico-chemical characteristics of ZSNP loaded with CHX
Data expressed as mean ± SD (n = 6)

|   | $^a$ Size (nm), (±SD) | $^b$ PDI | $^c$ Zeta potential (mV), (±SD) | $^d$ % yield, (±SD) | $^e$ % Encapsulation efficiency of CHX (±SD) |
|---|---|---|---|---|---|
| CHX-ZSNP-0.12 | 134.56 (3.04) | 0.121 | +30.50 (4.79) | 96.55 (2.90) | 90.18 (2.82) |
| CHX-ZSNP-0.24 | 132.11 (1.83) | 0.100 | +24.54 (1.23) | 97.21 (2.71) | 92.24 (1.37) |

CHX-ZSNP-0.12 and CHX-ZSNP-0.24: Self-assembled zein nanoparticles loaded with CHX to achieve a final CHX concentration of 0.12 and 0.24% w/v in the aqueous suspension of ZSNP
$^a$ Determination of the nanoparticles size (nm) by photon correlation spectroscopy.
$^b$ Polydispersity Index.
$^c$ Determination of the zeta potential by electrophoretic laser Doppler anemometry.
$^d$ The percentage of the nanoparticles formed from the initial amount of the zein protein used.
$^e$ % Encapsulation efficiency: Percentage of the amount of encapsulated CHX in the nanoparticles formulations in relation with the initial amount of CHX used.

Example 8

Ex Vivo Mucosal Affinity Study of Zein Nanoparticles in Porcine Buccal Mucosa

8.1 Release of Rhodamine B (RB) from Nanoparticles Formulations in Simulated Saliva Fluid In order to insure that the fluorescence intensity measured in the buccal mucosal tissue is not originated from free RB that released from nanoparticles matrix, an in vitro release study of RB from nanoparticles in simulated saliva fluid was performed. For this purpose, 500 µL of nanoparticles formulations prepared from a primary solvent propylene glycol (RB-ZSNP-PG), or binary mixture of PG and other secondary solvents including Lutrol® L 44 (RB-ZSNP-PG:Lut) or glycerol (RB-ZSNP-PG:G) and zein nanoparticles prepared by a traditional method (RB-Traditional NP) (Example 4) were diluted with 75 mL of simulated saliva fluid (SSF) [42]. At different time intervals (0.5, 1, 1.5, 2, 2.5, and 3 hours), 1 mL of each sample was centrifuged at 3,000×g using dialysis tubes Vivaspin® 5,000 MWCO (VIVASPIN, Germany). The amount of free RB in the dialysate was assayed by spectrofluorimetry at 540 nm (excitation wavelength) and 580 nm (emission wavelength) (GENios, TECAN, Austria).

8.2 Quantitative Bioadhesion Assay in Buccal Mucosa

The ex vivo bioadhesion study was performed with nanoparticles formulations fluorescently labeled with RB obtained in Example 4.

For this purpose, porcine heads were obtained from a local slaughterhouse and the buccal mucosa was surgically isolated. The epithelium was cleaned from underlying connective tissues using surgical scissors and cut in 2 cm² circular areas. Then, tissue samples were stored in PBS at 4° C. and used within 1 hour. Tissue samples were clamped between tow flat flange of Franz cell compartments and the nanoparticles formulations were deposited in the donor compartment. In this case, the nanoparticles formulations were 500 µL of: (i) three aqueous suspensions of Rhodamine B-fluorescently labelled zein nanoparticles obtained by self-assembly technology at a concentration of 4.2 mg/mL of zein nanoparticles w/v) prepared from different solvents (RB-ZSNP-PG, RB-ZSNP-PG:Lut and RB-ZSNP-PG:G) and (ii) Rhodamine B-fluorescently labelled zein nanoparticles prepared by a traditional solvent evaporation technique at the same concentration.

For sample application to the mucosal surfaces, one side of the donor compartment (1 cm² of the tissue) was exposed to 500 µL of aqueous nanoparticles suspension only for 30 seconds with turbulence agitation to simulate buccal mouth wash conditions. Then, samples were retired from the compartment and formulations were exposed to 75 mL simulated salivary fluids [19] [20] at 37° C. for 6 hours. Tissue samples were removed at different time intervals (0.5, 30, 60, 120 and 180 minutes) and 1 cm² area, which was exposed to the sample during the experiment, were cut and isolated. The amount of adhered nanoparticles was assayed as described previously [38]. Briefly, each mucosal segment was digested with 2 mL of NaOH 3M for 24 h. The samples were diluted to 3 mL by adding NaOH 3M, vortexed for 10 min and centrifuged at 2,000×g for 30 min. Finally, the amount of Rhodamine B was assayed by spectrofluorimetry at 540 nm (excitation wavelength) and 580 nm (emission wavelength) (GENios, TECAN, Groedig, Austri) in order to estimate the fraction of adhered nanoparticles to the mucosa. The standard curves of the bioadhesion study were prepared by addition of Rhodamine B solutions in NaOH 3M (0.05-1 µg/mL) with control tissue (r>0.996).

8.3 Results

Figure 4:
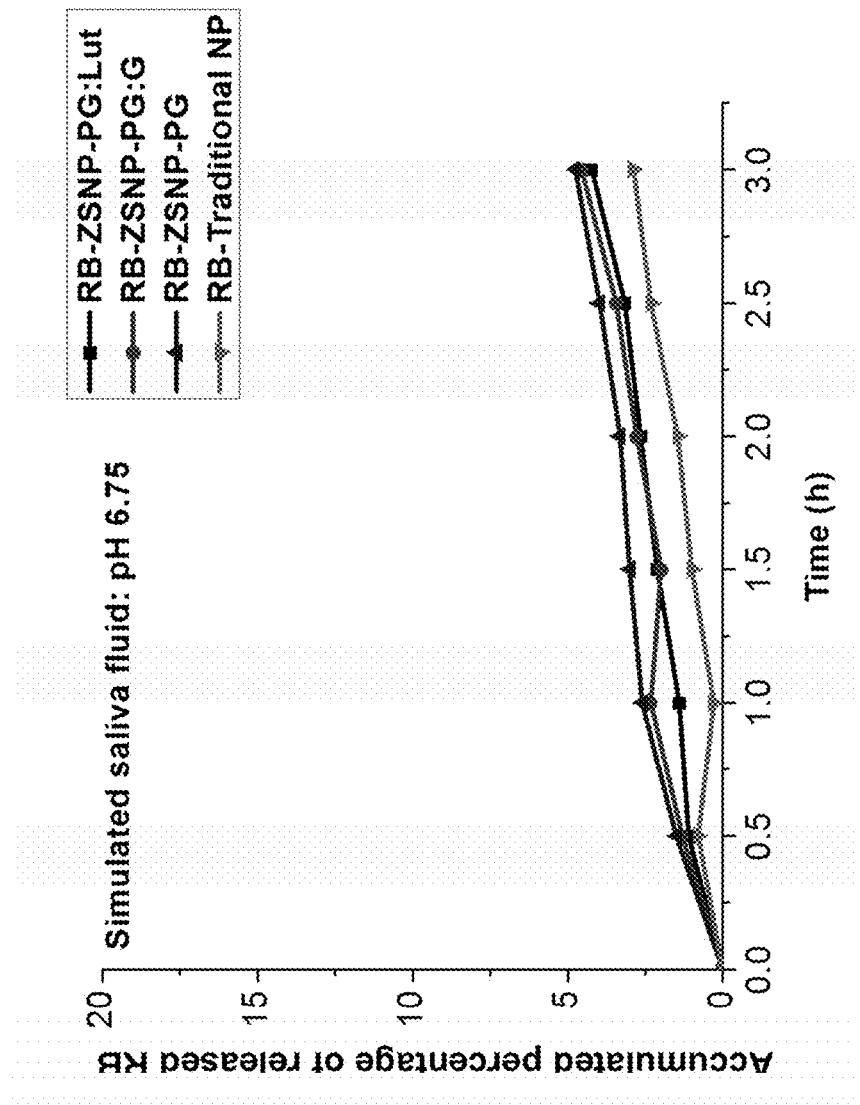

8.3.1 Release of RB from Nanoparticles Formulations in Simulated Saliva Fluid From FIG. 4 it can be observed that the accumulative total amount of RB released from the nanoparticles formulations after 3 hours of incubation in SSF was less than 5% of the total encapsulated amount of RB in the nanoparticles formulations. Thus, it can be assumed that the fluorescence intensity obtained in the following quantitative bioadhesion assay in buccal mucosa is originated from the nanoparticles adhered to the surface of the mucosa, and therefore it is possible to determine the total amount of nanoparticles adhered to the mucosa.

8.3.2 Quantitative Bioadhesion Assay in Buccal Mucosa

Figure 5:
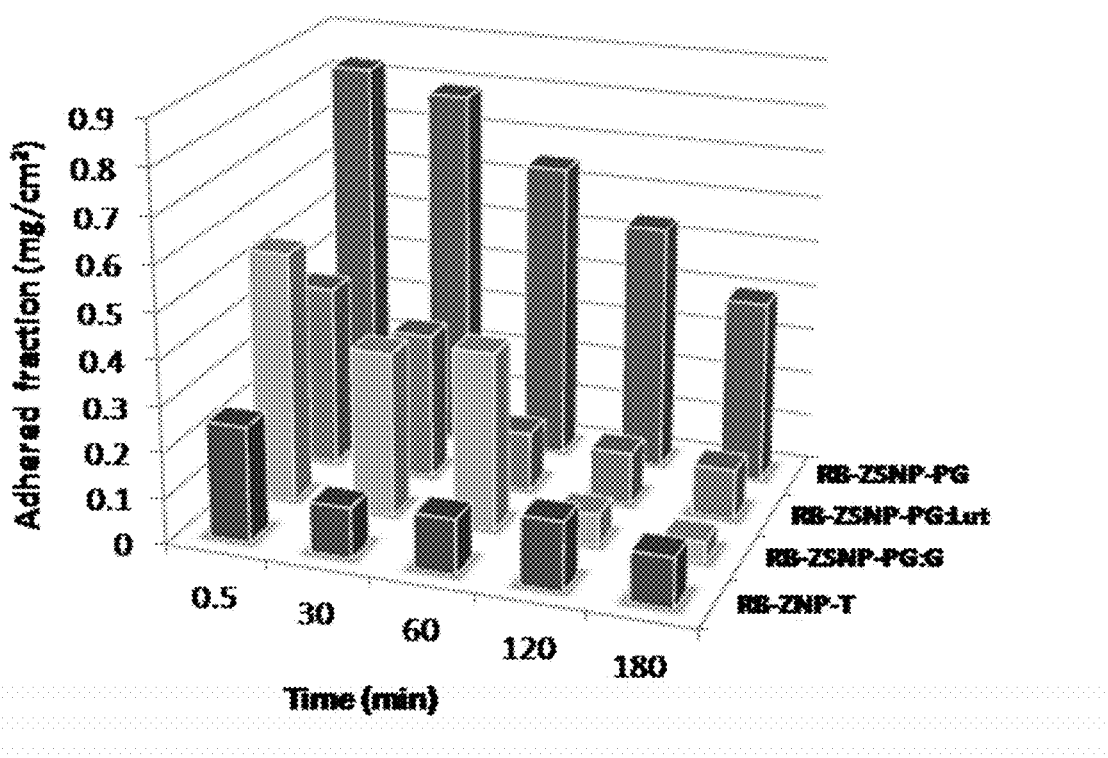

From FIG. 5, it can be observed that the bioadhesive capacity of zein nanoparticles loaded with RB obtained by the self-assembly method and propylene glycol as a primary solvent (RB-ZSNP-PG, was much higher than the bioadhesive capacity of the nanoparticles obtained by a traditional method (RB-ZNP-T). In this context, the initial bioadhesive capacity of RB-ZSNP-PG was approximately 4 times higher than RB-ZNP-T after 0.5 min of contact between the nanoparticles formulation and the buccal mucosa. This phenomenon was observed during 180 min. In addition, the total adhered amount of RB-ZSNP-PG was maintained at higher levels on the surface of the mucosa compared to RB-ZNP-T. In fact, the adhered fraction of RB-ZSNP found at the end of the study (180 min) was 2 times higher than de initial adhered fraction of RB-ZNP-T. In this context, the elimination rate of RB-ZNP-T was faster than RB-ZSNP. In addition, zein nanoparticles loaded with RB obtained by the self-assembly method using binary mixtures of propylene glycol and glycerol (RB-ZSNP-PG:G) and propylene glycol and Lutrol® L 44 (RB-ZSNP-PG:Lut) showed, during the first 60 minutes of the study, bioadhesive capacity higher than the bioadhesive capacity of the nanoparticles obtained by a traditional method (RB-ZNP-T).

Example 9

Cationic and Anionic Self-Assembled Zein Core-Shell Nanocapsules (ZSNC) Containing PG Miscible Essential Oils

9.1 Preparation of Cationic and Anionic ZSNC Containing PG Miscible Essential Oils (Aromas)

An essential oil is a concentrated hydrophobic liquid containing volatile aroma compounds from plants. Essential oils are also known as volatile oils, ethereal oils or aetherolea, or simply as the "oil of" the plant from which they were extracted.

In this case, it has been selected some essential oils that are miscible with zein PG solution, for example, *Mentha Piperita* (Peppermint) oil, Eugenol, Cinnamon oil and Thyme (*Thymus vulgaris*) oil.

In order to obtain ZSNC loaded with these oils by in situ nanoprecipitation-surface deposition technique, 1 mL of each oil was dissolved in 20 mL of zein-PG solution (2.5% w/v) under magnetic stirring at room temperature. Then, the cationic ZSNC were obtained in situ by the simple addition of one milliliter of the oil/zein/PG solution to 4 mL of bidistilled water.

On the other hand, anionic ZSNC loaded with *Mentha Piperita* (Peppermint) oil were prepared by the addition of anionic polymers, such as arabic gum to the freshly prepared aqueous suspension of the nanocapsules. In this case, anionic ZSNC were obtained by the addition of 1 mL of arabic gum aqueous solution (0.25% w/v) to 5 mL of aqueous suspension of cationic ZSNC loaded with *Mentha Piperita* (Peppermint) oil (ZSNC-PA1).

In a similar way, a direct complexation process was applied to obtain anionic ZSNC loaded with *Mentha Piperita* (Peppermint) oil. For this purpose, 1 mL of the *Mentha Piperita* (Peppermint) oil/zein/PG solution was added to 4 mL of an aqueous solution of arabic gum (0.05% w/v) to give ZSNC-PA2. Control samples were done with all types of oils as described above by the same method but without using zein protein.

9.2 Characterization of Cationic and Anionic ZSNC Containing PG Miscible Essential Oils (Aromas)

The size, zeta potential and yield of the nanoparticles preparation process were determined as described in Example 1. The physical aspect of ZSNC and control formulations was observed.

In order to calculate the encapsulation efficiency of different types of essential oils entrapped in ZSNC, the nanocapsules were done by using different essential oils fluorescently labelled with lipophilic fluorescent probe 1,1'-dioctadecyl-3,3,3',3'-tetramethylindocarbocyanine perchlorate at a concentration of 25 µg/mL oil. Then, the nanocapsules were obtained as described above. After that, the free oils that were not loaded in ZSNC, were extracted by a water immiscible oil, such as medium chain triglycerides (Labrafac™ CC). The extraction process was performed by triple extraction under vigorous shaking of 1 mL of Labrafac™ CC with 1 mL of freshly prepared fluorescent ZSNC. Finally, the free oils that were extracted by Labrafac™ CC were assayed by spectrofluorimetry at 540 nm (excitation wavelength) and 580 nm (emission wavelength) (GENios, TECAN, Austria). Control samples (PG only without zein) were done with all types of oils as described above and assayed by the same method.

9.3 Results

9.3.1 Characterization of ZSNC Containing PG Miscible Essential Oils

FIG. 6 shows the encapsulation efficiency of cationic ZSNC loaded with different essential oils. It has been observed the effective encapsulation of the 4 types of essential oils loaded in zein nanocapsules obtained by in situ self-assembly technique. For all types of oils, the encapsulation efficiencies were ranged from 85 to 95%. These values of encapsulation efficiency are significantly higher than values found in bibliography for essential oils encapsulated in nanoparticles obtained by a traditional method [20]. The control samples, done in absence of zein, showed a very low encapsulation efficiency which indicated the formation of unstable emulsions that showed a phase separation and were easily extracted by Labrafac™ CC (Table 8).

Table 8 describes the main physico-chemical characteristics of cationic ZSNC loaded with different essential oils. It was observed that all ZSNC containing essential oils displayed a homogenous size (ranged from 150-180 nm) and positive surface charge. The final aspect of the nanocapsules suspension is milky and homogeneous within the first 60 min post preparation. On the other hand, control samples done with PG only and without zein, displayed a very big droplet size and showed oil separation in all cases. The big droplet size constituted about 80-90% of the control samples which was of 6 to 7 µm within the first 5 min post preparation.

TABLE 8

Physico-chemical characteristics of cationic ZSNC and control formulations loaded with essential oils.
Data expressed as mean ± SD (n = 6)

|  | [a]Size (nm), (±SD) Peak and percentage | | | | [b]PDI | [c]Zeta potential (mV), (±SD) | [d]Aspect within 60 min post formulation preparation |
|---|---|---|---|---|---|---|---|
|  | Peak 1 (nm) | % | Peak 2 (nm) | % |  |  |  |
| ZSNC-P | 145.11 (0.61) | 100% |  |  | 0.223 | +19.22 ± 0.11 | Milky and homogeneous |
| ZSNC-E | 179.03 (4.12) | 100% |  |  | 0.276 | +2.38 ± 0.06 | Milky and homogeneous |
| ZSNC-C | 188.16 (1.80) | 100% |  |  | 0.239 | +21.56 ± 0.20 | Milky and homogeneous |
| ZSNC-T | 163.69 (2.02) | 100% |  |  | 0.230 | +24.14 ± 1.09 | Milky and homogeneous |
| Control P | 411.81 (2.12) | 11% | 6614.65 (11.21) | 89% | 0.578 | −18.8 ± 3.12 | Near clear aspect Oil separation as floating layer |
| Control E | 533.97 (32.37) | 13% | 6723.13 (22.77) | 87% | 0.567 | −30.2 ± 0.38 | Near clear aspect Oil separation as bottom layer |
| Control C | 220.43 (31.12) | 8% | 3453.33 (23.01) | 92% | 0.591 | −15.1 ± 2.41 | Near clear aspect Oil separation as bottom layer |
| Control T | 240.44 (71.62) | 5.5% | 7923.12 (66.33) | 94.5% | 0.578 | −14.2 ± 2.19 | Near clear aspect Oil separation as floating layer |

ZSNC-P, ZSNC-E, ZSNC-C and ZSNC-T: Self-assembled zein nanocapsules prepared from different essential oils including *Mentha Piperita* (Peppermint) oil, Eugenol, Cinnamon oil and Thyme (*Thymus vulgaris*) oil, respectively.
Contol P, E, C and T: Formulations done with the same oils from PG solution without zein protein.
[a]Determination of the nanoparticles size (nm) by photon correlation spectroscopy.
[b]Polydispersity Index.
[c]Determination of the zeta potential by electrophoretic laser Doppler anemometry.
[d]Description of the ZSNC and control formulations such as, phase separation, sedimentation, agglomerations or floating.

Table 9 shows the physico-chemical characteristics of anionic nanocapsules loaded with *Mentha Piperita* (Peppermint) oil (ZSNC-PA1 and ZSNC-PA2). The surface charge for both types of nanocapsules was negative. In this case, it has been observed that the coating of ZSNC-P with arabic gum (ZSNC-PA1) or the inclusion of the same gum in the shell of ZSNC (ZSNC-PA2) significantly increased the nanocapsules size compared to cationic ZSNC-P (Table 8). In addition, big particles were formed due to the agglomeration caused by opposite charge interactions between zein and arabic gum. Furthermore, it has been shown that anionic nanocapsules loaded with *Mentha Piperita* (Peppermint) oil (ZSNC-PA1 and ZSNC-PA2) displayed a high encapsulation efficiency which was 84 and 75%, respectively.

TABLE 9

Physico-chemical characteristics of anionic ZSNC loaded with *Mentha Piperita* oil.
Data expressed as mean ± SD (n = 6)

|  | [a]Size (nm), (±SD) Peak and percentage | | | | [b]PDI | [c]Zeta potential (mV), (±SD) | [d]Aspect within 60 min post formulation preparation |
|---|---|---|---|---|---|---|---|
|  | Peak 1 (nm) | % | Peak 2 (nm) | % |  |  |  |
| ZSNC-PA1 | 265.32 (0.41) | 91% | 4342.11 (33.09) | 9% | 0.273 | −9.22 ± 0.11 | Milky and homogeneous |
| ZSNC-PA2 | 471.03 (4.32) | 80% | 5054.33 (22.08) | 20% | 0.276 | −3.38 ± 0.06 | Milky and homogeneous |

ZSNC-PA1: Self-assembled zein nanocapsules loaded with *Mentha Piperita* (Peppermint) oil and coated with the polyanionic polymer arabic gum.
ZSNC-PA2: Self-assembled zein nanocapsules loaded with *Mentha Piperita* (Peppermint) oil containing the polyanionic polymer arabic gum in the shell of zein.
[a]Determination of the nanoparticles size (nm) by photon correlation spectroscopy.
[b]Polydispersity Index.
[c]Determination of the zeta potential by electrophoretic laser Doppler anemometry.
[d]Description of the ZSNC such as, phase separation, sedimentation, agglomerations or floating.

Example 10

Cationic and Anionic Self-Assembled Zein Core-Shell Nanocapsules (ZSNC) and Microcapsules (ZSMC) Containing PG Immiscible Essential Oils Lemon oil is an essential oil immiscible with PG/zein solution. Thus, oil in water emulsion of lemon oil was firstly optimized with different surfactants and different oil:PG-zein solution ratio (v/v) to obtain droplet size in the range of nm or µm.

10.1 Preparation and Characterization of Emulsions Containing Lemon Oil in PG-Zein Solution In order to obtain stable emulsions of lemon oil in PG-zein solution (o/w), different amounts of lemon oil were emulsified in PG-zein solution (5, 10 and 15% v/v lemon oil in PG-zein solution) in the presence of surfactants under sonication for 1 min. The surfactants used were Tween® 20 or Tween® 80 at a final concentration of 2 or 4% according to the following table (Table 10).

TABLE 10

Composition of different types of lemon oil emulsions in PG-zein solutions

| O/W. Sample number | % of Lemon oil (v/v) in PG-zein solution | % of Tween® 20 (v/v) in PG-zein solution | % of Tween® 80 (v/v) in PG-zein solution | % of PG-zein solution | % Zein concentration (w/v) |
|---|---|---|---|---|---|
| 1 | 5 | 2 | 0 | 93 | 2.5 |
| 2 | 10 | 2 | 0 | 88 | 2.5 |
| 3 | 15 | 2 | 0 | 83 | 2.5 |
| 4 | 5 | 4 | 0 | 91 | 2.5 |
| 5 | 10 | 4 | 0 | 86 | 2.5 |
| 6 | 15 | 4 | 0 | 81 | 2.5 |
| 7 | 5 | 0 | 2 | 93 | 2.5 |
| 8 | 10 | 0 | 2 | 88 | 2.5 |
| 9 | 15 | 0 | 2 | 83 | 2.5 |
| 10 | 5 | 0 | 4 | 91 | 2.5 |
| 11 | 10 | 0 | 4 | 86 | 2.5 |
| 12 | 15 | 0 | 4 | 81 | 2.5 |

Then, o/w emulsions were left at room temperature for 3 days. After that, the aspect and particles sizes for all samples were monitored and visualized under light microscopy.

10.2 Results

The following table (Table 11) shows the macro and microscopical characteristics of lemon oil emulsions indicated in Table 10 (samples from 1 to 12). Generally, all emulsion samples done with Tween® 80, showed bigger droplet size compared to the samples done with Tween® 20, which was ranged from 30 to 50 µm. In addition, samples 1 and 4, which contained Tween® 20 displayed the smaller droplet size which was less than 2 µm. The size of samples 1 and 4 was analyzed as described in Example 1. The results demonstrated that the size of the primary emulsion, in sample 1, was homogeneous (400±4.6 nm) even after one month of incubation at room temperature. However, the droplet size of sample 4 was 2.1±0.9 µm at the same time period. FIG. 7 showed some examples of light microscopy images that represent the particles droplet size for emulsion samples 1, 4, 7 and 10.

TABLE 11

Macro and microscopical characterization of lemon oil emulsions

| O/W Sample number | Estimated size range under light microscopy (µm) | Macroscopical observation after 3 days at room temperature (Presence of phase separation) |
|---|---|---|
| 1 | Less than 1 | NO |
| 2 | 5-10 | YES |
| 3 | 10-30 | YES |
| 4 | 1-2 | NO |
| 5 | 50-60 | YES |
| 6 | 10-30 | YES |
| 7 | 5-10 | YES |
| 8 | 15-25 | YES |
| 9 | 20-30 | YES |
| 10 | 30-50 | YES |
| 11 | 30-50 | YES |
| 12 | 30-50 | YES |

10.3 Preparation and Characterization of Cationic and Anionic Self-Assembled Zein Core-Shell Nanocapsules and Microcapsules Containing Lemon Oil In this case, the nano and microcapsules were prepared by emulsification-in situ surface deposition technique. According to the results obtained from the optimization experiments of o/w emulsions of lemon oil in zein solutions, samples 1 and 4 were selected to prepare both core-shell cationic self-assembled zein nanocapsules (ZSNC-L1) and microcapsules (ZSMC-L1), respectively. For that purpose, emulsions (sample 1 and 4) of lemon oil in zein-PG solution were prepared as described in 10.1 section. Then, 1 mL of said emulsion was added to 4 mL of bidistilled water. In order to obtain core-shell anionic self-assembled zein nanocapsules (ZSNC-L2) and microcapsules (ZSMC-L2), 1 mL of arabic gum aqueous solution (0.25% w/v) was added to both nanocapsules and microcapsules suspension that were freshly prepared, under magnetic stirring, for 5 min at room temperature.

The size and zeta potential were determined as described in Example 1. On the other hand, in order to calculate the encapsulation efficiency, all formulations were done by the same method with lemon oil fluorescently labelled with lipophilic fluorescent probe 1,1'-dioctadecyl-3,3,3',3'-tetramethylindocarbocyanine perchlorate at a concentration of 25 µg/mL oil. Then, the encapsulation efficiency was calculated as described in Example 9. The final formulations of cationic nanocapsules were visualized by light microscopy and Transmission Electron Microscopy.

10.4 Results

Table 12 describes the main physico-chemical properties of freshly prepared core-shell cationic and anionic self-assembled zein nanocapsules and microcapsules (cationic: ZSNC-L1 and ZSMC-L1; anionic: ZSNC-L2 and ZSMC-L2). Both cationic nanocapsules (ZSNC-L1) and microcapsules (ZSMC-L1) displayed a homogeneous size with small polydispersity Index and were positively charged. On the other hand, the presence of the anionic polymer arabic gum significantly increased the particles size. The encapsulation efficiency was very high in all formulations. However, the encapsulation efficiency of lemon oil was observed to be higher in case of both cationic and anionic microcapsules (ZSMC-L1 and ZSMC-L2) compared to nanocapsules. FIG. 8 shows light microscopy images for ZSNC-L1 and ZSMC- L1 and FIG. 9 shows Transmission Electron Microscopy image for cationic ZSNC-L1.

TABLE 12

Physico-chemical characteristics of core-shell cationic and anionic self-assembled zein nanocapsules and microcapsules
Data expressed as mean ± SD (n = 6)

| | $^a$ Size (nm), (±SD) | $^b$ PDI | $^c$ Zeta potential (mV), (±SD) | $^d$ % Encapsulation efficiency of lemon oil (±SD) |
|---|---|---|---|---|
| ZSNC-L1 | 398.53 (4.66) | 0.180 | +7.50 (4.79) | 86.28 (3.82) |
| ZSMC-L1 | 2321.11 (10.83) | 0.133 | +10.54 (1.23) | 96.24 (1.37) |
| ZSNC-L2 | 660.51 (5.022) | 0.221 | −5.54 (2.44) | 85.22 (2.45) |
| ZSMC-L2 | 4177.33 (19.09) | 0.100 | −4.80 (1.77) | 94.77 (3.11) |

ZSNC-L1: Cationic self-assembled zein nanocapsules loaded with lemon oil.
ZSMC-L1: Cationic self-assembled zein microcapsules loaded with lemon oil.
ZSNC-L2: Anionic self-assembled zein nanocapsules loaded with lemon oil.
ZSMC-L2: Anionic self-assembled zein microcapsules loaded with lemon oil.
$^a$ Determination of the nanoparticles size (nm) by photon correlation spectroscopy.
$^b$ Polydispersity Index.
$^c$ Determination of the zeta potential by electrophoretic laser Doppler anemometry.
$^d$ % Encapsulation efficiency: Percentage of the amount of encapsulated lemon oil in the formulations in relation with the initial amount of lemon oil used.

Example 11

Cationic Self-Assembled Zein Core-Shell Nanocapsules (ZSNC) and Microcapsules (ZSMC) Containing Fatty Acids and Non-Volatile Oils

11.1 Preparation and Characterization of Cationic ZSNC and ZSMC Containing Cod Liver Oil and α-Linolenic Acid (ALA) as Non-Volatile Oils In this case, cod liver oil and α-linolenic acid (ALA) as omega-3 fatty acids were selected as models to obtain nanocapsules and microcapsules as dietary supplements with some benefits in cardiovascular health.

Cod liver oil is a nutritional supplement derived from liver of cod fish. It has high levels of the omega-3 fatty acids, eicosapentaenoic acid (EPA) and docosahexaenoic acid (DHA), and very high levels of vitamin A and vitamin D. α-Linolenic acid is an n-3 fatty acid found in many common vegetable oils and is a member of the group of essential fatty acids (EFAs), so called because they cannot be produced within the body and must be acquired through diet. N-3 fatty acids (referred to as ω-3 fatty acids or omega-3 fatty acids) are essential unsaturated fatty acids with a double bond (C=C) starting after the third carbon atom from the end of the carbon chain.

Nanocapsules containing ALA (ZSNC-ALA) were obtained by the in situ nanoprecipitation-surface deposition technique described in Example 9 and microcapsules containing cod liver oil (ZSMC-CLO) were prepared by emulsification-in situ surface deposition technique as described in Example 10, but in this case the surfactant was Lutrol® L 44. Both formulations were characterized as previously described in Examples 9 and 10.

11.2 Results

Table 13 shows the physico-chemical characteristics of core-shell cationic ZSNC and ZSMC containing ALA and cod liver oil, respectively.

TABLE 13

Physico-chemical characteristics of core-shell cationic self-assembled zein nanocapsules and microcapsules containing cod liver oil and α-linolenic acid (ALA)
Data expressed as mean ± SD (n = 6)

| | $^a$ Size (nm), (±SD) | $^b$ PDI | $^c$ Zeta potential (mV), (±SD) | $^d$ % Encapsulation efficiency of non-volatile oils (±SD) |
|---|---|---|---|---|
| ZSNC-ALA | 730.11 (2.66) | 0.140 | +3.50 (4.79) | 56.63 (3.82) |
| ZSMC-CLO | 6321.11 (13.45) | 0.263 | +10.54 (1.23) | 63.11 (5.22) |

ZSNC-ALA: Self-assembled zein nanocapsules loaded with linolenic acid ZSMC-CLO: Self-assembled zein microcapsules loaded with cod liver oil
$^a$ Determination of the nanoparticles size (nm) by photon correlation spectroscopy.
$^b$ Polydispersity Index.
$^c$ Determination of the zeta potential by electrophoretic laser Doppler anemometry.
$^d$ % Encapsulation efficiency: Percentage of the amount of encapsulated non-volatile oil in the nanoparticles formulations in relation with the initial amount of the non-volatile oils used.

REFERENCES

1. Kumari, A., S. K. Yadav, and S. C. Yadav, *Biodegradable polymeric nanoparticles based drug delivery systems*. Colloids Surf B Biointerfaces, 2010. 75(1): p. 1-18.
2. Lai, T., et al., *Clinical application of a novel sliver nanoparticles biosensor based on localized surface plasmon resonance for detecting the microalbuminuria*. Acta Biochim Biophys Sin (Shanghai), 2010. 42(11): p. 787-92.
3. Santipanichwong, R., et al., *Core-shell biopolymer nanoparticles produced by electrostatic deposition of beet pectin onto heat-denatured beta-lactoglobulin aggregates*. J Food Sci, 2008. 73(6): p. N23-30.
4. Sanoj Rejinold, N., et al., *Curcumin-loaded biocompatible thermoresponsive polymeric nanoparticles for cancer drug delivery*. J Colloid Interface Sci, 2011. 360(1): p. 39-51.
5. Bourquin, C., et al., *Delivery of immunostimulatory RNA oligonucleotides by gelatin nanoparticles triggers an efficient antitumoral response*. J Immunother, 2010. 33(9): p. 935-44.
6. Tseng, C. L., et al., *Development of gelatin nanoparticles with biotinylated EGF conjugation for lung cancer targeting*. Biomaterials, 2007. 28(27): p. 3996-4005.
7. Tan, S. T., et al., *Biocompatible and biodegradable polymer nanofibers displaying superparamagnetic properties*. Chemphyschem, 2005. 6(8): p. 1461-5.
8. Sanoj Rejinold, N., et al., *Biocompatible, biodegradable and thermo-sensitive chitosan-g-poly (N-isopropylacrylamide) nanocarrier for curcumin drug delivery*. Int J Biol Macromol, 2011. 49(2): p. 161-72.
9. Cho, H. S., et al., *Biodegradability and biodegradation rate of poly(caprolactone)-starch blend and poly(butylene succinate) biodegradable polymer under aerobic and anaerobic environment*. Waste Manag, 2011. 31(3): p. 475-80.
10. Hu, X. and X. Jing, *Biodegradable amphiphilic polymer-drug conjugate micelles*. Expert Opin Drug Deliv, 2009. 6(10): p. 1079-90.
11. Tang, Y. and J. Singh, *Biodegradable and biocompatible thermosensitive polymer based injectable implant for controlled release of protein*. Int J Pharm, 2009. 365(1-2): p. 34-43.
12. Yu, N. Y., et al., *Biodegradable poly(alpha-hydroxy acid) polymer scaffolds for bone tissue engineering*. J Biomed Mater Res B Appl Biomater, 2010. 93(1): p. 285-95.

13. Kim, H. I., et al., *Biodegradable polymer films for releasing nanovehicles containing sirolimus*. Drug Deliv, 2009. 16(4): p. 183-8.
14. Markvicheva, E. A., et al., *[Biodegradable polymer microparticles with entraped herbal extracts: preparation with supercritical carbon dioxide and use for tissue repair]*. Biomed Khim, 2009. 55(4): p. 479-88.
15. Lawton, J. W., *Zein: A History of Processing and Use*. Cereal Chem., 2002. 79(1): p. 1-18.
16. Guo, H. X., J. Heinamaki, and J. Yliruusi, *Stable aqueous film coating dispersion of zein*. J Colloid Interface Sci, 2008. 322(2): p. 478-84.
17. Li, X. N., H. X. Guo, and J. Heinamaki, *Aqueous coating dispersion (pseudolatex) of zein improves formulation of sustained-release tablets containing very water-soluble drug*. J Colloid Interface Sci, 2010. 345(1): p. 46-53.
18. Podaralla, S, and O. Perumal, *Preparation of zein nanoparticles by pH controlled nanoprecipitation*. J Biomed Nanotechnol, 2010. 6(4): p. 312-7.
19. Luo, Y., et al., *Preparation and characterization of zein/chitosan complex for encapsulation of alpha-tocopherol, and its in vitro controlled release study*. Colloids Surf B Biointerfaces, 2011. 85(2): p. 145-52.
20. Parris, N., P. H. Cooke, and K. B. Hicks, *Encapsulation of essential oils in zein nanospherical particles*. J Agric Food Chem, 2005. 53(12): p. 4788-92.
21. de Sousa, F. O., et al., *Effect of zein on biodegradable inserts for the delivery of tetracycline within periodontal pockets*. J Biomater Appl, 2011.
22. Salerno, A., et al., *Design of novel three-phase PCL/TZ-HA biomaterials for use in bone regeneration applications*. J Mater Sci Mater Med, 2010. 21(9): p. 2569-81.
23. Chen, L., et al., *In vitro study of the release properties of soy-zein protein microspheres with a dynamic artificial digestive system*. J Agric Food Chem, 2010. 58(17): p. 9861-7.
24. Wang, Y. and G. W. Padua, *Formation of zein microphases in ethanol-water*. Langmuir, 2010. 26(15): p. 12897-901.
25. Liu, L., et al., *Pectin/zein beads for potential colon-specific drug delivery: synthesis and in vitro evaluation*. Drug Deliv, 2006. 13(6): p. 417-23.
26. Muthuselvi, L. and A. Dhathathreyan, *Simple coacervates of zein to encapsulate Gitoxin*. Colloids Surf B Biointerfaces, 2006. 51(1): p. 39-43.
27. Lin, T., et al., *The biodegradation of zein in vitro and in vivo and its application in implants*. AAPS PharmSciTech, 2011. 12(1): p. 172-6.
28. Jin, Q. Z. a. M., *zein nanoparticles produced by liquid-liquid dispersion*. Food Hydrocolloids, 2009. 23: p. 2380-2387.
29. Lai, L. F. and H. X. Guo, *Preparation of new 5-fluorouracil-loaded zein nanoparticles for liver targeting*. Int J Pharm, 2011. 404(1-2): p. 317-23.
30. Zhang, Q. Z. M. J. D. X. H. T. W., *Application of Supercritical Anti-Solvent Technologies for the Synthesis of Delivery Systems of Bioactive Food Components*. Food Biophysics 2008(3): p. 186-190.
31. Patent, U.S., *Aqueous dispersions of zein and preparation thereof*. U.S. Pat. No. 5,324,351
32. Schaffazick, S. R., A. R. Pohlmann, and S. S. Guterres, *Nanocapsules, nanoemulsion and nanodispersion containing melatonin: preparation, characterization and stability evaluation*. Pharmazie, 2007. 62(5): p. 354-60.
33. Rodriguez-Emmenegger, C., et al., *Polymeric nanocapsules ultra stable in complex biological media*. Colloids Surf B Biointerfaces, 2011. 83(2): p. 376-81.
34. Fukui, Y. and K. Fujimoto, *The preparation of sugar polymer-coated nanocapsules by the layer-by-layer deposition on the liposome*. Langmuir, 2009. 25(17): p. 10020-5.
35. Song, R., et al., *Sequence, regulation, and evolution of the maize 22-kD alpha zein gene family*. Genome Res, 2001. 11(11): p. 1817-25.
36. Esen, A., *Separation of alcohol-soluble proteins (zeins) from maize into three fractions by differential solubility*. Plant Physiol, 1986. 80(3): p. 623-7.
37. Graciela W. Padua and, Q. W., *Controlled Self-Organization of Zein Nanostructures for Encapsulation of Food Ingredients*. BOOK: Micro/Nanoencapsulation of Active Food Ingredients, 2009. Chapter 9 p. 143-156.
38. Arbos, P., et al., *Quantification of the bioadhesive properties of protein-coated PVM/MA nanoparticles*. Int J Pharm, 2002. 242(1-2): p. 129-36.
39. Salman, H. H., et al., *Bioadhesive mannosylated nanoparticles for oral drug delivery*. J Nanosci Nanotechnol, 2006. 6(9-10): p. 3203-9.
40. Kakkar, V., et al., *Exploring solid lipid nanoparticles to enhance the oral bioavailability of curcumin*. Mol Nutr Food Res, 2011. 55(3): p. 495-503.
41. Meng, N., et al., *Controlled release and antibacterial activity chlorhexidine acetate (CA) intercalated in montmorillonite*. Int J Pharm, 2009. 382(1-2): p. 45-9.
42. Peh, K. K. and C. F. Wong, *Polymeric films as vehicle for buccal delivery: swelling, mechanical, and bioadhesive properties*. J Pharm Pharm Sci, 1999. 2(2): p. 53-61.

The invention claimed is:
1. A nanoparticle selected from the group consisting of:
   a) a matrix nanosphere, wherein said matrix nanosphere comprises a matrix, said matrix comprising:
      (i) a vegetable hydrophobic protein; and
      (ii) at least a water miscible non-volatile organic solvent of the vegetable hydrophobic protein; and
   b) a core-shell vesicular nanocapsule, wherein said core-shell vesicular nanocapsule comprises a core and a shell, said shell comprising:
      (i) a vegetable hydrophobic protein; and
      (ii) at least a water miscible non-volatile organic solvent of the vegetable hydrophobic protein,
wherein the vegetable hydrophobic protein is a prolamine and,
wherein the water miscible non-volatile organic solvent is propylene glycol or a mixture of propylene glycol and other primary and/or secondary solvents, and wherein the water miscible non-volatile organic solvent is within the matrix of the matrix nanosphere and within the shell of the core-shell vesicular nanocapsule.

2. The nanoparticle according to claim 1, further comprising a product of interest.

3. The nanoparticle according to claim 1, wherein the prolamine is zein.

4. A solution suitable for forming a nanoparticle according to claim 1, said solution containing a vegetable hydrophobic protein in a medium, said medium comprising at least a water miscible non-volatile organic solvent and, optionally, an aqueous medium, wherein the amount of aqueous medium is lower than the necessary amount of aqueous medium to form nanoparticles, wherein the medium comprising at least a water miscible non-volatile organic solvent does not comprise a volatile organic solvent, wherein the amount of vegetable hydrophobic protein is comprised between 0.01 and 50% (w/v) with the proviso that when the vegetable hydrophobic protein is gliadin, then the amount of vegetable hydrophobic protein is higher than 0.1%, wherein the vegetable hydrophobic protein is a prolamine and, wherein the water miscible non-volatile organic solvent is propylene glycol or a mixture of propylene glycol and other primary and/or secondary solvents.

5. A solution, suspension or emulsion suitable for forming a nanoparticle according to claim 1, said solution, suspension or emulsion containing a vegetable hydrophobic protein and a product of interest dissolved, suspended or emulsified in a medium, said medium comprising at least a water miscible non-volatile organic solvent and, optionally, a surfactant and, optionally, an aqueous medium, wherein the amount of aqueous medium is lower than the necessary amount of aqueous medium to form nanoparticles, wherein the medium comprising at least a water miscible non-volatile organic solvent does not comprise a volatile organic solvent, wherein the amount of vegetable hydrophobic protein is comprised between 0.01 and 50% (w/v), wherein the vegetable hydrophobic protein is a prolamine and, wherein the water miscible non-volatile organic solvent is propylene glycol or a mixture of propylene glycol and other primary and/or secondary solvents.

6. A suspension of nanoparticles according to claim 1 in a medium, said medium comprising at least a water miscible non-volatile organic solvent and a vegetable hydrophobic protein non-solvent, and not comprising a volatile organic solvent, wherein the vegetable hydrophobic protein is a prolamine and, wherein the water miscible non-volatile organic solvent is propylene glycol or a mixture of propylene glycol and other primary and/or secondary solvents.

7. A composition comprising at least one nanoparticle according to claim 1, and a carrier.

8. The composition according to claim 7 wherein said composition is selected from a pharmaceutical composition, a cosmetic composition, an agricultural composition and a food composition.

9. The composition according to claim 7 further comprising a product of interest selected from the group consisting of a herbicide, an insecticide, a fungicide, an anti-aging product, an anti-acne product, a facial care product, a pigmented cosmetic, a cosmetical, a personal care product, a product for sunscreen/suncare, a product for tooth-cleaners, toothpastes, or rinses, a product for shampooes, a perfume, a hair products, a food additive, an essential oil, *Mentha piperita* oil, Thyme oil, cinnamon oil, eugenol, lemon oil, curcumin, folic acid, 4-aminobenzoic acid, niacin or vitamin B3, pantothenic acid or vitamin B5, thiamine monophosphate, thiamine pyrophosphate, thiamine triphosphate, ascorbic acid, pteroylpolyglutamic acids, folinic acid, nicotinic acid, hyaluronic acid, thioctic acid, p-coumaric acid, caffeic acid, a vitamin of the A, D, E, K families and derivatives thereof, a phospholipid, a carotenoid, a fatty acid, an omega-3 fatty acid, cod liver oil, linolenic acid, an amino acid, a phytostanol, a phytosterol, a polyphenol, chlorhexidine, bovine serum albumin, an analgesic agent, an antialopecia agent, an antianginal agent, an antibacterial agent, an antidepressant agent, an antifungal agent, an antihypertensive agent, an antiinflammatoy agent, an antineoplastic agent, an antipyretic agent, an antipsycothic agent, an anxiolytic agent, a bronchodilator agent, a glucocorticoid, an immunosuppressant agent, acetylsalicylic acid, alpha-atrial natriuretic peptide, arginine vasopressin, atropine, augmerosen, atorvastatin, avastin, calcitonins, chlorhexidine, chorionic gonadotropins, corticotropin, desmopressin, epibatidine, erbitux, exenatide, herceptin, humira, humulin, ketoconazole, lanreotide, lutropin alpha, metoprolol, minoxidil, nesiritide, octreotide, paclitaxel, paracetamol, pegaptanib, recombinant follicle stimulating hormone, a recombinant growth factor, remicade, rituxan, sermorelin, somatotropin, a taxane derivative, taxol, teriparatide acetate, thyrotropin, triclosan, urofollitropin, xolair, actinomycin D, albendazole, aldosterone, alprazolam, amiodarone, amitriptyline, amprenavir, asimadoline, atorvastatin, bunitrolol, buspirone, camptothecin, carbamazepine, carvedilol, celiprolol, cyclosporine A, cimetidine, clotrimazole, colchicine, cortisone, daunorubicin, debrisoquine, dexamethasone, diazepam, digitoxin, digoxin, diltiazem, docetaxel, domperidone, doxorubicin, efavirenz, epirubicin, erythromycin, ergotamine, estradiol, estradiol glucuronide, erlotinib, etoposide, phenytoin, fentanyl, felodipine, phenothiazines, fexofenadine, fluoroquinolones, fluorouracil, FK-506, gentamicin, griseofulvin, hydrocortisone, imatinib, indinavir, itraconazole, ivermectin, ketoconazole, kaempferol, levofloxacin, lidocaine, loperamide, losartan, lovastatin, mebendazole, methylprednisolone, methotrexate, mibefradil, midazolam, nisoldipine, morphine, nelfinavir, nicardipine, nitrendipine, nifedipine, ondansetron, paclitaxel, pentazocine, praziquantel, prednisolone, prednisone, quercetin, quinidine, ranitidine, rapamycin, rifabutin, rifampicin, ritonavir, saquinavir, sirolimus, sulfamethizole, tacrolimus, tamoxifen, talinolol, teniposide, terfenadine, tetracycline, topotecan, triamcinolone, valspodar, verapamil, vinblastine, vincristine, vindesine, zopiclone, and mixtures thereof.

10. A composition comprising a solution, suspension or emulsion according to claim 5, and a carrier.

11. The composition according to claim 10 wherein said composition is selected from a pharmaceutical composition, a cosmetic composition, an agricultural composition and a food composition.

12. Composition according to claim 10 further comprising a product of interest selected from the group consisting of a herbicide, an insecticide, a fungicide, an anti-aging product, an anti-acne product, a facial care product, a pigmented cosmetic, a cosmetical, a personal care product, a product for sunscreen/suncare, a product for tooth-cleaners, toothpastes, or rinses, a product for shampooes, a perfume, a hair products, a food additive, an essential oil, *Mentha piperita* oil, Thyme oil, cinnamon oil, eugenol, lemon oil, curcumin, folic acid, 4-aminobenzoic acid, niacin or vitamin B3, pantothenic acid or vitamin B5, thiamine monophosphate, thiamine pyrophosphate, thiamine triphosphate, ascorbic acid, pteroylpolyglutamic acids, folinic acid, nicotinic acid, hyaluronic acid, thioctic acid, p-coumaric acid, caffeic acid, a vitamin of the A, D, E, K families and derivatives thereof, a phospholipid, a carotenoid, a fatty acid, an omega-3 fatty acid, cod liver oil, linolenic acid, an amino acid, a phytostanol, a phytosterol, a polyphenol, chlorhexidine, bovine serum albumin, an analgesic agent, an antialopecia agent, an antianginal agent, an antibacterial agent, an antidepressant agent, an antifungal agent, an antihypertensive agent, an antiinflammatoy agent, an antineoplastic agent, an antipyretic agent, an antipsycothic agent, an anxiolytic agent, a bronchodilator agent, a glucocorticoid, an immunosuppressant agent, acetylsalicylic acid, alpha-atrial natriuretic peptide, arginine vasopressin, atropine, augmerosen, atorvastatin, avastin, calcitonins, chlorhexidine, chorionic gonadotropins, corticotropin, desmopressin, epibatidine, erbitux, exenatide, herceptin, humira, humulin, ketoconazole, lanreotide, lutropin alpha, metoprolol, minoxidil, nesiritide, octreotide, paclitaxel, paracetamol, pegaptanib, recombinant follicle stimulating hormone, a recombinant growth factor, remicade, rituxan, sermorelin, somatotropin, a taxane derivative, taxol, teriparatide acetate, thyrotropin, triclosan, urofollitropin, xolair, actinomycin D, albendazole, aldosterone, alprazolam, amiodarone, amitriptyline, amprenavir, asimadoline, atorvastatin, bunitrolol, buspirone, camptothecin, carbamazepine, carvedilol, celiprolol, cyclosporine A, cimetidine, clotrimazole, colchicine, cortisone, daunorubicin, debrisoquine, dexamethasone, diazepam, digitoxin, digoxin, diltiazem, docetaxel, domperidone, doxorubicin, efavirenz, epirubicin, erythromycin, ergotamine, estradiol, estradiol glucuronide, erlotinib, etoposide, phenytoin, fentanyl, felodipine, phenothiazines, fexofenadine, fluoroquinolones, fluorouracil, FK-506, gentamicin, griseofulvin, hydrocortisone, imatinib, indinavir, itraconazole, ivermectin, ketoconazole, kaempferol, levofloxacin, lidocaine, loperamide, losartan, lovastatin, mebendazole, methylprednisolone, methotrexate, mibefradil, midazolam, nisoldipine, morphine, nelfinavir, nicardipine, nitrendipine, nifedipine, ondansetron, paclitaxel, pentazocine, praziquantel, prednisolone, prednisone, quercetin, quinidine, ranitidine, rapamycin, rifabutin, rifampicin, ritonavir, saquinavir, sirolimus, sulfamethizole, tacrolimus, tamoxifen, talinolol, teniposide, terfenadine, tetracycline, topotecan, triamcinolone, valspodar, verapamil, vinblastine, vincristine, vindesine, zopiclone, and mixtures thereof.

13. A composition comprising a solution according to claim 4, and a carrier.

14. A composition comprising a suspension according to claim 6, and a carrier.

15. A foodstuff comprising a nanoparticle according to claim 1.

16. A food additive comprising a nanoparticle according to claim 2, wherein the product of interest is the antioxidant curcumin.

17. A dietary supplement comprising a nanoparticle according to claim 2, wherein the product of interest is an oil selected from cod liver oil and linolenic acid.

18. A method of treatment and/or prevention of a buccal or external body infection in a subject comprising the administration to said subject of a nanoparticle according to claim 2 loaded with the antimicrobial drug chlorhexidine.

* * * * *